US011219458B2

(12) United States Patent
Orion et al.

(10) Patent No.: US 11,219,458 B2
(45) Date of Patent: Jan. 11, 2022

(54) APPARATUSES AND METHODS FOR USE IN SURGICAL VASCULAR ANASTOMOTIC PROCEDURES

(71) Applicant: VASCULAR GRAFT SOLUTIONS LTD, Tel-Aviv (IL)

(72) Inventors: Eyal Orion, Ramat Efal (IL); Boaz Harari, Ganey Tikva (IL)

(73) Assignee: VASCULAR GRAFT SOLUTIONS LTD, Tel-Aviv (IL)

( * ) Notice: Subject to any disclaimer, the term of this patent is extended or adjusted under 35 U.S.C. 154(b) by 152 days.

(21) Appl. No.: 16/605,553

(22) PCT Filed: May 1, 2018

(86) PCT No.: PCT/IB2018/053016
§ 371 (c)(1),
(2) Date: Oct. 16, 2019

(87) PCT Pub. No.: WO2018/203237
PCT Pub. Date: Nov. 8, 2018

(65) Prior Publication Data
US 2020/0121321 A1 Apr. 23, 2020

Related U.S. Application Data
(60) Provisional application No. 62/492,323, filed on May 1, 2017.

(51) Int. Cl.
A61B 17/11 (2006.01)
A61B 17/00 (2006.01)
(Continued)

(52) U.S. Cl.
CPC .......... *A61B 17/11* (2013.01); *A61B 17/0057* (2013.01); *A61B 17/32053* (2013.01);
(Continued)

(58) Field of Classification Search
CPC ................ A61B 17/11; A61B 17/0057; A61B 17/32053; A61B 2017/00252;
(Continued)

(56) References Cited

U.S. PATENT DOCUMENTS 3,874,388 A 4/1975 King et al.
5,447,515 A 9/1995 Robicsek
(Continued)

FOREIGN PATENT DOCUMENTS

WO 2015126985 A1 8/2015

OTHER PUBLICATIONS

International Search Report and Written Opinion (PCT Application No. PCT/IB2018/053016); dated Aug. 7, 2018; 8 pages.
(Continued)

*Primary Examiner* — Kathleen S Holwerda
*Assistant Examiner* — Uyen N Vo
(74) *Attorney, Agent, or Firm* — Howard & Howard Attorneys PLLC

(57) ABSTRACT

Apparatuses and methods for use in surgical vascular anastomotic procedures. Apparatus includes a blood vessel inner wall (BVIW) sealing and hole forming device, and a hole forming actuator. BVIW sealing and hole forming device includes a hole sealing device, and an anastomotic hole generating device. Hole sealing device includes a sheath that fully encloses and holds a self-expanding hole sealing assembly, a manual hole sealing controller assembly, and a flexible control wire enclosed within a flexible tube. Anastomotic hole generating device includes outer and inner assemblies, with a conically shaped anastomotic hole generating member. Hole forming actuator includes outer and inner assemblies. Also disclosed are procedures for performing surgical vascular anastomosis using the disclosed apparatuses and methods. Particularly applicable for use in (Continued)

clampless types of (end-to-side) surgical vascular anastomotic procedures, for performing coronary artery bypass grafting (CABG).

33 Claims, 24 Drawing Sheets

(51) Int. Cl.
*A61B 17/3205* (2006.01)
*A61B 17/02* (2006.01)

(52) U.S. Cl.
CPC .............. *A61B 2017/0061* (2013.01); *A61B 2017/00252* (2013.01); *A61B 2017/00336* (2013.01); *A61B 2017/00592* (2013.01); *A61B 2017/00597* (2013.01); *A61B 2017/00623* (2013.01); *A61B 2017/0287* (2013.01); *A61B 2017/1107* (2013.01); *A61B 2017/1135* (2013.01)

(58) Field of Classification Search
CPC .......... A61B 2017/00336; A61B 2017/00592; A61B 2017/00597; A61B 2017/0061; A61B 2017/00623; A61B 2017/0287; A61B 2017/1107; A61B 2017/1135; A61B 2017/00292; A61B 2090/08021; A61B 17/0206; A61B 2017/00243; A61B 2017/00526; A61B 2017/00986; A61B 2017/0243

See application file for complete search history.

(56) References Cited

U.S. PATENT DOCUMENTS

| | | |
|---|---|---|
| 5,571,167 A | 11/1996 | Maginot |
| 5,772,669 A | 6/1998 | Vrba |
| 5,797,920 A | 8/1998 | Kim |
| 6,056,762 A | 5/2000 | Nash et al. |
| 6,135,981 A | 10/2000 | Dyke |
| 6,171,319 B1* | 1/2001 | Nobles ................ A61B 17/11 606/151 |
| 6,176,867 B1 | 1/2001 | Wright |
| 6,190,400 B1 | 2/2001 | Van De Moer et al. |
| 6,234,995 B1 | 5/2001 | Peacock, III |
| 6,395,015 B1 | 5/2002 | Borst et al. |
| 6,398,797 B2 | 6/2002 | Bombard et al. |
| 6,409,739 B1 | 6/2002 | Nobles et al. |
| 6,428,555 B1 | 8/2002 | Koster, Jr. |
| 6,620,177 B2 | 9/2003 | Buelna et al. |
| 6,712,831 B1 | 3/2004 | Kaplan et al. |
| 6,814,743 B2 | 11/2004 | Chin et al. |
| 7,947,062 B2 | 5/2011 | Chin et al. |
| 8,052,639 B2 | 11/2011 | Wilson |
| 8,114,102 B2 | 2/2012 | Galdonik et al. |
| 8,366,706 B2 | 2/2013 | Buchbinder et al. |
| 8,486,098 B2 | 7/2013 | Blake, III |
| 8,932,325 B2 | 1/2015 | Stanley et al. |
| 8,945,235 B2 | 2/2015 | Horton et al. |
| 2004/0215233 A1 | 10/2004 | Kaplan et al. |
| 2004/0249342 A1* | 12/2004 | Khosravi ........ A61M 25/10182 604/96.01 |
| 2005/0216043 A1 | 9/2005 | Blatter et al. |
| 2006/0079915 A1 | 4/2006 | Chin et al. |
| 2006/0190036 A1 | 8/2006 | Wendel et al. |
| 2006/0206121 A1 | 9/2006 | Chin et al. |
| 2008/0275479 A1 | 11/2008 | Chin et al. |
| 2009/0099596 A1 | 4/2009 | McGuckin, Jr. et al. |
| 2009/0299387 A1 | 12/2009 | Navia |
| 2011/0288581 A1* | 11/2011 | Paul, Jr ............. A61B 17/0057 606/213 |
| 2013/0023902 A1 | 1/2013 | Oostman, Jr. |
| 2015/0031959 A1 | 1/2015 | Beane et al. |
| 2016/0100860 A1* | 4/2016 | Lenker ............... A61B 17/3478 604/95.01 |

OTHER PUBLICATIONS

Extended European Search Report (EP Application No./Patent No. 18794964.9-1122/ 3618730 PCT/IB2018053016); dated May 20, 2020; 9 pages.

* cited by examiner

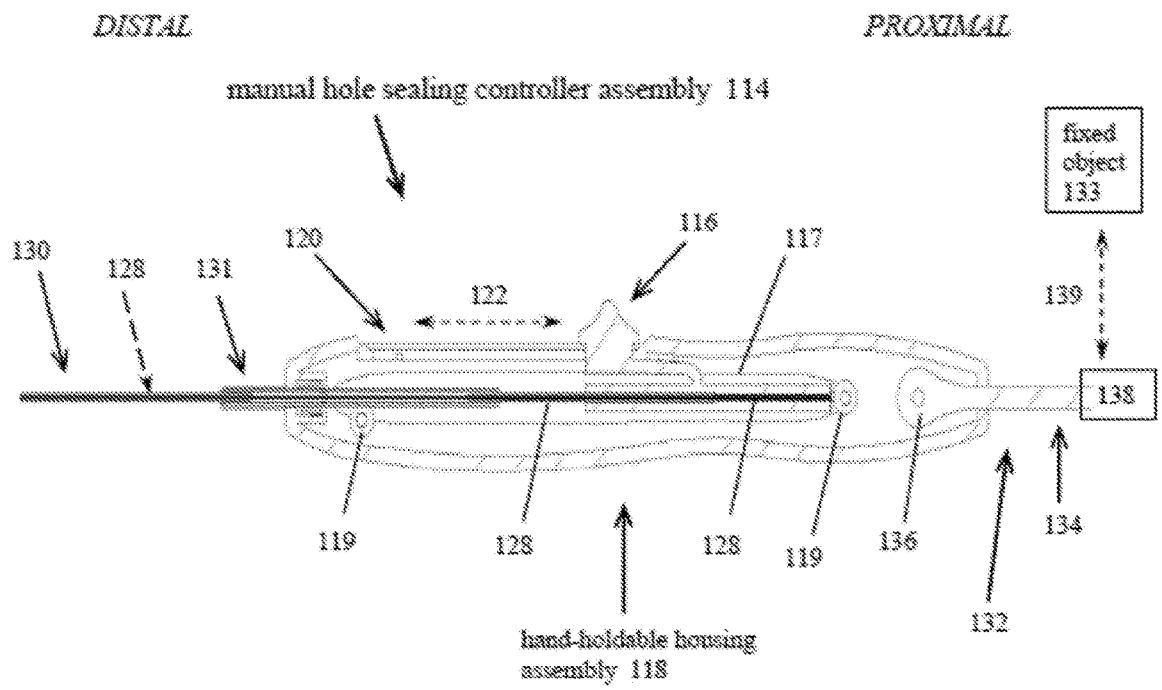
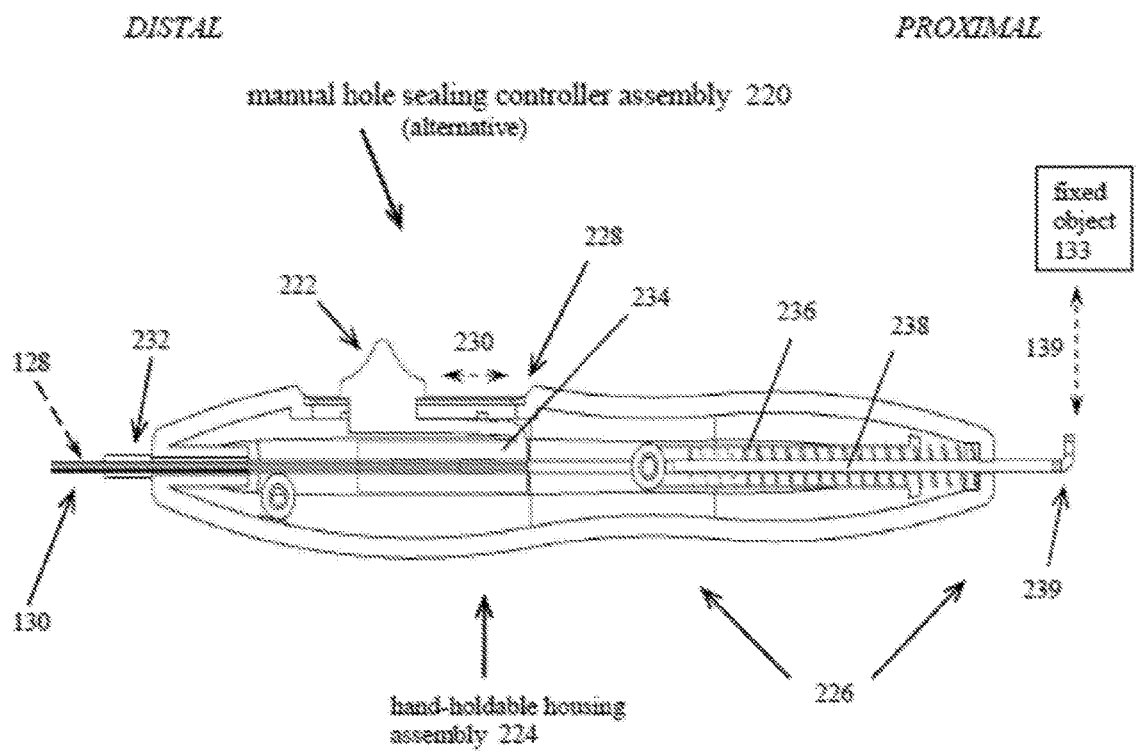

(perspective view)
anastomotic hole generating device 108
[non-activated]

(exploded, perspective view)
anastomotic hole generating device 108

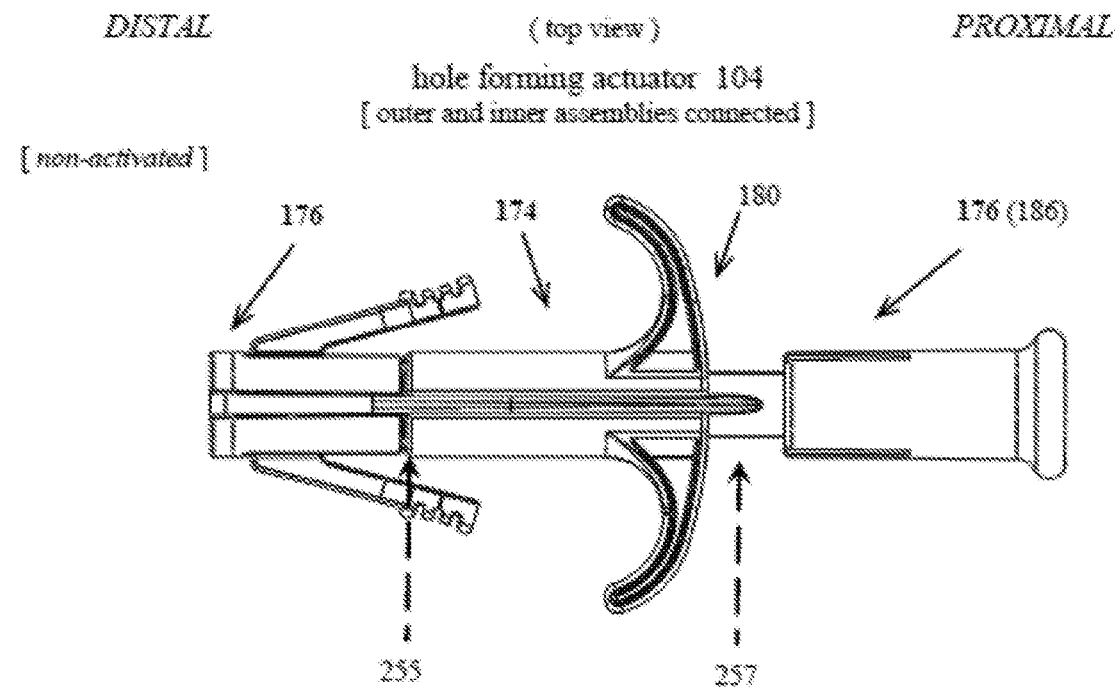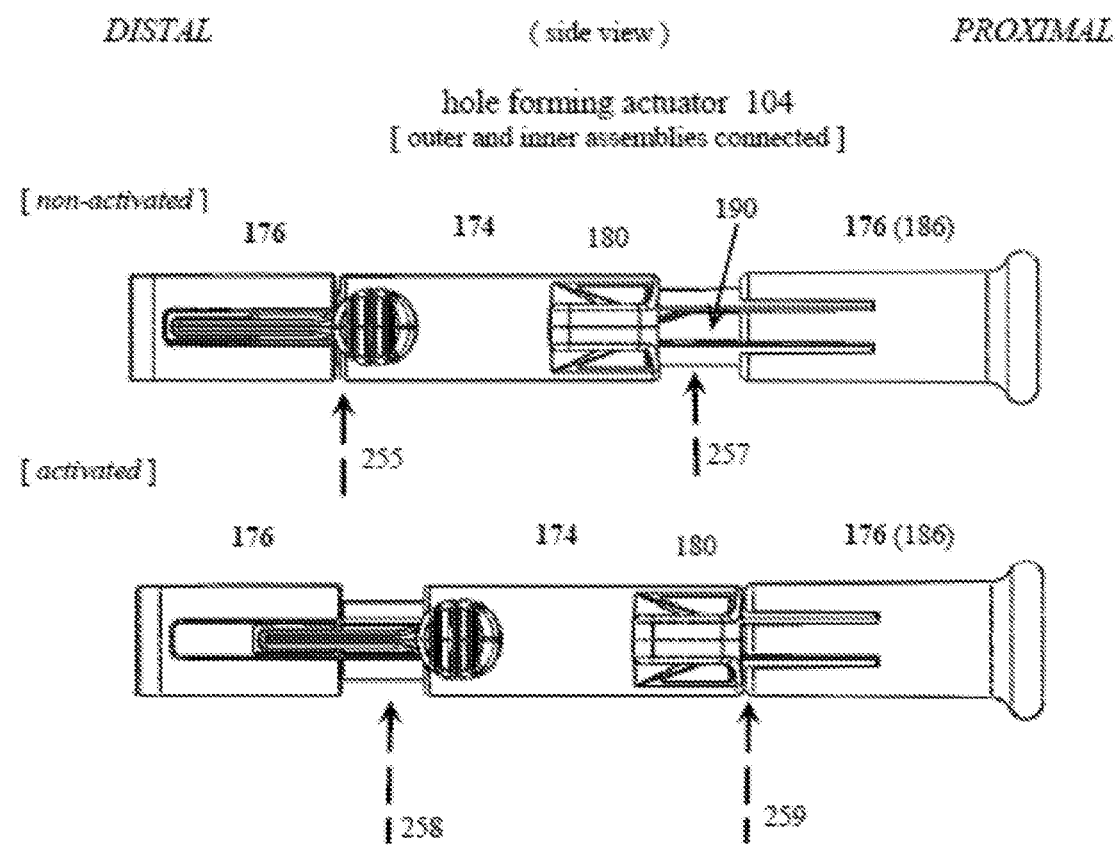

*DISTAL* (perspective view) *PROXIMAL* hole forming actuator 104
[ outer and inner assemblies connected ]

*DISTAL* (perspective view) *PROXIMAL* hole forming actuator 104
[ outer and inner assemblies connected ]

DISTAL (top view) PROXIMAL
hole forming actuator 104
[ outer and inner assemblies non-connected; 'slide-on' cover ]

DISTAL (side view) PROXIMAL
hole forming actuator 104
[ outer and inner assemblies connected; 'slide-on' cover ]

DISTAL   (top view)   PROXIMAL hole forming actuator 250
(alternative)
[ outer and inner assemblies non-connected; 'screw-on' cover ]

DISTAL   (side view)   PROXIMAL hole forming actuator 250
(alternative)
[ outer and inner assemblies non-connected; 'screw-on' cover ]

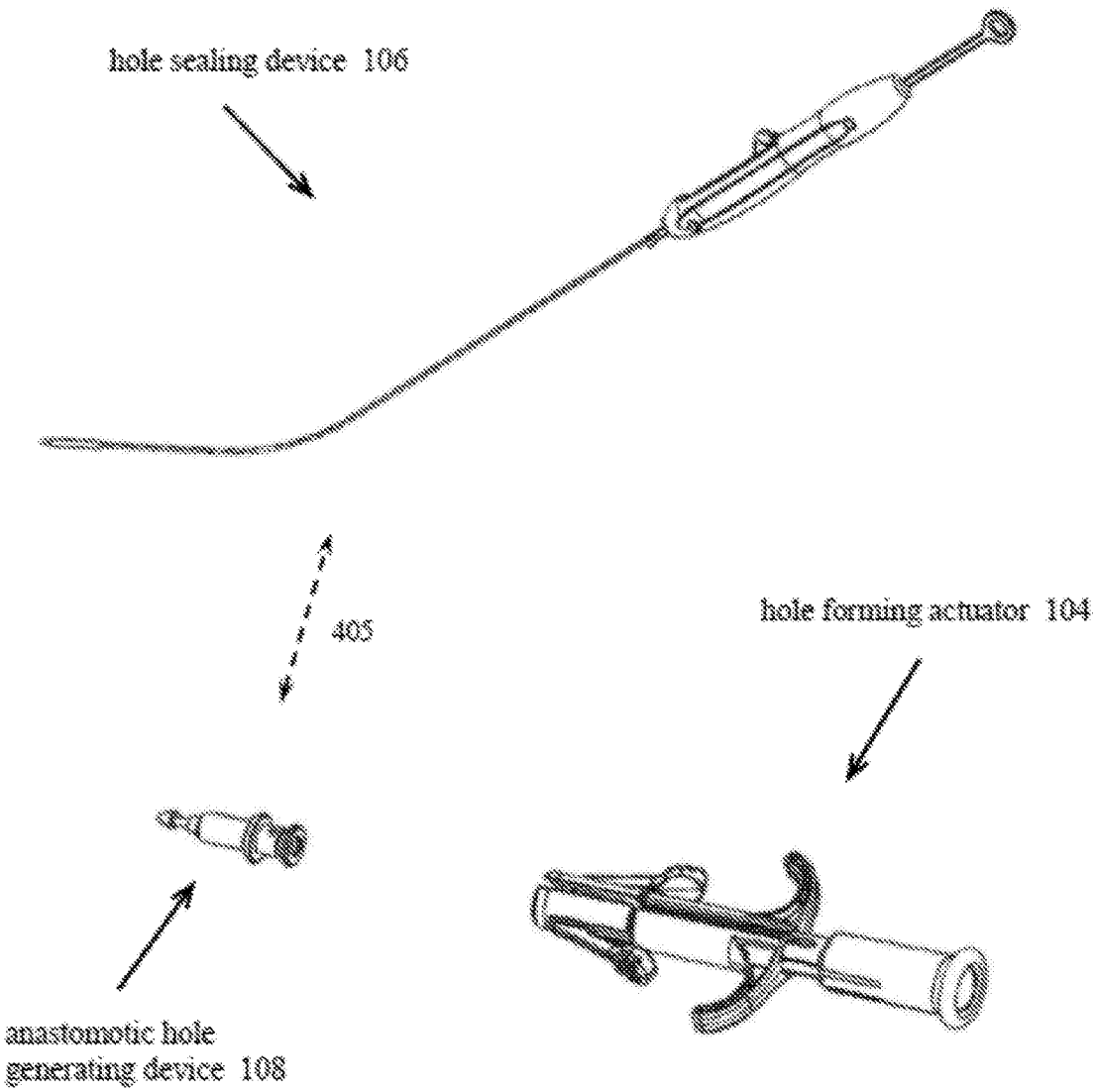

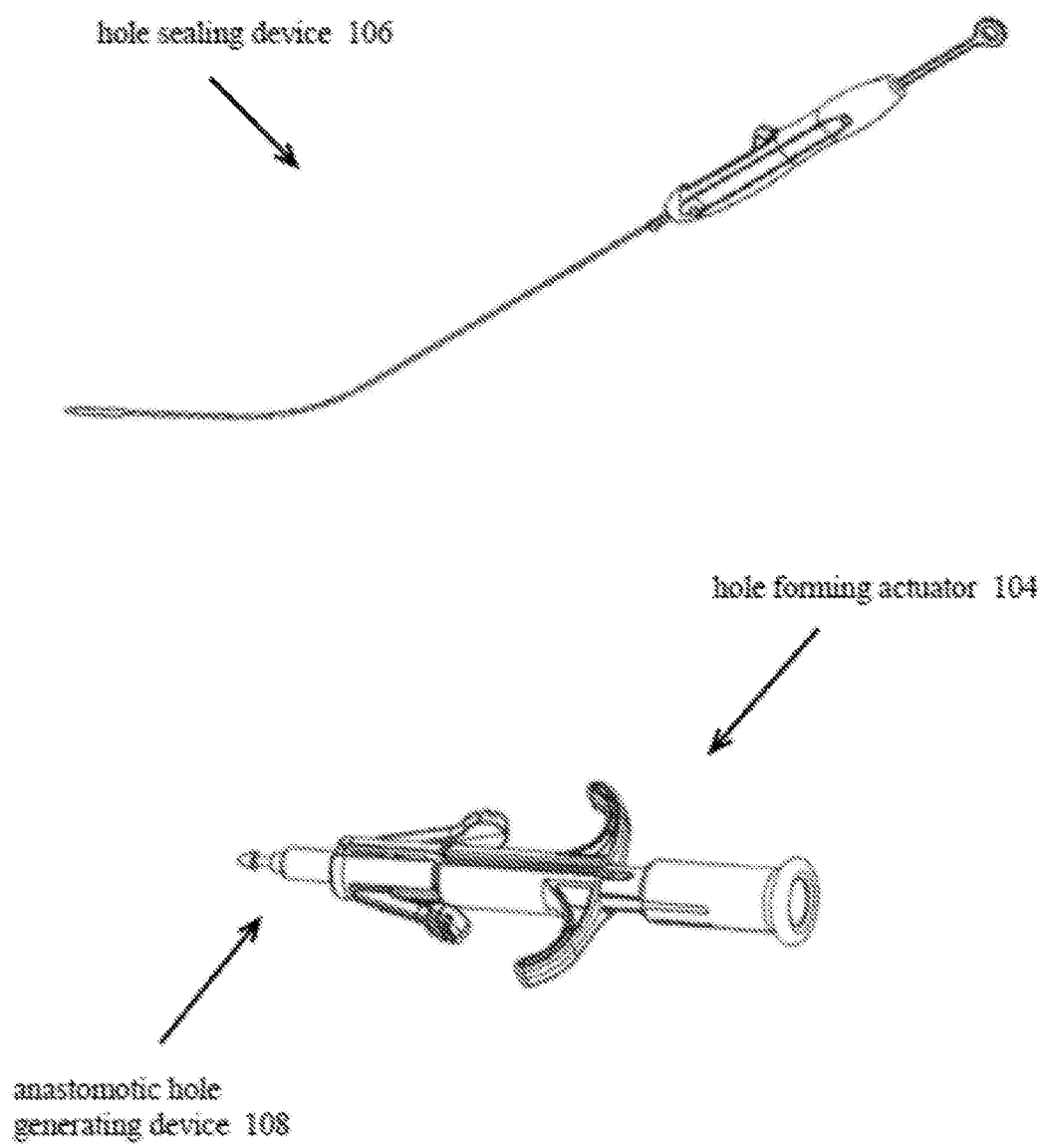

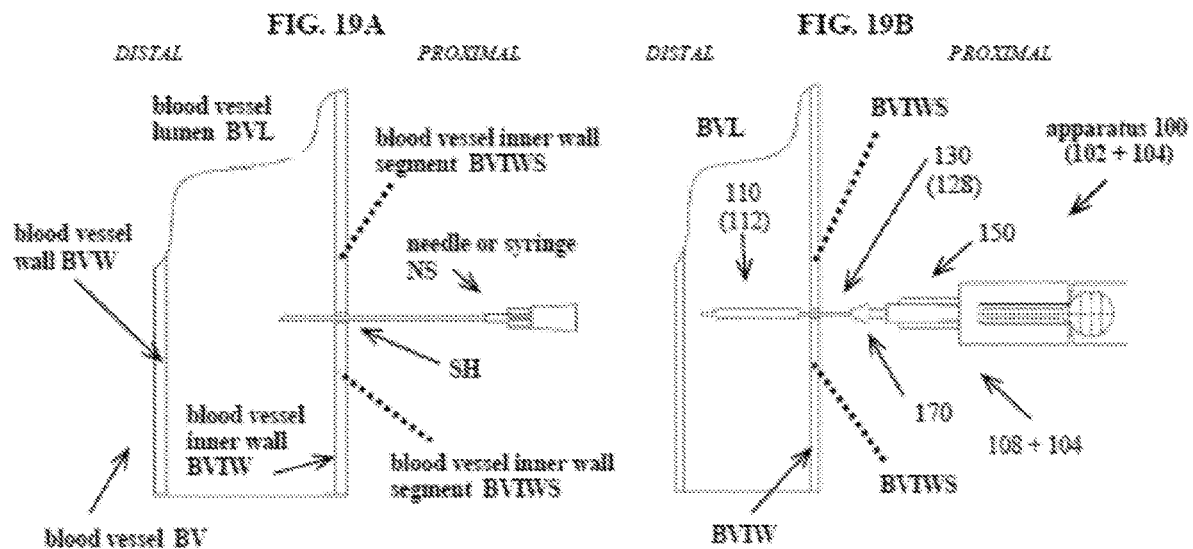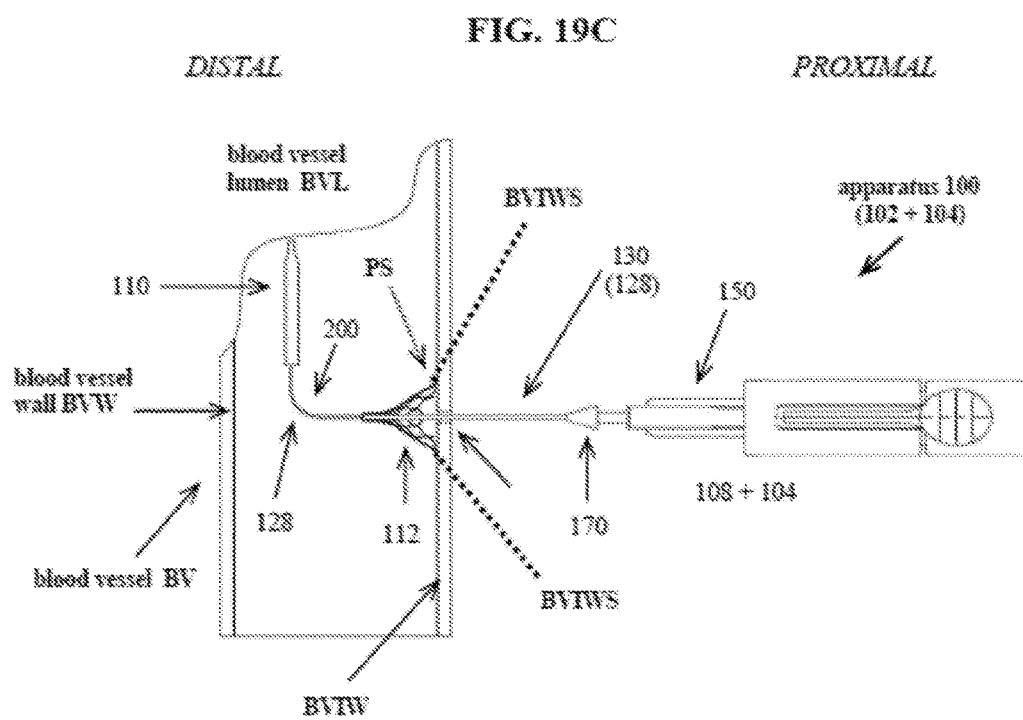

APPARATUSES AND METHODS FOR USE IN SURGICAL VASCULAR ANASTOMOTIC PROCEDURES

RELATED APPLICATION(S)

This application is a U.S. National Stage Entry under 35 U.S.C. 371 of International Application No. PCT/IB2018/053016 filed on May 1, 2018, which claims the benefit of priority under 35 USC 119(e) of U.S. Provisional Patent Application No. 62/492,323, filed on May 1, 2017 and entitled "APPARATUSES AND METHODS FOR FACILITATING ANASTOMOSIS". The contents of the above applications are incorporated herein by reference in their entirety.

FIELD OF THE INVENTION

The present invention, in some embodiments thereof, relates to surgical vascular anastomotic apparatuses and methods, and more particularly, but not exclusively, to apparatuses and methods for use in surgical vascular anastomotic procedures. Some embodiments of the present invention relate to procedures for performing surgical vascular anastomosis using the herein disclosed apparatuses and methods. Some embodiments of the present invention are particularly applicable for use in 'clampless' types of (end-to-side) surgical vascular anastomotic procedures, for performing coronary artery bypass grafting (CABG).

BACKGROUND OF THE INVENTION

Surgical vascular anastomotic (anastomosis) procedures are employed in coronary artery bypass grafting (CABG) and involve anastomotic connection of both ends of a blood vessel graft, usually a harvested vein or artery. In end-to-side type of surgical vascular anastomosis, one end of a blood vessel graft is connected (e.g., sutured) to a side of a host blood vessel. This procedure commonly involves cutting or puncturing the host blood vessel wall at the selected anastomotic location or site, then suturing the graft end around the puncture in order to create fluid (blood) communication between lumens of the two vessels.

End-to-side anastomoses in large diameter host blood vessels, especially the aorta, is highly cumbersome due to high flow rates and pressures of blood flowing therethrough. Traditional surgical vascular anastomotic procedures, with or without use of a heart bypass machine, include clamping and isolating the host blood vessel wall from the subject's blood circulation. However, such surgical vascular anastomotic procedures are typically associated with several possible significant problems. For example, possible harm to the host blood vessel, possible formation of clots adjacent to clamped areas, possible calcification formation and thrombi release from the blood vessel wall which in turn may migrate to the brain and lead to neurological damage.

More recently employed surgical vascular anastomotic procedures based on 'clampless' techniques involve use of peripheral seals for temporarily sealing around and slightly beyond the puncture in the host blood vessel wall, while maintaining blood flow in the host blood vessel. However, such procedures, particularly during anastomotic construction, may be accompanied by severe blood leakage through the puncture, which then requires the heart surgery team to perform complex, sometimes extraordinary, operational activities for peripherally sealing the puncture, in addition to and while performing the anastomosis. Blood leakage during anastomotic construction may lead to suboptimal suturing of the blood vessels, typically, by obstructing view and decreasing visibility of the suturing area. Such may then require a surgical assistant to use an air blower on the anastomotic site in order to remove (blow away) leaking blood, to thereby improve view and visibility of the suturing area. Moreover, during such a procedure, the air blower inserts air into the host blood vessel or/and the blood vessel graft, which may lead to airemboli or/and occlusion therein.

Despite extensive teachings and practices in the field of surgical vascular anastomosis, and in view of at least the above described problems associated therewith, there is an on-going need for developing and practicing new and improved apparatuses and methods for use in surgical vascular anastomotic procedures. Such need is particularly relevant to clampless types of surgical vascular anastomotic procedures employed in coronary artery bypass grafting (CABG). There is similar need for developing and practicing new and improved procedures for performing surgical vascular anastomosis using such apparatuses and methods.

SUMMARY OF THE INVENTION

The present invention, in some embodiments thereof, relates to apparatuses and methods for use in surgical vascular anastomotic procedures. Some embodiments of the present invention relate to procedures for performing surgical vascular anastomosis using the herein disclosed apparatuses and methods. Some embodiments of the present invention are particularly applicable for use in 'clampless' types of (end-to-side) surgical vascular anastomotic procedures, for performing coronary artery bypass grafting (CABG).

Implementation of the present invention attempts to address, and overcome, at least some of the various problems associated with surgical vascular anastomotic procedures, particularly, those procedures which are employed in coronary artery bypass grafting (CABG). For example, implementation of the present invention involves unique techniques (devices and methods) without need for using clamps, for atraumatically generating a peripherally sealed anastomotic hole in a blood vessel inner wall, thereby preventing or minimizing peripheral blood leakage around the anastomotic hole, while maintaining blood flow in the host blood vessel. Such improved techniques provide safer surgical conditions, and preclude or significantly reduce need for a heart surgery team to perform complex operational activities for peripherally sealing anastomotic holes in blood vessels, in addition to and while performing an anastomotic procedure.

According to an aspect of some embodiments of the present invention, there is provided an apparatus for use in surgical vascular anastomotic procedures, the apparatus comprising: a blood vessel inner wall sealing and hole forming device, configured to atraumatically establish and maintain, inside a blood vessel lumen, along an inner wall segment thereof, a peripheral seal around a needle sized hole in the blood vessel inner wall segment, absent of blood flow, and to form an anastomotic hole through the peripherally sealed blood vessel inner wall segment, in the blood flow absence; and a hole forming actuator, operably connectable to, and configured for operating, the blood vessel inner wall sealing and hole forming device.

According to an aspect of some embodiments of the present invention, there is provided a device for peripherally sealing, inside a blood vessel, a blood vessel inner wall segment thereof, the device comprising: a hole sealing device comprising: a hole sealing assembly configured to atraumatically establish, along the blood vessel inner wall segment, a peripheral seal around a needle sized hole in the blood vessel inner wall segment, so as to form a peripherally sealed blood vessel inner wall segment, absent of blood flow, the hole sealing assembly has a non-activated, collapsed configuration and an activated, self-expanded configuration; a sheath configured to externally cover, closely fit over, and hold the hole sealing assembly in the non-activated, collapsed configuration, and to atraumatically entirely, with the collapsed hole sealing assembly, enter into the blood vessel, by passing through the needle sized hole and along the blood vessel inner wall segment; a manual hole sealing controller assembly, operably connected to the sheath, and configured to operate the hole sealing assembly and the sheath; a flexible control wire, operably connected to the sheath and the manual hole sealing controller assembly, and configured to operate the sheath; and a flexible tube, configured to hold and guide motion of the flexible control wire.

According to an aspect of some embodiments of the present invention, there is provided a device for peripherally sealing a blood vessel inner wall segment, the device comprising: a skeletal frame having struts, the skeletal frame is self-expandable and collapsible, the skeletal frame in a self-expanded configuration includes a middle portion having a hemispherical shape or form, and a shorter proximal end portion having an acute flare or flare-like shape or form, proximally gradually, non-linearly expanding or opening outward until proximal end of the proximal end portion; and an external covering, configured to externally fully cover the skeletal frame.

According to an aspect of some embodiments of the present invention, there is provided a device for generating an anastomotic hole in a blood vessel inner wall segment, the device comprising: an outer assembly; and an inner assembly, the outer and inner assemblies are coaxially tubular shaped along a concentric longitudinal axis thereof; the inner assembly distal end portion is configured with an anastomotic hole generating member that is configured to atraumatically pass through, via distally directed motion, a needle sized hole in the blood vessel inner wall segment, and to generate, via proximally directed motion, an anastomotic hole through the blood vessel inner wall segment, and to exit, via further proximally directed motion, the hole generated through the blood vessel inner wall segment.

According to an aspect of some embodiments of the present invention, there is provided a device for use in forming a hole in a blood vessel inner wall segment, the device comprising: an outer assembly, and an inner assembly, the outer and inner assemblies are coaxially tubular shaped along a concentric longitudinal axis thereof, the inner assembly is longer than the outer assembly; the outer assembly has a proximal end portion configured with a pair of oppositely positioned manually controllable guiding members that facilitate relative linearly translatable motion of the outer and inner assemblies; the outer assembly has a distal end portion configured with a pair of oppositely positioned manually controllable connector members; and the inner assembly has a distal end configured as a circular groove.

According to an aspect of some embodiments of the present invention, there is provided a medical device kit for use in surgical vascular anastomotic procedures, the medical kit comprising: a blood vessel inner wall sealing and hole forming device, configured to atraumatically establish and maintain, inside a blood vessel lumen, along an inner wall segment thereof, a peripheral seal around a needle sized hole in the blood vessel inner wall segment, absent of blood flow, and to form an anastomotic hole through the peripherally sealed blood vessel inner wall segment, in the blood flow absence.

According to some embodiments of the invention, the medical device kit further comprises a hole forming actuator, operably connectable to, and configured for operating, the blood vessel inner wall sealing and hole forming device.

According to an aspect of some embodiments of the present invention, there is provided a medical device kit for use in surgical vascular anastomotic procedures, the medical kit comprising: a blood vessel inner wall sealing and hole forming device, configured to atraumatically establish and maintain, inside a blood vessel lumen, along an inner wall segment thereof, a peripheral seal around a needle sized hole in the blood vessel inner wall segment, absent of blood flow, and to form an anastomotic hole through the peripherally sealed blood vessel inner wall segment, in the blood flow absence; a hole forming actuator, operably connectable to, and configured for operating, the blood vessel inner wall sealing and hole forming device; and an anastomotic hole generating device configured to generate an anastomotic hole in a blood vessel inner wall segment.

According to an aspect of some embodiments of the present invention, there is provided a method for use in surgical vascular anastomotic procedures, the method comprising: providing an apparatus for use in a surgical vascular anastomotic procedure, the apparatus comprising: a blood vessel inner wall sealing and hole forming device, configured to atraumatically establish and maintain, inside a blood vessel lumen, along an inner wall segment thereof, a peripheral seal around a needle sized hole in the blood vessel inner wall segment, absent of blood flow, and to form an anastomotic hole through the peripherally sealed blood vessel inner wall segment, in the blood flow absence; and a hole forming actuator, operably connectable to, and configured for operating, the blood vessel inner wall sealing and hole forming device; and operating the apparatus for establishing, and maintaining, the peripheral seal, before, during, and after, generating the anastomotic hole through the peripherally sealed blood vessel inner wall segment, in the blood flow absence.

According to an aspect of some embodiments of the present invention, there is provided a method for forming an anastomotic hole in a blood vessel inner wall segment, the method comprising: providing a device comprising: an outer assembly; and an inner assembly, the outer and inner assemblies are coaxially tubular shaped along a concentric longitudinal axis thereof; the inner assembly distal end portion is configured with an anastomotic hole generating member that is configured to atraumatically pass through, via distally directed motion, a needle sized hole in the blood vessel inner wall segment, and to generate, via proximally directed motion, an anastomotic hole through the blood vessel inner wall segment, and to exit, via further proximally directed motion, the hole generated through the blood vessel inner wall segment; and operating the device, so as to generate the anastomotic hole in the blood vessel inner wall segment.

According to an aspect of some embodiments of the present invention, there is provided a method for performing surgical vascular anastomosis, the method comprising: providing an apparatus for use in a surgical vascular anastomotic procedure, the apparatus comprising: a blood vessel inner wall sealing and hole forming device, configured to atraumatically establish and maintain, inside a blood vessel lumen, along an inner wall segment thereof, a peripheral seal around a needle sized hole in the blood vessel inner wall segment, absent of blood flow, and to form an anastomotic hole through the peripherally sealed blood vessel inner wall segment, in the blood flow absence; and a hole forming actuator, operably connectable to, and configured for operating, the blood vessel inner wall sealing and hole forming device; operating the apparatus for establishing, and maintaining, the peripheral seal, before, during, and after, generating the anastomotic hole through the peripherally sealed blood vessel inner wall segment, in the blood flow absence; and performing anastomosis of a blood vessel graft on a blood vessel, following the operating of the apparatus.

All technical or/and scientific words, terms, or/and phrases, used herein have the same or similar meaning as commonly understood by one of ordinary skill in the art to which the invention pertains, unless otherwise specifically defined or stated herein. Exemplary embodiments of methods (steps, procedures), apparatuses (devices, systems, components thereof), equipment, and materials, illustratively described herein are exemplary and illustrative only and are not intended to be necessarily limiting. Although methods, apparatuses, equipment, and materials, equivalent or similar to those described herein can be used in practicing or/and testing embodiments of the invention, exemplary methods, apparatuses, equipment, and materials, are illustratively described below. In case of conflict, the patent specification, including definitions, will control.

BRIEF DESCRIPTION OF THE SEVERAL VIEWS OF THE DRAWINGS

Some embodiments of the present invention are herein described, by way of example only, with reference to the accompanying drawings. With specific reference now to the drawings in detail, it is stressed that the particulars shown are by way of example and for purposes of illustrative description of some embodiments of the present invention. In this regard, the description taken together with the accompanying drawings make apparent to those skilled in the art how some embodiments of the present invention may be practiced.

In the drawings:

FIG. 6 is a schematic side view of an exemplary embodiment of the (overall) apparatus proximal end portion, highlighting components and structural/functional features of the manual hole sealing controller assembly of the hole sealing device, in accordance with some embodiments of the invention;

FIG. 7 is a schematic side view of an exemplary embodiment of the (overall) apparatus proximal end portion, highlighting components and structural/functional features of another exemplary manual controller of the hole sealing device, in accordance with some embodiments of the invention;

FIG. 11A is a schematic top view of an exemplary embodiment of the hole forming actuator, highlighting outer and inner assemblies thereof in an assembled (non-activated/non-actuated) configuration, in accordance with some embodiments of the invention;

FIG. 11B is a schematic side view of an exemplary embodiment of the hole forming actuator, highlighting outer and inner assemblies thereof in an assembled configuration, also showing non-activated (non-actuated) and activated (actuated) configurations, respectively, thereof, in accordance with some embodiments of the invention;

FIG. 17 is a schematic perspective view of an exemplary embodiment of a medical device kit, including (i) the hole sealing device, (ii) the anastomotic hole generating device, and, optionally, also including (iii) the hole forming actuator (non-connected to the anastomotic hole generating device), in accordance with some embodiments of the invention;

FIG. 18 is a schematic perspective view of an exemplary embodiment of a medical device kit, including (i) the hole sealing device, (ii) the anastomotic hole generating device, and (iii) the hole forming actuator (connected to the anastomotic hole generating device), in accordance with some embodiments of the invention; and FIGS. 19A-19K are schematic views of exemplary embodiments of sequential steps (procedures) of implementing the apparatus (and components thereof) for use in surgical vascular anastomotic procedures, in accordance with some embodiments of the invention.

DESCRIPTION OF SPECIFIC EMBODIMENTS OF THE INVENTION

Figure 1:
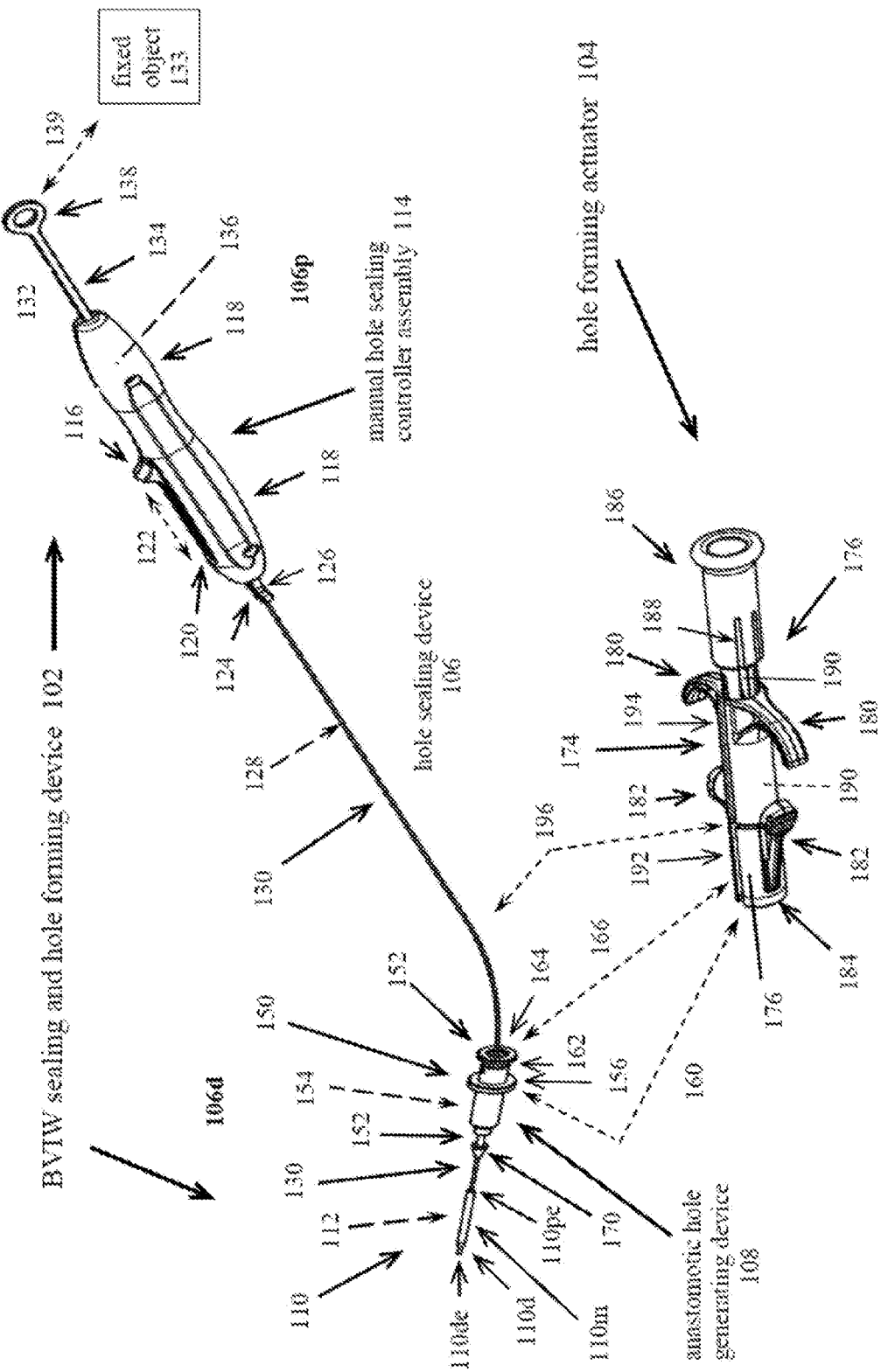
FIGS. 1 and 2 are schematic perspective views of an exemplary embodiment of the (overall) apparatus, including: the blood vessel inner wall (BVIW) sealing and hole forming device, and the hole forming actuator, in exemplary non-activated and activated configurations, respectively, for use in surgical vascular anastomotic procedures, in accordance with some embodiments of the invention.

The present invention, in some embodiments thereof, relates to apparatuses and methods for use in surgical vascular anastomotic procedures. Some embodiments of the present invention relate to procedures for performing surgical vascular anastomosis using the herein disclosed apparatuses and methods. Some embodiments of the present invention are particularly applicable for use in 'clampless' types of (end-to-side) surgical vascular anastomotic procedures, for performing coronary artery bypass grafting (CABG).

Implementation of the present invention attempts to address, and overcome, at least some of the various problems associated with surgical vascular anastomotic procedures, particularly, those procedures which are employed in coronary artery bypass grafting (CABG). For example, implementation of the present invention involves unique techniques (devices and methods) without need for using clamps, for atraumatically generating a peripherally sealed anastomotic hole in a blood vessel inner wall, thereby preventing or minimizing peripheral blood leakage around the anastomotic hole, while maintaining blood flow in the host blood vessel. Such improved techniques provide safer surgical conditions, and preclude or significantly reduce need for a heart surgery team to perform complex operational activities for peripherally sealing anastomotic holes in blood vessels, in addition to and while performing an anastomotic procedure.

For purposes of further understanding exemplary embodiments of the present invention, in the following illustrative description thereof, reference is made to the figures (FIGS. 1 through 19). Throughout the following description and accompanying drawings, same reference numbers refer to same apparatus components, elements, or features. Additionally, throughout the description the standard terms "proximal" and "distal" are used for indicating relative locations and directions. For clarity and consistency, these same terms also appear in each of the drawings. Exemplary materials of construction and size dimensions of components of the herein disclosed apparatus (and components thereof) are separately provided toward the end of the Description, so as to preserve clarity of presentation of the disclosed invention.

It is to be understood that the invention is not necessarily limited in its application to particular details of construction or/and arrangement of exemplary apparatus or/and device components, or to any particular sequential ordering of exemplary method steps or procedures, set forth in the following illustrative description. Additionally, the invention is not necessarily limited in its application for use in surgical vascular anastomotic procedures. The invention is capable of other exemplary embodiments, and of being practiced or carried out in various ways, in various medical applications.

The present invention, in exemplary embodiments thereof, includes (at least) the following aspects. An apparatus for use in surgical vascular anastomotic procedures. A device for sealing a blood vessel inner wall segment and forming a hole therein. A device for peripherally sealing a blood vessel inner wall segment. A device for generating an anastomotic hole in a blood vessel inner wall segment. A device for use in forming a hole in a blood vessel inner wall segment. A medical device kit for use in surgical vascular anastomotic procedures. A method for use in surgical vascular anastomotic procedures. A method for forming an anastomotic hole in a blood vessel inner wall segment. A method for performing surgical vascular anastomosis.

The several aspects of the present invention, in a non-limiting manner, are interrelated, in that illustrative description of characteristics and technical features of one aspect also relates to, and is fully applicable for, illustratively describing characteristics and technical features of other aspects of the present invention. For example, illustrative description of characteristics and technical features of the apparatus for use in surgical vascular anastomotic procedures, or of a component (e.g., device, assembly) of the apparatus, also relates to, and is fully applicable for, illustratively describing characteristics and technical features of one or more other aspects of the present invention, for example, one or more aspects about a method for use in surgical vascular anastomotic procedures, or/and about a method for forming an anastomotic hole in a blood vessel inner wall segment, or/and about a method for performing surgical vascular anastomosis.

Additionally, for example, in a non-limiting manner, embodiments of the apparatus for use in surgical vascular anastomotic procedures, or of a component (e.g., device, assembly) of the apparatus, are suitable for implementing embodiments of a method for use in surgical vascular anastomotic procedures, or/and for implementing embodiments of a method for forming an anastomotic hole in a blood vessel inner wall segment, or/and for implementing embodiments of a method for performing surgical vascular anastomosis.

The apparatus for use in surgical vascular anastomotic procedures, in a non-limiting manner, and in some embodiments, includes: a blood vessel inner wall (BVIW) sealing and hole forming device (herein, for brevity, also referred to as the BVIW sealing and hole forming device), and a hole forming actuator.

In exemplary embodiments, the blood vessel inner wall (BVIW) sealing and hole forming device includes: a hole sealing device, and an anastomotic hole generating device.

In exemplary embodiments, the hole sealing device includes: a sheath that fully encloses and holds a hole sealing assembly, a manual hole sealing controller assembly, and also includes a flexible control wire that is enclosed within and held by a flexible tube.

In exemplary embodiments, the anastomotic hole generating device includes: an outer assembly, and an inner assembly, along with an anastomotic hole generating member.

In exemplary embodiments, the hole forming actuator includes: an outer assembly, and an inner assembly.

Above listed devices, assemblies, and members, in turn, include various assemblies, members, and structural features.

In exemplary embodiments, several components (i.e., devices, assemblies, members, and components thereof) of the apparatus for use in surgical vascular anastomotic procedures, in a non-limiting manner, may be considered as individual 'stand-alone' apparatuses, particularly, based on their structural and functional/operational characteristics and features, and also based on the manner in which they are illustratively described herein. Such individual 'stand-alone' (structural and functional/operational) apparatuses correspond to various 'sub-combinations' of the (overall) apparatus for use in surgical vascular anastomotic procedures.

For example, in exemplary embodiments, the BVIW sealing and hole forming device, and components thereof, may be considered as an individual 'stand-alone' apparatus. For example, in exemplary embodiments, the hole sealing device, the sheath, the hole sealing assembly, the manual hole sealing controller assembly, and the anastomotic hole generating device, may each be considered as an individual 'stand-alone' apparatus. Additionally, for example, the anastomotic hole generating member may also be considered as an individual 'stand-alone' apparatus.

For example, in exemplary embodiments, the hole forming actuator may also be considered as an individual 'stand-alone' apparatus.

Accordingly, each one of such individual 'stand-alone' (structural and functional/operational) apparatuses corresponds to an exemplary particular 'sub-combination' of the (overall) apparatus for use in surgical vascular anastomotic procedures, which, in turn, corresponds to another aspect of some embodiments of the present invention.

Figure 2:
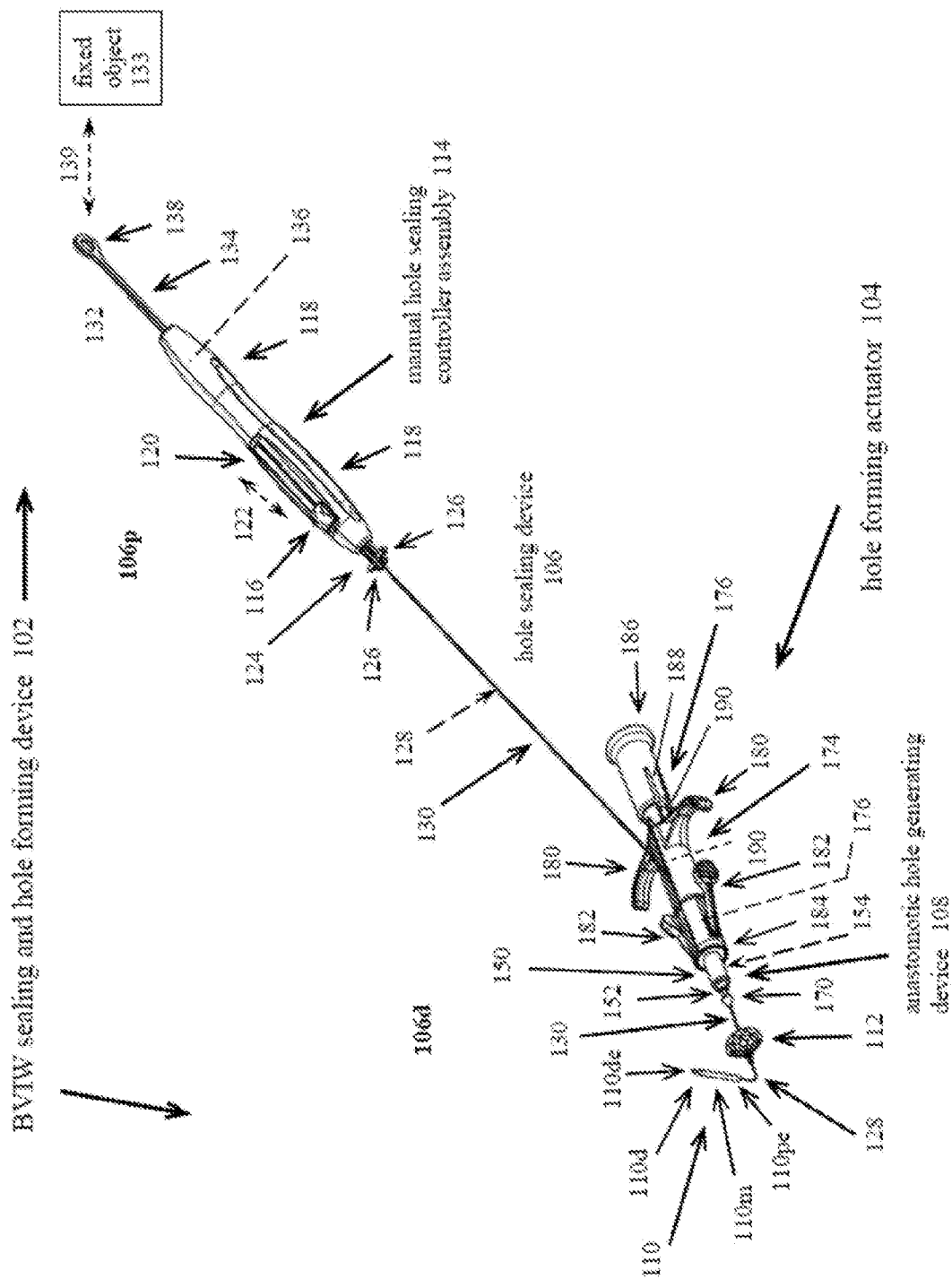

Referring now to the drawings, FIGS. 1 and 2 are schematic perspective views of an exemplary embodiment of the (overall) apparatus (indicated as, and referred to by, reference number 100), including: blood vessel inner wall (BVIW) sealing and hole forming device 102, and hole forming actuator 104, in exemplary non-activated and activated configurations, respectively, for use in surgical vascular anastomotic procedures. FIGS. 19A-19K are schematic views of exemplary embodiments of sequential steps (procedures) of implementing the apparatus 100 (and components thereof) for use in surgical vascular anastomotic procedures.

The terms "non-activated", and "partially activated", are used herein for the purpose of assisting one to clearly understand structural and functional (operational) characteristics and features of the various aspects of the disclosed invention, including the numerous components of the disclosed apparatuses and the numerous steps (procedures) of the disclosed methods.

The term "non-activated", as used herein, in a non-limiting manner, refers to the (overall) apparatus having components being, or having a configuration that is, not [yet] 'active' (i.e., not [yet] activated, not [yet] actuated, not [yet] set in motion). Such components of the (overall) apparatus being, or having a configuration that is, not 'active' (i.e., not activated, not actuated, not set in motion), have full potential and capability for becoming, or for having a configuration that becomes, 'active' (i.e., activated, actuated, set in motion), for performing all the illustratively described functions (operations) thereof, for example, when the apparatus (and components thereof) is deployed for use in a surgical vascular anastomotic procedure.

The term "partially activated", as used herein, in a non-limiting manner, refers to the (overall) apparatus having some components (or components thereof) being, or having a configuration that is, 'active' (i.e., activated, actuated, set in motion), while some other components (or components thereof) of the (overall) apparatus are, or have a configuration that is, not [yet] 'active' (i.e., not [yet] activated, not [yet] actuated, not [yet] set in motion). Such 'non-active' components have full potential and capability for becoming, or for having a configuration that becomes, 'active' (i.e., activated, actuated, set in motion), for performing all the illustratively described functions (operations) thereof, for example, when the apparatus (and components thereof) is deployed for use in a surgical vascular anastomotic procedure.

Blood Vessel Inner Wall (BVIW) Sealing and Hole Forming Device

Figure 19D:
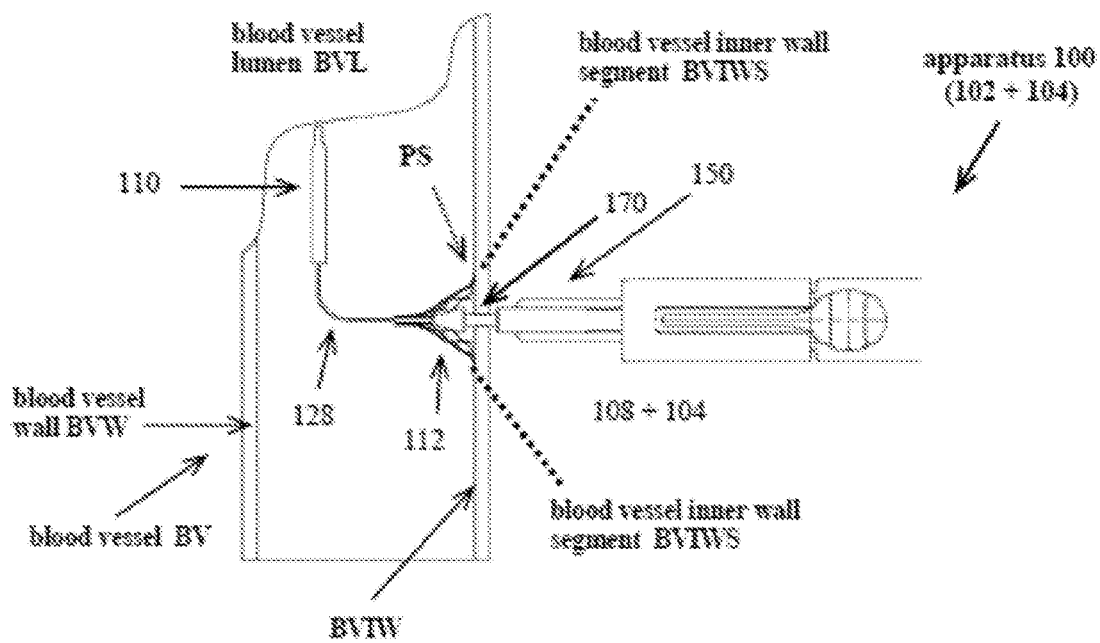
Figure 19E:
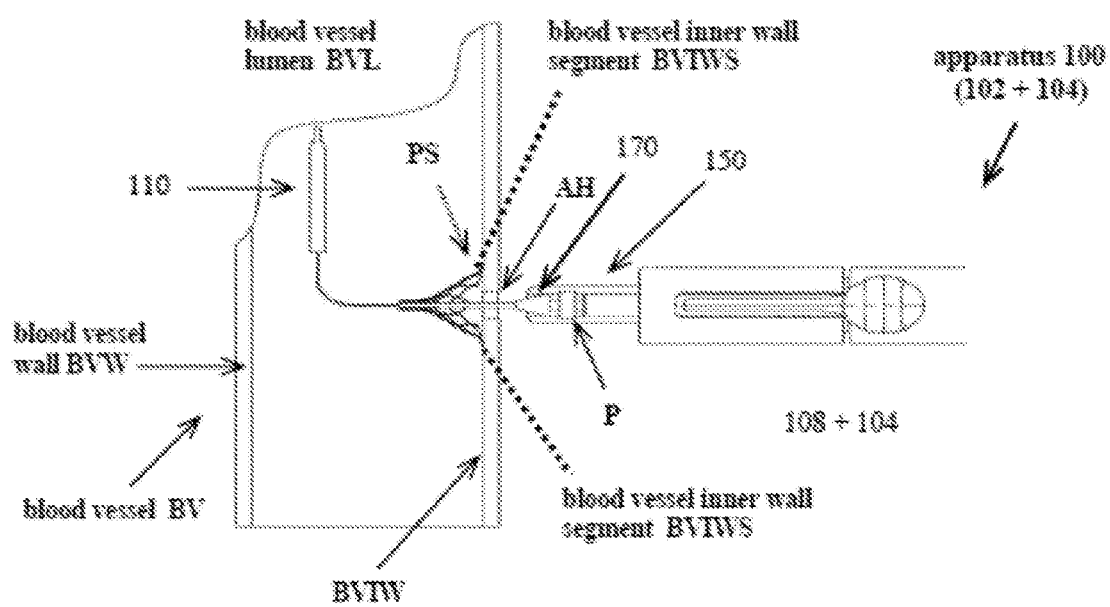
Figure 19F:
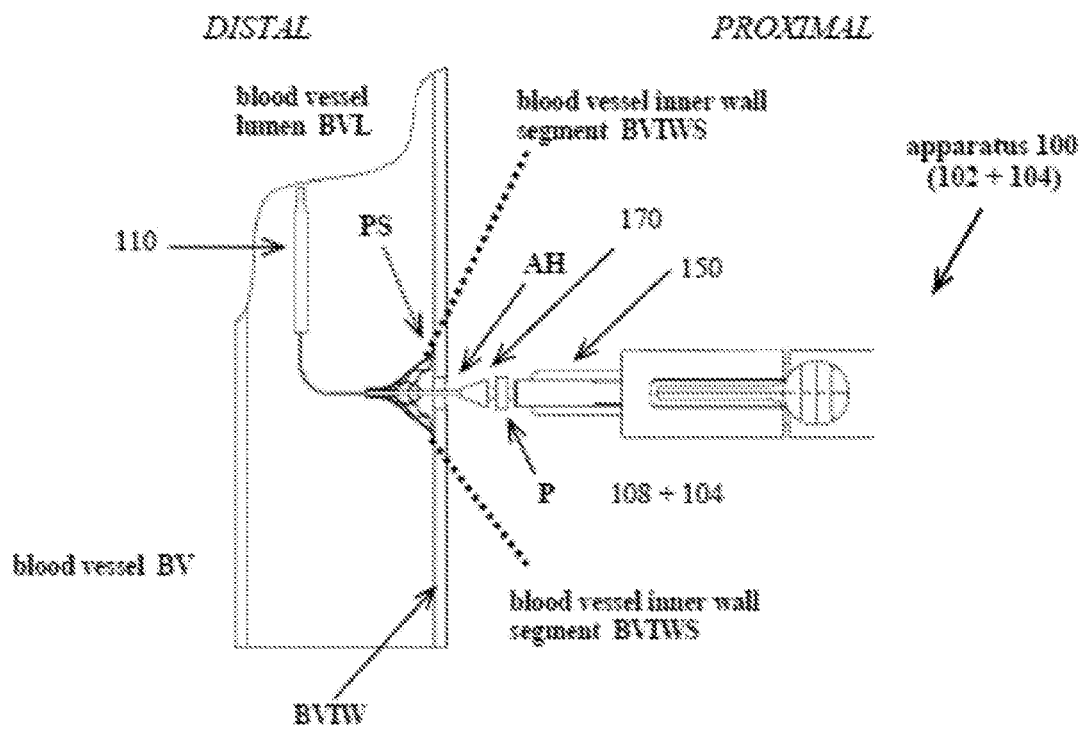
Figure 19G:
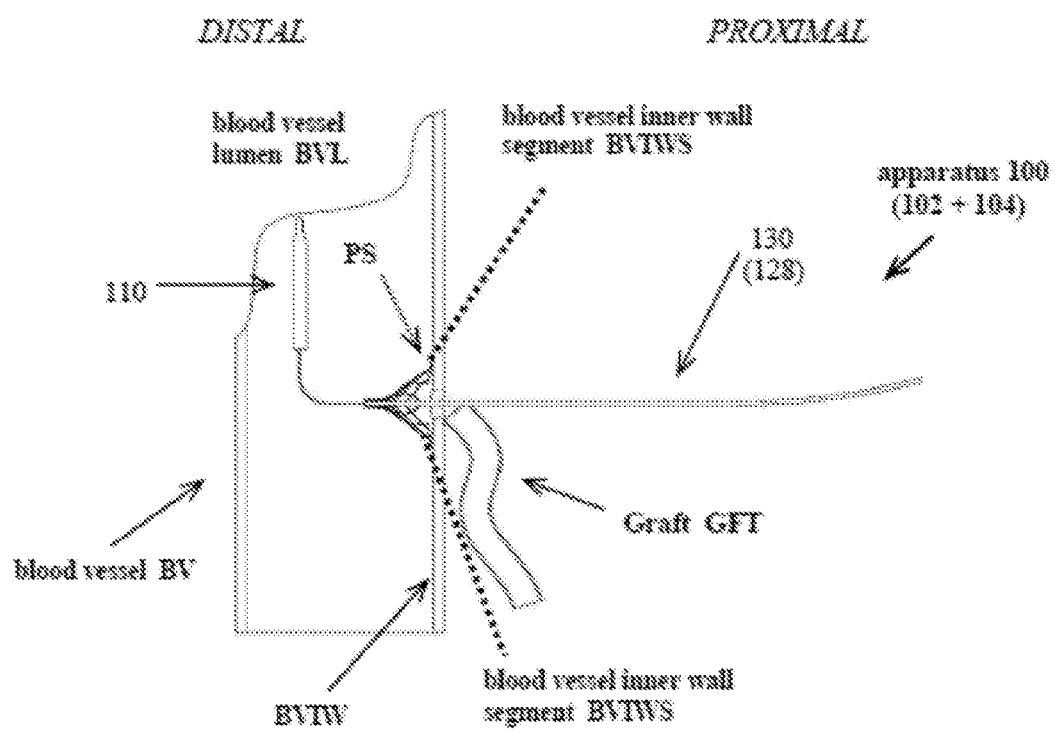

Blood vessel inner wall (BVIW) sealing and hole forming device 102 (hereinafter, for brevity, also referred to as BVIW sealing and hole forming device 102) is configured: (i) to atraumatically establish, inside a blood vessel lumen, along an inner wall segment thereof, a peripheral seal around a small hole [i.e., not incision] made (for example, manually, using a needle or syringe or syringe) in the blood vessel inner wall segment, so as to form a peripherally sealed blood vessel inner wall segment, absent of blood flow (for example, as shown in FIGS. 5B, and 19C-19D); (ii) to maintain the peripherally sealed blood vessel inner wall segment, in the blood flow absence; and (iii) to form (generate) an anastomotic hole through the peripherally sealed blood vessel inner wall segment, in the blood flow absence (for example, as shown in FIGS. 19E-19G). BVIW sealing and hole forming device 102 includes: a hole sealing device 106 (also referenced as 106$d$+106$p$, in FIGS. 1 and 2, and in subsequent figures), and an anastomotic hole generating device 108.

For example, to provide an approximate reference point or guide line of the order of magnitude of some of the relative sizes (diameters) involved, for an exemplary blood vessel being an aorta selected for deploying apparatus 100 for use in a surgical vascular anastomotic procedure (e.g., an end-to-side type of surgical vascular anastomotic procedure), an exemplary small hole has a diameter of about 0.8-1.0 millimeter (mm), made, for example, manually, using a needle or syringe or syringe of the same diameter. In such an example, the peripheral seal around the blood vessel inner wall segment has a diameter of about 14-16 millimeters (mm), and the anastomotic hole formed (generated) through the peripherally sealed blood vessel inner wall segment, in the blood flow absence, has a diameter of about 4-5 millimeters (mm). Accordingly, the diameter (about 14-16 mm) of the peripheral seal around the blood vessel inner wall segment is about three to four times the diameter (about 4-5 mm) of the anastomotic hole formed (generated) through the peripherally sealed blood vessel inner wall segment.

Hole Sealing Device

Hole sealing device 106, being a main component of BVIW sealing and hole forming device 102, is configured to peripherally seal, inside a blood vessel lumen, a blood vessel inner wall segment, from blood flow, so as to form, inside the blood vessel lumen, a peripherally sealed blood vessel inner wall segment, absent of blood flow.

Hole sealing device 106 includes: a sheath 110, a hole sealing assembly 112, a manual hole sealing controller assembly 114, a flexible control wire 128, and a flexible tube 130.

As shown in FIGS. 1 and 2, hole sealing device 106 includes a distal portion 106d and a proximal portion 106p, which, together, include and encompass sheath 110, hole sealing assembly 112, manual hole sealing controller assembly 114, flexible control wire 128, and flexible tube 130. FIG. 2 also shows anastomotic hole generating device 108 at hole sealing device distal portion 106d, via anastomotic hole generating device 108 being positioned (mounted) on flexible tube 130 at the distal portion 106d of hole sealing device 106.

Sheath, and Hole Sealing Assembly

Hole sealing device distal portion 106d includes a sheath (covering or case) 110 that fully encloses and holds hole sealing assembly 112 in a non-activated, collapsed configuration. Hole sealing assembly 112 in a non-activated, collapsed configuration is present inside sheath 110, as indicated by the dashed line arrow of reference number 112, but, is not visible in FIG. 1. Exemplary embodiments of hole sealing assembly 112 in an activated, self-expanded configuration are shown in FIGS. 2, 3, 5A, 5B, and 8A, and further described hereinbelow.

Sheath 110 is configured: (i) to externally cover, closely fit over, fully enclose, and hold hole sealing assembly 112 in a non-activated, collapsed configuration; and (ii) to atraumatically entirely (with the collapsed hole sealing assembly 112) enter into a blood vessel lumen, by passing through a small hole [i.e., not incision] (previously) made (for example, by a medical practitioner using a needle or syringe or syringe) through a blood vessel wall and along a blood vessel inner wall segment thereof (FIGS. 4B, and 19A-19B).

In exemplary embodiments, sheath 110 is configured as a tubular member having a main portion 110m whose proximal end 110pe is opened, and a conical (i.e., cone or conical shaped) distal end portion 110d whose distal end (i.e., tapered point or apex) 110de is closed. In such exemplary embodiments, conical distal end 110de of sheath 110 has a maximum outer diameter that is less than the outer diameter of main portion 110m of sheath 110. In exemplary embodiments, sheath conical distal end 110de has a maximum outer diameter that is less than the diameter of the small hole (previously) made through the blood vessel wall and along the blood vessel inner wall segment thereof.

The inside of sheath distal end portion 110d, for example, at distal end 110de thereof, is fixedly connected to the distal end of a flexible control wire 128 that controls motion and positioning of sheath 110 and activation (actuation) of hole sealing assembly 112. For hole sealing assembly 112 in a non-activated, collapsed configuration (FIG. 1), a flexible tube 130 (enclosing and holding flexible control wire 128), proximally emerges from sheath opened proximal end 110pe. For hole sealing assembly 112 in an activated, self-expanded configuration (FIG. 2), flexible control wire 128 (being distally moved out of flexible tube 130) proximally emerges from sheath opened proximal end 110pe.

Sheath conical distal end portion 110d (with closed distal end [tapered point or apex] 110de) is highly effective for performing above (ii), namely, to atraumatically entirely (with the collapsed hole sealing assembly 112) enter into a blood vessel lumen, by passing through a small (needle or syringe or sized) hole made through a blood vessel wall and along a blood vessel inner wall segment thereof. For example, for performing an end-to-side CABG surgical vascular anastomotic procedure, a small hole [i.e., not incision] is made, through the aorta wall, using a needle or syringe or syringe having a diameter in a range of between about 0.8 millimeter (mm) and 1.0 millimeter (mm), resulting in the small hole having a similar diameter. An exemplary sheath 110 has a main portion 110m whose outer diameter is about 2 millimeters (mm), and a conical distal end 110de having an outer diameter of about 0.6 millimeter (mm), being smaller than the diameter of each of sheath main portion 110m (2 mm) and the small (needle or syringe sized) hole (0.8-1.0 mm). Accordingly, via proximal to distal (pushing) motion of flexible control wire 128, sheath conical distal end 110de (having diameter of about 0.6 mm) readily passes through the small (needle or syringe sized) hole (having diameter of about 0.8-1.0 mm), so as to facilitate, in an atraumatic manner, entry of sheath main portion 110m (having diameter of about 2 mm) into the aorta lumen.

Hole sealing assembly 112 is configured: (i) to atraumatically establish, inside a blood vessel lumen, along an inner wall segment thereof, a peripheral seal around a small hole [i.e., not incision] [i.e., not incision] made (for example, by a needle or syringe) in the blood vessel inner wall segment, so as to form a peripherally sealed blood vessel inner wall segment, absent of blood flow (for example, as shown in FIGS. 5B, and 19C-19D); and (ii) to maintain the peripherally sealed blood vessel inner wall segment, in the blood flow absence (for example, as shown in FIGS. 19E-19G).

Hole sealing assembly 112 atraumatically maintains the peripherally sealed blood vessel inner wall segment, in the blood flow absence, before, during, and after, BVIW sealing and hole forming device 102 (via hole generating device 106 and anastomotic hole generating device 108) form (generate) an anastomotic hole (e.g., having a diameter of about 4-5 millimeter (mm)) through the peripherally sealed blood vessel inner wall segment, in the blood flow absence. Such structural and functional characteristics and features of hole sealing assembly 112 provide a highly desirable atraumatic 'blood flow free' local environment peripherally surrounding the blood vessel inner wall segment, inside the blood vessel lumen of the selected blood vessel, for performing a surgical vascular anastomosis procedure.

In exemplary embodiments, hole sealing assembly 112 is reversibly collapsible and self-expandable (i.e., collapsible, self-expandable, re-collapsible, etc.), along with having corresponding collapsed and self-expanded configurations. Hole sealing assembly 112 is made of flexible and elastic materials (e.g., flexible and elastic metals, plastics, synthetic polymers, composites, or/and similar type materials) that provide the self-expandable and collapsible characteristics to hole sealing assembly 112. Hole sealing assembly 112 has a non-activated, collapsed configuration similar to that of a closed (collapsed) umbrella top. Hole sealing assembly 112 has an activated, self-expanded configuration similar to that of an opened (expanded) umbrella top. Hole sealing assembly 112 is configured to be self-expandable, from the non-activated, collapsed configuration to the activated, self-expanded configuration. Specifically, hole sealing assembly 112 is confined to a collapsed configuration by being enclosed within and held by sheath 110. Upon removal of sheath 110 from around hole sealing assembly 112, hole sealing assembly 112 self-expands to a self-expanded configuration.

Hole sealing assembly 112, in each of a non-activated, collapsed configuration, and an activated, self-expanded configuration, has a (relatively short) distal end portion (neck or apex) having a tubular shape or form (i.e., a neck or throat like end portion). In such exemplary embodiments, the tubular shape or form of the distal end portion (neck or apex) of hole sealing assembly 112 facilitates operative connection to (only) the distal end of flexible tube 130 (with flexible control wire 128 inside). Such operative connection provides flexible control wire 128 the capability of distally passing through flexible tube 130 so as to distally remove sheath 110 from hole sealing assembly 112, leading to hole sealing assembly 112 then having an activated, self-expanded configuration. Such operative connection also provides flexible control wire 128 the capability of proximally pulling back sheath 110 so as to return sheath 110 back onto hole sealing assembly 112, thereby, again enclosing and holding hole sealing assembly in a non-activated, collapsed configuration.

Hole sealing assembly 112, in an activated, self-expanded configuration, has an overall hemispherical (umbrella top, dome, or bell) shape or form, that is flexible and elastic. In such exemplary embodiments, hole sealing assembly 112, in an activated, self-expanded configuration, includes a (main) middle portion having a hemispherical shape or form, and a (relatively short) proximal end portion having an acute flare or flare-like shape or form (i.e., from the proximal end of the middle portion, proximally gradually, non-linearly expanding or opening outward until the proximal end of the proximal end portion). In such exemplary embodiments, hole sealing assembly (main) middle portion has a (proximal to distal) length that is greater than the (proximal to distal) length of each of hole sealing assembly distal end portion (neck or apex), and hole sealing assembly proximal end portion.

In exemplary embodiments, hole sealing assembly middle portion and proximal portion (i.e., proximally extending from the proximal end of hole sealing assembly distal end portion to hole sealing assembly proximal end are configured as a flexible and elastic skeletal (or net, mesh) type frame having struts, that is fully covered (i.e., continuously around and in between the struts) with a flexible and elastic external or outer covering.

In exemplary embodiments, the frame (with the struts) is configured to have a polygonal (e.g., triangular, square, rectangular, pentagonal, hexagonal, heptagonal, octagonal, diamond type shape, or similar) geometrical pattern. In exemplary embodiments, the frame (with the struts) includes a plurality of at least two rows, for example, three rows, of struts having such a polygonal geometrical pattern.

The frame (with the struts) provides the hemispherical and flare shapes or forms of, and structural support to, hole sealing assembly middle and proximal portions. The external or outer covering provides highly effective sealing properties to the hole sealing assembly middle and proximal portions.

Such exemplary embodiments of hole sealing assembly middle and proximal end portions facilitate physically fitting, accommodating, and activating (actuating) hole sealing assembly 112, according to different possible particular shapes or forms, and size dimensions, of different blood vessel lumens inside different blood vessels. For example, as relating to the aorta, whose lumen particular shape or form, and size dimensions, typically vary from patient to patient. Additionally, for example, the flexible shape or form of hole sealing assembly middle and proximal end portions, facilitate real-time (dynamic) self-adapting (self-adjusting, self-changing) thereof to real-time (dynamically changing) structural features of different blood vessel lumens during a surgical vascular anastomotic procedure.

For hole sealing assembly 112, in an activated, self-expanded configuration, the flexible and elastic hemispherical shape or form of the hole sealing assembly middle portion, along with the flexible and elastic flare or flare-like shape or form of the hole sealing assembly proximal end portion, are particularly relevant, and advantageous, for use in surgical vascular anastomotic procedures, including, for example, in an end-to-side type of surgical vascular anastomotic procedure. For example, for hole sealing assembly 112, in an activated, self-expanded configuration, the flexible hemispherical shape or form of hole sealing assembly middle portion, along with the flexible flare or flare-like shape or form of the hole sealing assembly proximal end portion, provide sufficient working (operating) space (volume) within the peripherally sealed blood vessel inner wall segment, in a blood flow free local environment in the blood vessel lumen, for performing a surgical vascular anastomotic procedure. The flare or flare-like shape or form of the hole sealing assembly proximal end portion also provides atraumatic (i.e., non-sharp, non-cutting, sealing) structure to that part (i.e., the circumferential proximal end of the proximal end portion) of hole sealing assembly 112 which directly contacts the periphery (perimeter) of the blood vessel inner wall segment (and tissue thereof), for establishing and maintaining the peripheral seal around the blood vessel inner wall segment.

Figure 8A:
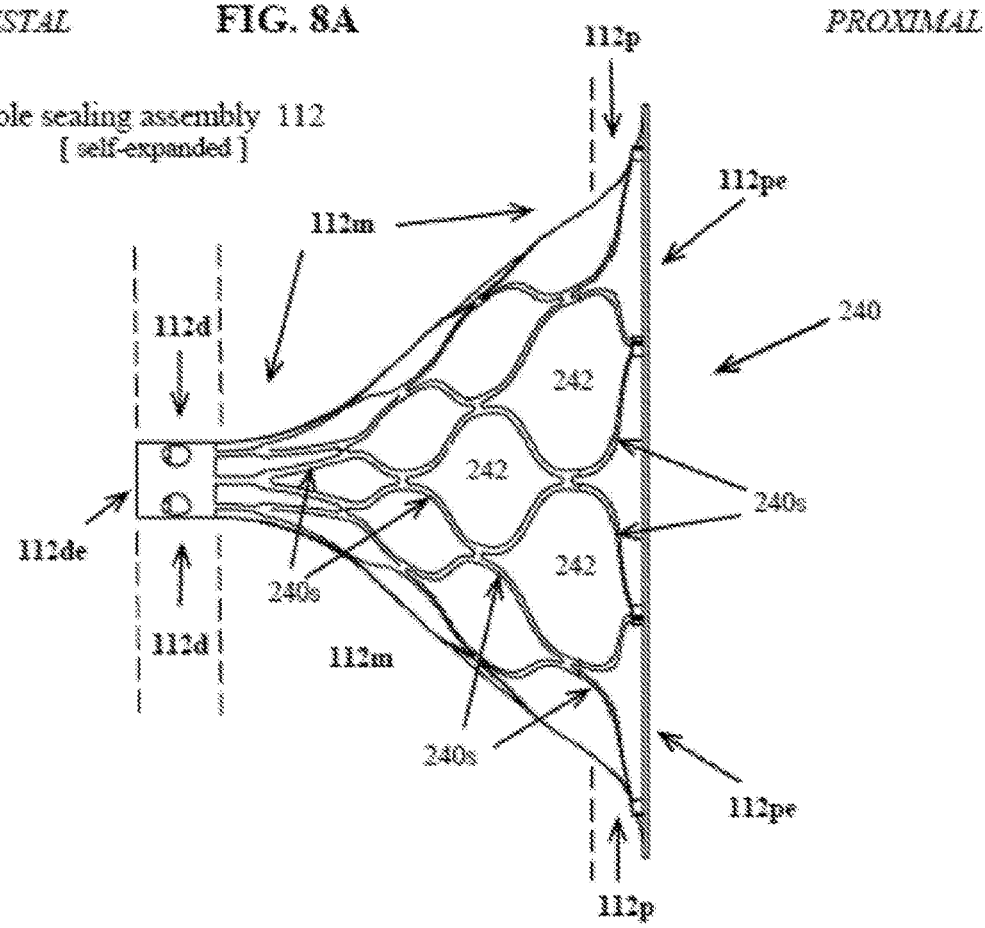
FIG. 8A is a schematic side view of an exemplary embodiment of the hole sealing assembly (part of the hole sealing device), in accordance with some embodiments of the invention.
Figure 8B:
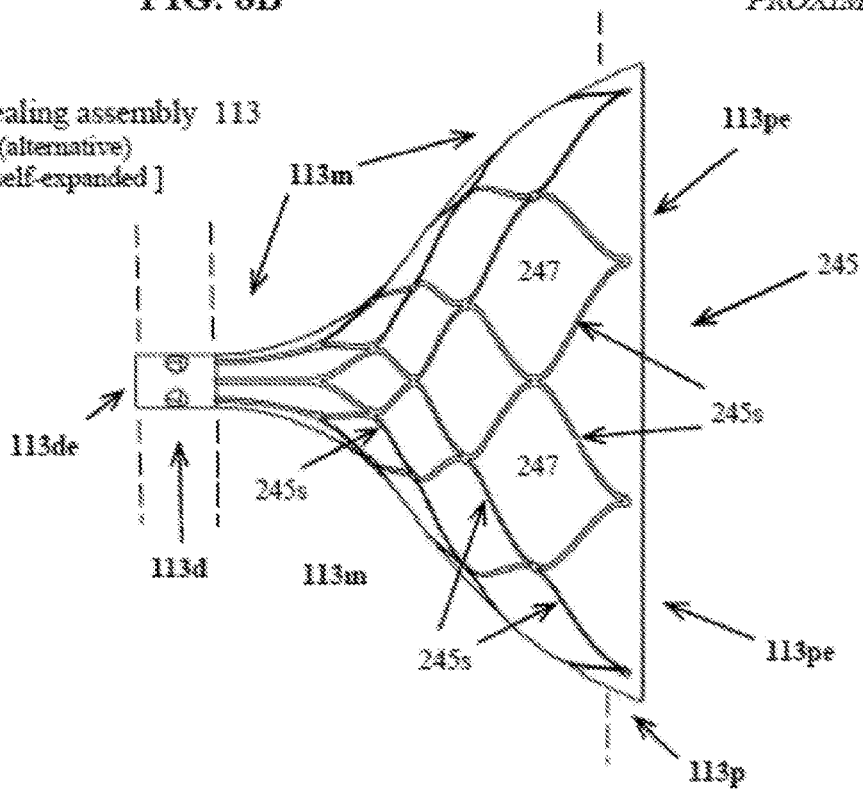
FIG. 8B is a schematic side view of an exemplary embodiment of another exemplary hole sealing assembly, in accordance with some embodiments of the invention.

An exemplary embodiment of another exemplary hole sealing assembly is shown in FIG. 8B and described below. Such an exemplary embodiment of the hole sealing assembly includes a proximal end portion absent of a flare or flare-like shape or form.

Manual Hole Sealing Controller Assembly

Hole sealing device proximal portion 106p includes a manual hole sealing controller assembly 114 that is configured to facilitate manual control (motion, positioning, actuation, operation) of part of BVIW sealing and hole forming device 102. More specifically, manual hole sealing controller assembly 114 is configured to facilitate manual control of hole sealing device distal portion 106d (including sheath 110 and hole sealing assembly 112 held therein), before, and after, use of anastomotic hole generating device 108.

Manual hole sealing controller assembly 114 is configured as a hand-holdable module that includes: a manual control knob 116, and a hand-holdable housing assembly 118. Manual control knob 116, or a similar type of structure, is configured to be manually operable and linearly translatable (manually pushable, pullable, and slidably movable forward and backward in distal and proximal directions), for example, via finger (e.g., thumb) pushing or pulling of manual control knob 116. Hand-holdable housing assembly 118 is configured with a linear slot (narrow groove or channel) 120, within and along which manual control knob 116 is so manually operable and linearly translatable, for example, as indicated in FIGS. 1 and 2 by the dashed line double-headed (bi-directional) arrow 122.

Figure 3:
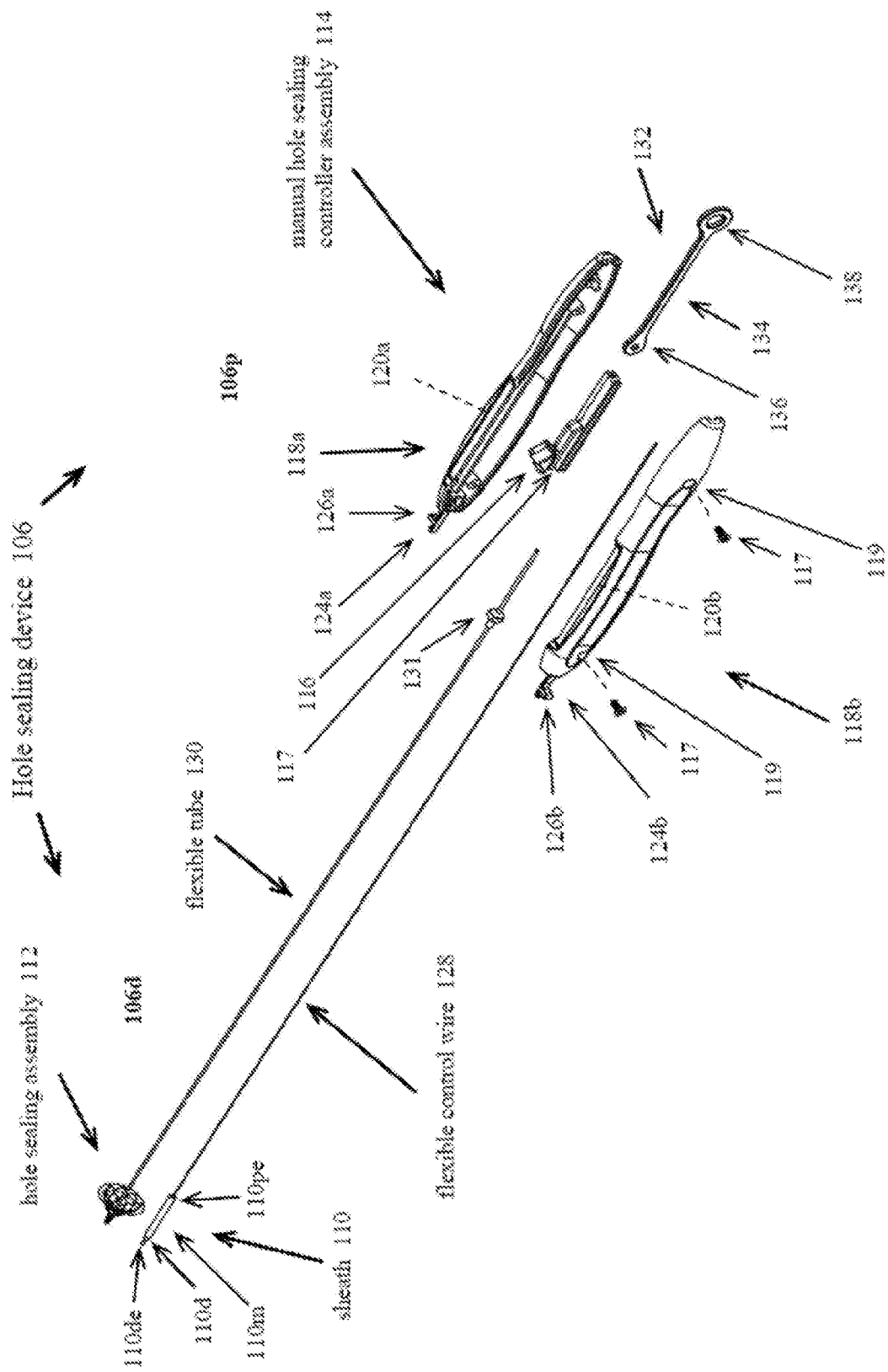
FIG. 3 is a schematic exploded perspective view of an exemplary embodiment of the hole sealing device, in accordance with some embodiments of the invention.

The distal end portion of hand-holdable housing assembly 118 includes a connecting member 124, for example, configured with a pair of oppositely (diametrically) positioned manually controllable connector members (e.g., finger pressure activated elastic fasteners or latches) 126 (more visible, for example, in FIGS. 2 and 3). Connecting member 124 is configured to facilitate manual operative reversible connection (connection, disconnection, re-connection) of the distal end of manual hole sealing controller assembly 114 with the proximal end of anastomotic hole generating device 108 (for example, via protruding rim (flange) 164 of inner assembly 152 of anastomotic hole generating device 108, as further illustratively described below).

Manual operative connection of the distal end of manual hole sealing controller assembly 114 to the proximal end of anastomotic hole generating device 108 provides a stable firm base to hole sealing device distal portion 106d (including sheath 110 and hole sealing assembly 112 held therein), for facilitating manual control (motion, positioning, actuation, operation) thereof. This includes, for example, providing a stable firm base during distally directed removal of sheath 110, via use of control wire 128, from hole sealing assembly 112, so as to facilitate self-expansion, and manually controlled positioning, of hole sealing assembly 112 along an inner wall segment in a blood vessel lumen of a selected blood vessel. This, in turn, facilitates hole sealing assembly 112 in an activated, self-expanded configuration, to accurately and atraumatically establish, inside a blood vessel lumen, along an inner wall segment thereof, a peripheral seal around a small (needle or syringe sized) hole made in the blood vessel inner wall segment, so as to form a peripherally sealed blood vessel inner wall segment, absent of blood flow (FIGS. 3B, and 19C-19D), and then, to maintain the peripherally sealed blood vessel inner wall segment, in the blood flow absence (for example, as shown in FIGS. 19E-19G).

Manual operative disconnection of the distal end of manual hole sealing controller assembly 114 from the proximal end of anastomotic hole generating device 108 is performed following successful self-expansion and manually controlled positioning of hole sealing assembly 112 along the blood vessel inner wall segment, in order to make room for subsequent operative connection of hole forming actuator 104 to anastomotic hole generating device 108, followed by subsequent activation and use of anastomotic hole generating device 108 for atraumatically generating an anastomotic hole through the peripherally sealed blood vessel inner wall segment.

Manual operative re-connection of the distal end (via connecting member 124) of manual hole sealing controller assembly 114 to the proximal end (via protruding rim (flange) 164 of inner assembly 152) of anastomotic hole generating device 108 is performed following successful generation of the anastomotic hole through the peripherally sealed blood vessel inner wall segment, and disconnection of hole forming actuator 104 from anastomotic hole generating device 108. Such disconnection is performed so as to facilitate collapsing of self-expanded hole sealing assembly 112, followed by re-inserting the collapsed configuration of hole sealing assembly 112 back into sheath 110, and eventual (proximally directed) withdrawal of sheath 110 through the blood vessel inner wall segment and out of the blood vessel.

Flexible Control Wire, and Flexible Tube

A flexible control wire 128 is configured and extends from inside manual hole sealing controller assembly 114 to inside sheath 110. Flexible control wire 128, and operation thereof, facilitate manual control (motion, positioning, actuation, operation) of hole sealing device distal portion 106d (including sheath 110 and hole sealing assembly 112 held therein). Flexible control wire 128, enclosed and held within a flexible tube 130, is present in hole sealing device 106 (in a non-activated configuration), as indicated by the dashed line arrow of reference number 128, but, is not visible in FIG. 1. Exemplary embodiments of flexible control wire 128 are shown, in an activated configuration, in FIGS. 2, 5A, and 5B; in its near entirety, in FIG. 3; and its proximal end portion, in FIGS. 6 and 7.

In exemplary embodiments, such as those shown in these figures, the proximal end portion of flexible control wire 128 is fixedly connected to manual hole sealing controller assembly 114, for example, to the inside of hand-holdable housing assembly 118, for example, via manual control knob 116. In such exemplary embodiments, the distal end of flexible control wire 128 is fixedly connected to sheath 110, for example, inside the distal end portion 110d, for example, at the distal end 110de thereof, of sheath 110.

Flexible control wire 128 is enclosed and held within, and extends along the length of, the cavity of a flexible tube 130. The proximal end of flexible tube 130 is fixedly connected to the distal portion of hand-holdable housing assembly 118, and distally extends to hole sealing device distal portion 106d. The distal end of flexible tube 130 is fixedly connected to the (inside neck or apex) distal end of hole sealing assembly 112, when hole sealing assembly is in a non-activated, collapsed configuration inside sheath 110, and also when hole sealing assembly 112 is in an activated, self-expanded configuration outside of sheath 110.

Flexible control wire 128, inside of flexible tube 130 (i.e., prior to distally removing sheath 110 from hole sealing assembly 112), via manual operation of manual hole sealing controller assembly 114, is linearly translatable (linearly pushable, pullable, and slidably movable forward and backward in distal and proximal directions) between hole sealing device proximal and distal portions 106p and 106d, respectively. In exemplary embodiments, flexible control wire 128, outside of flexible tube 130 (i.e., during and after removal of sheath 110 from hole sealing assembly 112), via manual operation of manual hole sealing controller assembly 114, is non-linearly translatable (non-linearly pushable, pullable, and slidably movable forward and backward in distal and proximal directions) between the (neck or apex) distal end of hole sealing device 112 and the proximal end (opening) of sheath 110. Such non-linear translatable movability (pushing, pulling) of a portion of flexible control wire 128, outside of flexible tube 112, is made possible, for example, by that portion of flexible control wire 128 being thermally shaped (treated) relative to the remaining portion of flexible control wire 128. For example, the distal portion of flexible control wire 128 is thermally shaped (treated) prior to completing assembly of apparatus 100, particularly, prior to assembling hole sealing device 106 thereof, more particularly, prior to placing flexible control wire 128 inside of flexible tube 130. In exemplary embodiments, the distal portion of flexible control wire 128 is thermally treated via a hot or cold type of thermal treatment, so as to provide the control wire distal portion with the preceding, and following, illustratively described structural and functional characteristics and behavior.

In exemplary embodiments, flexible tube 130 is minimally resistibly malleable or yieldable to different shapes when in a loose state, and is extendable to maintain a taut stretched form when pulled under tension, within a range of chosen tension forces, for example between 1 g and 10 Kg, optionally, between 10 g and 5 Kg, or, optionally between 100 g and 1 Kg. In exemplary embodiments, anastomotic hole generating member 170 is coupled to, and freely passable over, flexible tube 130. In exemplary embodiments, flexible tube 130 is manipulatable to a chosen orientation (e.g., via an angular orientation angle) configured for passing and guiding anastomotic hole generating device 108 (including anastomotic hole generating member 170) along flexible tube 130.

In exemplary embodiments, sheath 110, hole sealing assembly 112, flexible control wire 128, and flexible tube 130, are configured to have the following activated configurations particularly relevant for use in surgical vascular anastomotic procedures, including, for example, in an end-to-side type of surgical vascular anastomotic procedure.

In exemplary embodiments, proximal end (i.e., opening) 110pe of sheath 110 is not adjacent to, but, rather, a distance away from the (neck or apex) distal end of hole sealing assembly 112 (in an activated, self-expanded configuration). Specifically, in activated configurations, proximal end 110pe of sheath 110, via distally directed manual pushing motion of sheath 110 (via control wire 128), is distally moved off of, and positioned a distance (e.g., at least a few millimeters, and up to a few centimeters) away from, the distal end 112de of hole sealing assembly 112 (in an activated, self-expanded configuration).

In such exemplary embodiments, the proximal end 110pe of sheath 110 is distally, and non-linearly directed, via manual pushing of sheath 110 (via non-linear movement of sheath distal end 110de) by the distal end portion of control wire 128, so as to distally, and non-linearly, move off of, and be positioned a distance (e.g., from a few millimeters to a few centimeters) away from, the distal end of hole sealing assembly (in an activated, self-expanded configuration). Such activated configurations of sheath 110 and hole sealing assembly 112 facilitate control wire 128 to have an activated configuration particularly characterized by an acutely angled curvature (i.e., a curvature having, and characterized by, an acute angle) extending between the distal end of hole sealing assembly 112 and the proximal end 110pe of sheath 110, for example, as follows.

Figure 5A:
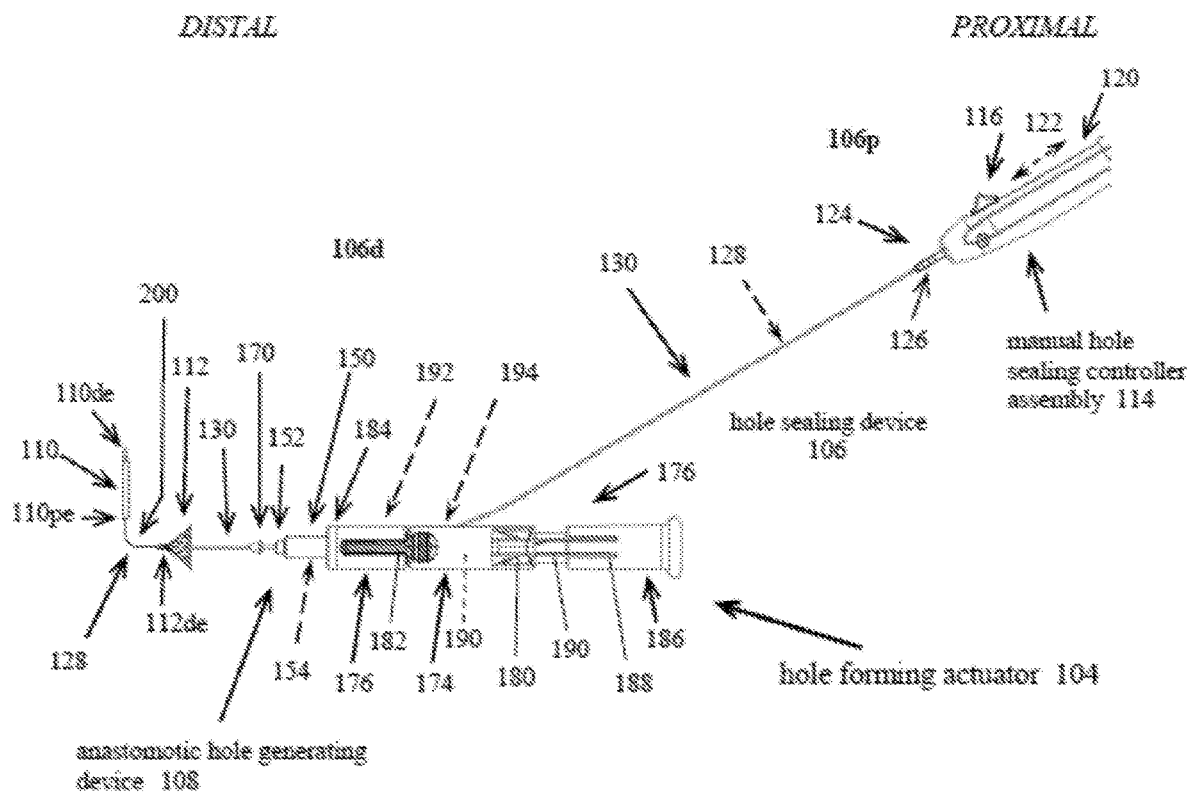
FIGS. 5A-5B are schematic side views of exemplary embodiments of the (overall) apparatus (in an activated configuration), further highlighting curvature formation of flexible control wire distal portion in a blood vessel lumen, via non-linear distally directed removal and separation of the sheath from the hole sealing assembly, in accordance with some embodiments of the invention.
Figure 5B:
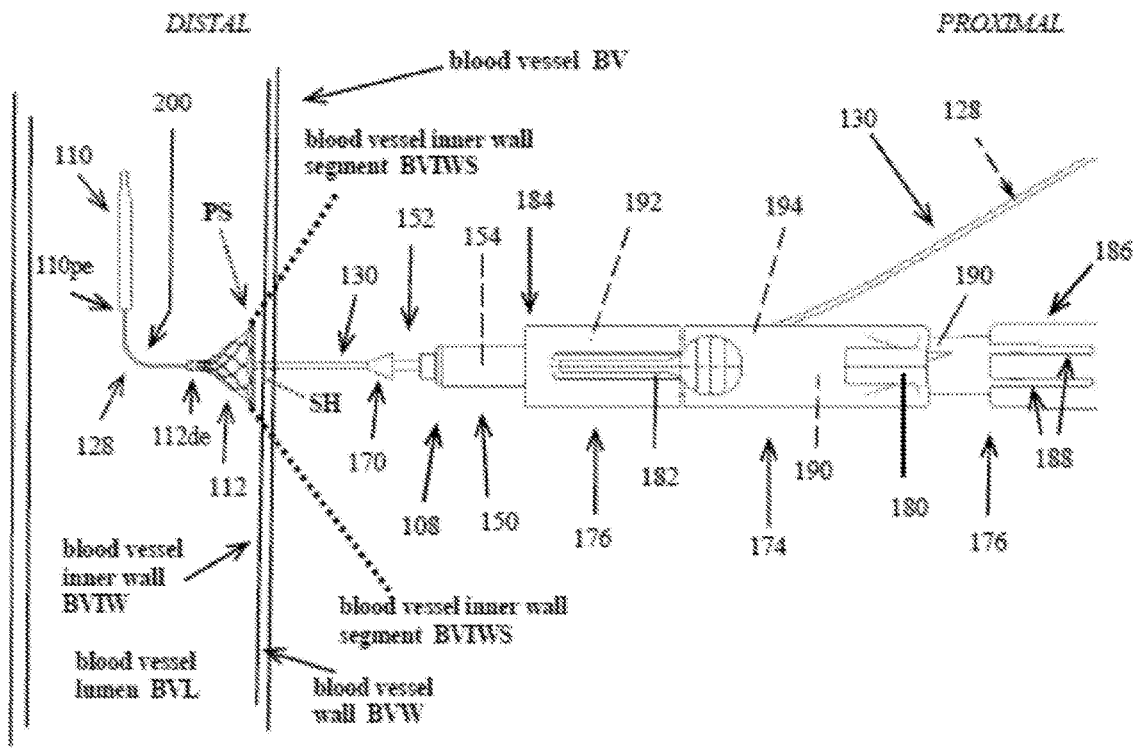

In such exemplary embodiments, flexible control wire 128 is configured to have an activated configuration, whereby the distal end portion of flexible control wire 128 extending between the (neck or apex) distal end of hole sealing assembly 112 (in an activated, self-expanded configuration) and the proximal end 110pe of sheath 110 (having been removed [distally, and non-linearly, moved off of, and positioned a distance away] from hole sealing assembly 112) has an acutely angled curvature (curvature with an acute angle) 200, for example, as shown in FIGS. 2, 5A, 5B. In exemplary embodiments, such acutely angled curvature of the distal end portion of flexible control wire 128 may be up to essentially a right angle, i.e., 90° (ninety degrees), and has a range of between 0° (zero degrees) and 90° (ninety degrees). In exemplary embodiments, such acutely angled curvature of the flexible control wire distal end portion has a length in a range of between a few millimeters (mm) and a few centimeters (cm), for example, 15-20 millimeters (mm).

Flexible control wire acutely angled curvature 200 facilitates efficient, atraumatic physical fitting and accommodating of the (combined) lengths of (a) sheath 110, (b) flexible control wire 128, and (c) hole sealing assembly 112 (in both non-activated, and activated, configurations), within a blood vessel lumen inside a selected blood vessel, such as a blood vessel (e.g., aorta) selected for performing a surgical vascular anastomotic procedure. Specifically, first, for facilitating atraumatic fitting and accommodating, within a blood vessel lumen, of (a) the length of sheath 110, after being distally removed from hole sealing assembly 112 (while still in a non-activated, collapsed configuration), combined with (b) the length of acutely angled curvature 200 of the distal end portion of flexible control wire 128. Second, for facilitating atraumatic fitting and accommodating, within the blood vessel lumen, of (a) the length of sheath 110, after being distally removed from hole sealing assembly 112 (when in an activated, self-expanded configuration), combined with (b) the length of acutely angled distal end portion 200 of flexible control wire 112.

Regarding the second aspect, only when the distal end portion of flexible control wire has acutely angled curvature 200, can the inner diameter of a blood vessel lumen physically fit and accommodate the (combined) lengths of: (a) sheath 110 (distally removed and positioned away from hole sealing assembly 112), (b) flexible control wire distal end portion acutely angled curvature 200, and (c) hole sealing assembly (in a fully activated, fully self-expanded configuration). For a scenario being absent of acutely angled curvature 200 of the distal end portion of flexible control wire 128, the inner diameter of a blood vessel lumen is too small to physically fit and accommodate the (combined) lengths of a [proximal-distal] linear (or near linear) configuration of: (a) sheath 110 (e.g., distally removed, but, adjacent to and not positioned away, from hole sealing assembly 112), and (b) hole sealing assembly 112 (in a fully activated, fully self-expanded configuration).

Such characteristics and features of flexible control wire 112, in turn, facilitate highly efficient and effective operation of hole sealing assembly 112 to atraumatically establish, inside the blood vessel lumen, along a blood vessel inner wall segment thereof, a peripheral seal around a small (needle or syringe sized) hole made in the blood vessel inner wall segment, so as to form a peripherally sealed blood vessel inner wall segment, absent of blood flow, and to maintain the peripherally sealed blood vessel inner wall segment, in the blood flow absence, during formation (generation) of an anastomotic hole through the peripherally sealed blood vessel inner wall segment, in the blood flow absence.

Securing-Anchoring Assembly

In exemplary embodiments of using apparatus 100 in a surgical vascular anastomotic procedure, manual hole sealing controller assembly 114 (via hand-holdable housing assembly 118) is fixedly and firmly held, without moving, in a (stationary) hand of a medical practitioner (e.g., nurse, medical assistant, additional surgeon) present during the surgical vascular anastomotic procedure. Such fixed and firm, stationary manual holding of hand-holdable housing assembly 118 establishes a stable, stationary proximal (reference type) position for hole sealing device proximal portion 106p, in general, and, for manual hole sealing controller assembly 114 (and components therein), in particular, especially, for flexible tube 130 and flexible control wire 128 held therein. Establishing such a stable, stationary proximal (reference type) position for these components is highly desirable, and may even be considered critical, for facilitating effective and accurate manual control (motion, positioning, actuation, operation) of hole sealing device distal portion 106d (including sheath 110 and hole sealing assembly 112 held therein) relative to the selected blood vessel lumen, and inner wall segment therein, of the surgical vascular anastomotic procedure.

In alternative (optional) exemplary embodiments, manual hole sealing controller assembly 114 additionally includes a securing-anchoring assembly that is configured to facilitate reversible securing and anchoring (securing and unsecuring, anchoring and unanchoring) hole sealing device proximal end portion 106p, via connecting hole sealing device proximal end portion 106p to a stable, stationary (fixed) object, and disconnecting hole sealing device proximal end portion 106p therefrom when such securing and anchoring are no longer necessary. Exemplary stable, stationary (fixed) objects are those which are commonly present during surgical vascular anastomotic procedures, such as a patient's surgery bed frame or an object fixedly connected thereto, or various types of surgical equipment (e.g., a surgical retractor), or even a hand of a medical practitioner (nurse, medical assistant, additional surgeon). In such exemplary embodiments, for example, the securing-anchoring assembly is configured to reversibly secure and anchor (via fixidly connecting) manual hole sealing controller assembly 114 to a stable, stationary (fixed) object, and to disconnect manual hole sealing controller assembly 114 therefrom when no longer needed. In exemplary embodiments, the distal portion (or end thereof) of the securing-anchoring assembly is secured and anchored (fixedly connected) to the proximal or middle portion (or an end thereof) of manual hole sealing controller assembly 114, and the proximal portion (or end thereof) of the securing-anchoring assembly is reversibly securable and anchorable (fixedly connectable) to the stable, stationary (fixed) object.

Exemplary embodiments of the securing-anchoring assembly are shown in FIGS. 1, 2, 3, 6, 17, and 18, indicated by reference number 132. According to such exemplary embodiments, securing-anchoring assembly 132 is configured to reversibly secure and anchor (via connecting) manual hole sealing controller assembly 114 to a stable, stationary (fixed) object 133, and to disconnect manual sealing controller assembly 114 from stable, stationary (fixed) object 133 when no longer needed, for example, as indicated in FIGS. 1, 2, and 6, by the dashed line double-headed (bi-directional) arrow 139.

In exemplary embodiments, securing-anchoring assembly 132 is configured as a single, integral flexible (elastic) structure, such as a flexible (elastic) strap, rod, or bar type of structure, having a middle or central portion 134, a distal end portion 136, and a proximal end portion 138. Securing-anchoring assembly distal end portion 136 is present in securing-anchoring assembly 132, as indicated by the dashed line of reference number 136, but, is not visible in FIGS. 1 and 2. Exemplary embodiments of securing-anchoring assembly distal end portion 136 are shown in FIGS. 3 and 6, and further described hereinbelow. In exemplary embodiments, such as of those shown in these figures, each of securing-anchoring assembly distal and proximal end portions 136 and 138, respectively, has a loop (or loop-like), or ring (or ring-like) structure. Securing-anchoring assembly distal end portion 136 is fixedly connected to the proximal or middle portion (or an end thereof) of manual hole sealing controller assembly 114, for example, inside of hand-holdable housing assembly 118. Securing-anchoring assembly proximal end portion 138 is reversibly securable and anchorable (connectable) to a stable, stationary (fixed) object, such as a patient's surgery bed frame or/and an object fixedly connected thereto, or/and various types of surgical equipment (e.g., a surgical retractor), and disconnected therefrom when no longer needed.

In such exemplary embodiments, flexibility (elasticity) of securing-anchoring assembly 132 facilitates maintaining tension of hole sealing assembly 112, for example, via manipulating flexible control wire 128, following reversibly securing and anchoring hole sealing device proximal portion 106p to fixed object 133. Such maintaining of tension of hole sealing assembly 112 is important, for example, in situations where there is slight movement of fixed object 133, or/and of hole sealing device proximal portion 106p, or/and of the patient, during the surgical vascular anastomotic procedure.

An alternative exemplary embodiment of the manual hole sealing controller assembly, including an exemplary embodiment of another securing-anchoring assembly (and components thereof), are illustratively described hereinbelow, and shown in FIG. 7.

Anastomotic Hole Generating Device

Anastomotic hole generating device 108, being another main component of BVIW sealing and hole forming device 102, is configured to atraumatically generate, first, via distally directed motion, and then, via proximally directed motion, an anastomotic hole in, and through, the peripherally sealed blood vessel inner wall segment, in the absence of blood flow.

Anastomotic hole generating device 108 includes: an outer assembly 150, and an inner assembly 152. Outer and inner assemblies 150 and 152, respectively, are coaxially tubular shaped along a (shared) concentric longitudinal axis thereof (i.e., cylindrically shaped structures having centrally, longitudinally bored out cavities extending along the lengths therein). In exemplary embodiments, inner assembly 152 is longer than outer assembly 150 (i.e., total length of inner assembly 152 is greater than total length of outer assembly 150).

As shown in FIG. 1, for apparatus 100 in a non-activated configuration, flexible tube 130, and flexible control wire 128 therewithin, distally extend from hole sealing device proximal portion 106p (from within manual hole sealing controller assembly 114), through the central tubular cavities of inner and outer assemblies 152 and 150, respectively, of anastomotic hole generating device 108, and to hole sealing device distal portion 106d (into sheath 110, with hole sealing assembly 112 (in a non-activated, collapsed configuration) held therein). As shown in FIG. 2, for apparatus 100 in an activated configuration, flexible tube 130, and flexible control wire 128 therewithin, distally extend from hole sealing device proximal portion 106p (from within manual hole sealing controller assembly 114), through the central tubular cavities of inner and outer assemblies 152 and 150, respectively, of anastomotic hole generating device 108, and to hole sealing device distal portion 106d (until the [inside neck or apex] distal end of hole sealing assembly 112 (in an activated, self-expanded configuration)), following removal of sheath 110 from the collapsed hole sealing assembly 112. Accordingly, anastomotic hole generating device 108 is manually reversibly translatable (manually pushable, pullable, and slidably movable forward and backward in distal and proximal directions) along flexible tube 130.

Such manual reversible translatability facilitates manual moving, guiding, and positioning of anastomotic hole generating device 108 (and components thereof) relative to a selected blood vessel and blood vessel wall thereof, as part of preparing to atraumatically generate an anastomotic hole in, and through, a peripherally sealed blood vessel inner wall segment, in the absence of blood flow. Moreover, such reversible translatability of anastomotic hole generating device 108, along flexible tube 130, can be done without affecting position or configuration of hole forming assembly 112 (in an activated, self-expanded configuration) while hole forming assembly 112 maintains the peripherally sealed blood vessel inner wall segment, in the absence of blood flow, during the anastomotic hole forming (generating) procedure.

In exemplary embodiments, along a (shared) concentric longitudinal axis, part of inner assembly 152 is concentrically surrounded by, and closely fitted within and along, outer assembly 150. Such close fitting of part of inner assembly 152 within outer assembly 150 is of a form whereby outer and inner assemblies 150 and 152, respectively, are linearly translatable relative to each other (i.e., slidably movable forward and backward in distal and proximal directions relative to each other, along a concentric longitudinal axis). In exemplary embodiments, the relative linearly translatable motion of outer and inner assemblies 150 and 152, respectively, is controllable and limited via a spring 154. Spring 154 is present in hole generating device 150, as indicated by the dashed line arrow of reference number 154, but, is not visible in FIGS. 1 and 2. Exemplary embodiments of spring 154 are shown in FIGS. 4B, 9B, and 9D, and further described hereinbelow.

The proximal portion of outer assembly 150 includes a protruding rim (e.g., a flange) 156 that is configured to facilitate manual operative reversible connection (connection, disconnection, and re-connection) thereof with the inner assembly distal end 184 of hole forming actuator 104, for example, as indicated in FIG. 1 by the dashed line double-headed (bi-directional) arrow 160.

The proximal end portion of inner assembly 152 is configured with two protruding rims (e.g., flanges), namely, an inner protruding rim 162, and an outer protruding rim 164.

Inner protruding rim 162 of inner assembly 152, along with spring 154, are configured to limit the relative linearly translatable motion of outer and inner assemblies 150 and 152, respectively, of anastomotic hole generating device 108.

Outer protruding rim 164 of inner assembly 152 is configured to facilitate manual operative reversible connection (connection, disconnection, re-connection) of the proximal end of anastomotic hole generating device 108 with the outer assembly distal end of hole forming actuator 104, for example, as indicated in FIG. 1 by the dashed line double-headed (bi-directional) arrow 166. In exemplary embodiments, such manual operative reversible connection of the proximal end of anastomotic hole generating device 108 with the outer assembly distal end of hole forming actuator 104 is also facilitated via operation of a pair of (diametrically) positioned manually controllable connector members 182 (e.g., finger pressure activated elastic fasteners or latches) configured on the outer assembly distal end portion of hole forming actuator 104, as further illustratively described below.

Outer protruding rim 164 of inner assembly 152 is additionally configured to facilitate manual operative reversible connection (connection, disconnection, re-connection) of the proximal end of anastomotic hole generating device 108 with the distal end of manual hole sealing controller assembly 114 (for example, via connecting member 124 and connector members 126 thereof).

Anastomotic Hole Generating Member

The distal end portion of inner assembly 152 is configured with an anastomotic hole generating member 170 that is configured: (i) to atraumatically pass through, via distally (i.e., forwardly) directed (manual pushing) motion, a small hole [i.e., not incision] made (for example, by a needle or syringe) in a blood vessel inner wall segment of a selected blood vessel, in the absence of blood flow; (ii) to generate, via proximally (i.e., reversely) directed (manual pulling) motion, an anastomotic hole through the blood vessel inner wall segment of the selected blood vessel; and (iii) to exit, via further proximally (reversely) directed (manual pulling) motion, the hole generated through the blood vessel inner wall segment of the selected blood vessel.

In exemplary embodiments, the distal portion of anastomotic hole generating member 170 is configured as a tubular cone (i.e., a cone or conical shaped structure having a centrally bored out tubular shaped cavity extending along the [proximal-distal] height therein). The proximal end portion of the tubular cone includes the circular base of the tubular cone, and the distal end portion of the tubular cone includes the tapered point (apex) of the tubular cone. Such tubular cone configuration is highly effective for performing above (i), namely, atraumatically passing through, via distally (forwardly) directed (manual pushing) motion, a small (needle or syringe sized) hole made through the wall of a selected blood vessel. Specifically, the (beveled or tapered) conical shape of the distal portion of anastomotic hole generating member 170, when passing through, via a distally directed (manual pushing) motion, a small hole [i.e., not incision] in a blood vessel wall, atraumatically dilates (widens, enlarges) the small hole in a manner which precludes or minimizes possible undesirable damage or injury to the blood vessel wall, which likely would occur via a non-conical configuration of the distal portion of an anastomotic hole generating member.

In exemplary embodiments, the proximal end portion of the hole generating member tubular cone further includes a non-beveled (non-tapered) tubular segment, continuous with, and proximally extending from, the tubular cone circular base. The non-beveled tubular segment is present in the proximal end portion of the tubular cone, but, is not visible in FIGS. 1 and 2. Exemplary embodiments of the non-beveled tubular segment are shown in FIGS. 4A, 4B, and 9A-9D, and further described below. In exemplary embodiments, the non-beveled (non-tapered) tubular segment has a form of a ring, whose outer diameter is the same as the diameter of the tubular cone circular base, and whose longitudinal (i.e., proximal-distal) length is less than the (proximal-distal) height of the tubular cone. In exemplary embodiments, the proximal end of the tubular segment has a sharp edge configured to cut through a blood vessel wall (from within a blood vessel inner wall segment, to outside the blood vessel inner wall segment), so as to generate an anastomotic hole in the blood vessel wall. Such a tubular segment configuration is highly effective for performing above (ii), namely, to generate, via proximally (i.e., reversely) directed (manual pulling) motion, an anastomotic hole through the blood vessel inner wall segment of the selected blood vessel.

In exemplary embodiments, the remaining proximally extending portion of anastomotic hole generating member 170 (i.e., proximally extending from the tubular segment) is tubular shaped, whose diameter is less than the diameter of the tubular cone circular base (or of the tubular segment continuous therewith), and is configured as a kind of tubular 'tail' proximally extending from the tubular segment proximal end to the middle portion of inner assembly 152. As for the central tubular cavities of inner and outer assemblies 152 and 150, respectively, of anastomotic hole generating device 108, the central tubular cavity of the tubular segment facilitates reversible passage therethrough of flexible tube 130 (with flexible control wire 128 therein).

Hole Forming Actuator

Along with blood vessel inner wall (BVIW) sealing and hole forming device 102, hole forming actuator 104 is another main component of the (overall) apparatus 100 for use in surgical vascular anastomotic procedures.

Hole forming actuator 104 is operably connectable to, and configured to operate, BVIW sealing and hole forming device 102, particularly, to activate (actuate) anastomotic hole generating device 108 thereof.

Hole forming actuator 104 includes: an outer assembly 174, and an inner assembly 176. Outer and inner assemblies 174 and 176, respectively, are coaxially tubular shaped along a (shared) concentric longitudinal axis thereof. In exemplary embodiments, inner assembly 176 is longer than outer assembly 176 (i.e., total length of inner assembly 176 is greater than total length of outer assembly 174).

In exemplary embodiments, along a (shared) concentric longitudinal axis, part of inner assembly 176 is concentrically surrounded by, and closely fitted within and along, outer assembly 174. Such close fitting of part of inner assembly 176 within outer assembly 174 is of a form whereby outer and inner assemblies 174 and 176, respectively, are linearly translatable relative to each other (i.e., manually pushable, pullable, and slidably movable forward and backward in distal and proximal directions relative to each other, along a concentric longitudinal axis).

The proximal end portion of hole forming actuator outer assembly 174 is configured with a pair of oppositely (diametrically) positioned manually controllable guiding members 180 (e.g., rigid finger grips) that facilitate the relative linearly translatable motion of hole forming actuator outer and inner assemblies 174 and 176, respectively.

The distal end portion of hole forming actuator outer assembly 174 is configured with a pair of oppositely (diametrically) positioned manually controllable connector members 182 (e.g., finger pressure activated elastic fasteners or latches), which, as stated above, facilitate manual operative reversible connection of the proximal end (i.e., outer protruding rim 164 of inner assembly 152) of anastomotic hole generating device 108 with the outer assembly distal end of hole forming actuator 104.

The distal end of hole forming actuator inner assembly 176 is configured, for example, as a circular (rim or flange fitting) groove 184, to facilitate manual operative reversible connection (connection, disconnection) thereof with the proximal portion (via protruding rim 156 [e.g., flange]) of anastomotic hole generating device outer assembly 150, for example, as indicated in FIG. 1 (apparatus 100, non-activated) by the dashed line double-headed (bi-directional) arrow 160. Such operative connection is evident in FIG. 2 (apparatus 100 activated), wherein protruding rim (flange) 156 of anastomotic hole generating device outer assembly 150 is operatively connected to (mated and held within) circular groove 184 of hole forming actuator distal end.

The proximal end portion of hole forming actuator inner assembly 176 is configured with a cover (or cap) 186. In exemplary embodiments, cover (or cap) 186 is configured to facilitate user friendly and ergonomic manual use of hole forming actuator 104, particularly, during handling and operating hole forming actuator outer and inner assemblies 174 and 176, respectively, for activating (actuating) anastomotic hole generating device 108. In exemplary embodiments, cover (or cap) 186 is configured with a 'slide-on' type of mechanism, for example, wherein cover (or cap) 186 includes a set of slits (long straight narrow cut or openings) 188 configured to facilitate relatively simple, single piece type of slide on covering, and holding (grasping) onto, the distal end portion of inner assembly 176, for example, as shown in FIGS. 1, 2, 10A-10D, 11A-11D, 12A-12B, 17, and 18. According to such exemplary embodiments, cover (or cap) 186, via slits 188, readily slides and circumferentially holds (grasps) onto the proximal end portion of hole forming actuator inner assembly 176.

Figure 13A:
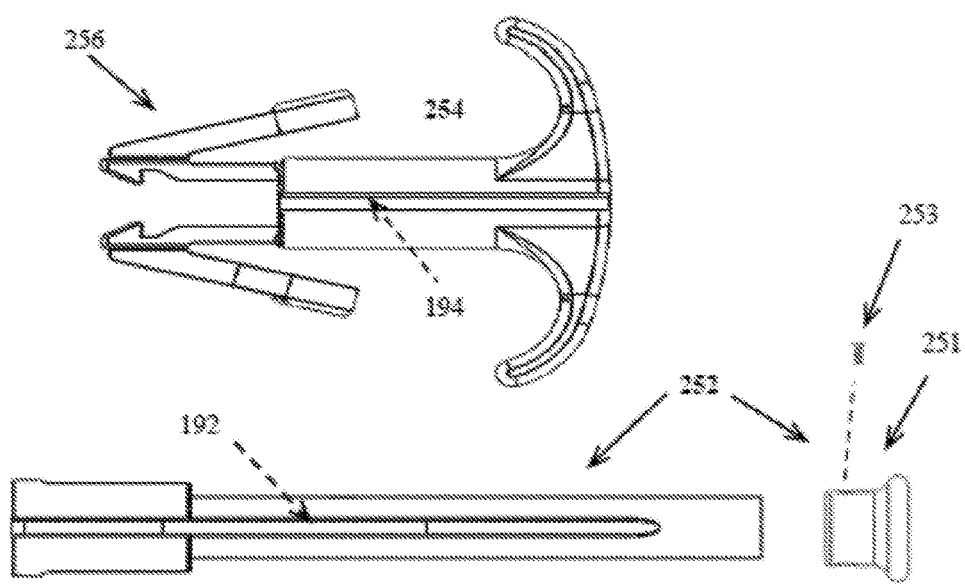
FIGS. 13A and 13B are schematic top and side views, respectively, of another exemplary embodiment of the hole forming actuator, highlighting individual outer and inner assemblies thereof in a non-assembled configuration, with the inner assembly having an exemplary screw-on type of cover, in accordance with some embodiments of the invention.
Figure 13B:
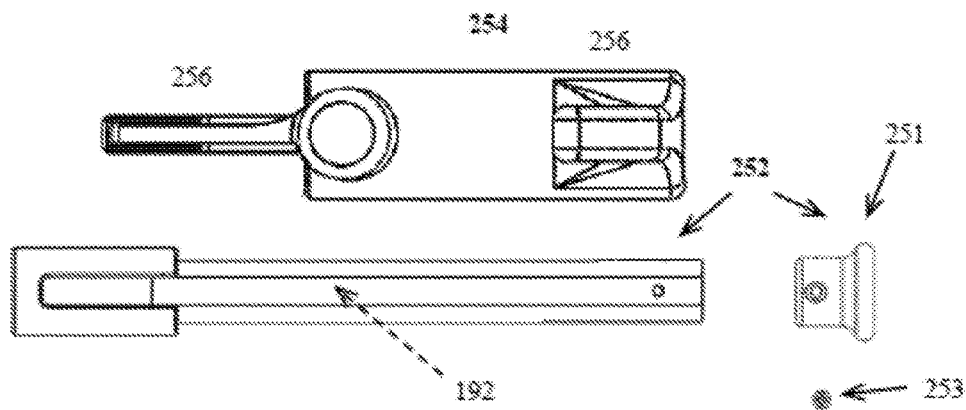

In alternative (optional) exemplary embodiments, cover (or cap) 186 is configured with a 'screw-on' type of mechanism, for example, whereby cover (or cap) 186 and the proximal end portion of inner assembly 176 are each configured with a same sized female thread into which a small screw is screwed so as to hold together cover (or cap) 186 and the proximal end portion of inner assembly 176, for example, as shown in FIGS. 13A-13B.

Longitudinal Side Slots for Relative Slidable Motion

Hole forming actuator inner assembly 176 has two side portions with lengths, (distally to proximally) extending from the middle to proximal portions along the sides of hole forming actuator inner assembly 176, that are configured with a pair of oppositely (diametrically) positioned longitudinal side slots (narrow grooves or channels) 190. In FIGS. 1 and 2, only a segment of one of the two longitudinal side slots 190 is visible, and the non-visible remaining segment of that longitudinal side slot is indicated by the dashed line arrow also having reference number 190. Additional exemplary embodiments of longitudinal side slots 190 are shown in FIGS. 11B-11D, and 12B. Longitudinal side slots 190 (distally to proximally) extend along the (middle-proximal) longitudinal lengths of the two side portions of middle and proximal portions of inner assembly 176.

Longitudinal slide slots 190 additionally facilitate the relative linearly translatable motion of outer and inner assemblies 174 and 176, respectively. Specifically, outer assembly 174 is slidable within, and along, longitudinal slide slots 190 of inner assembly 176, via operation of the pair of manually controllable guiding members 180 (e.g., rigid finger grips) of outer assembly 174.

Longitudinal Top Slot for Manipulating the Flexible Tube, and the Anastomotic Hole Generating Device In exemplary embodiments, hole forming actuator 104 has a top portion with a length, (distally to proximally) extending from the distal end to near the proximal end of hole forming actuator 104, that is configured with a single coaxial dual assembly (or bi-assembly) longitudinal top slot (narrow groove or channel) [192+194]. Dual assembly (or bi-assembly) longitudinal top slot [192+194] is formed by, and includes, an inner assembly longitudinal top slot 192, and an outer assembly longitudinal top slot 194. Hole forming actuator inner assembly 176 is configured with inner assembly longitudinal top slot 192, and hole forming actuator outer assembly 174 is configured with outer assembly longitudinal top slot 194, whereby inner assembly longitudinal top slot 192 is coaxial with outer assembly longitudinal top slot 194.

Dual assembly (or bi-assembly) longitudinal slot [192+194] also facilitates manual operative reversible connection of hole forming actuator 104 with anastomotic hole generating device 108. Specifically, operative reversible connection of the distal end (via rim or flange fitting groove) 184 of hole forming actuator inner assembly 176 with the proximal portion (via protruding rim 156 [e.g., flange)] of anastomotic hole generating device outer assembly 150, for example, as indicated in FIG. 1 (apparatus 100, non-activated) by dashed line double-headed (bi-directional) arrow 160, and shown in FIG. 2 (apparatus 100, activated). For example, when hole forming actuator 104 is brought into close proximity of hole sealing device distal portion 106d, for connecting the distal end 184 of hole forming actuator inner assembly 176 to the proximal portion (via protruding rim 156) of anastomotic hole generating device outer assembly 150, first, dual assembly (or bi-assembly) longitudinal slot [192+194] is used (manually manipulated) to receive and (loosely) enclose (for example, as indicated in FIG. 1 by the dashed line double-headed (bi-directional) arrow 196) flexible tube 130 (with flexible control wire 128 therein), followed by forming the connection (as shown in FIG. 2).

Similar, but opposite, facilitation is in effect when disconnecting hole forming actuator 104 from anastomotic hole generating device 108. For example, for disconnecting the connected components (as shown in FIG. 2), first, the proximal portion (via protruding rim 156) of anastomotic hole generating device outer assembly 150 is disconnected from the distal end 184 of hole forming actuator inner assembly 176, followed by moving and releasing flexible tube 130 from inside of dual assembly (or bi-assembly) longitudinal slot [192+194], to thereby facilitate the disconnection (as again shown in FIG. 1).

As illustratively described above, anastomotic hole generating device 108 is manually reversibly translatable (manually pushable, pullable, and slidably movable forward and backward in distal and proximal directions) along flexible tube 130. After connecting the distal end 184 of hole forming actuator inner assembly 176 to the proximal portion (via protruding rim 156) of anastomotic hole generating device outer assembly 150, dual assembly (or bi-assembly) longitudinal slot [192+194] also facilitates the manual moving, guiding, and positioning (via that part of flexible tube 130 which runs along dual assembly (or bi-assembly) longitudinal slot [192+194]) of anastomotic hole generating device 108 (and components thereof) relative to a selected blood vessel, and blood vessel wall thereof, as part of preparing to atraumatically generate an anastomotic hole in, and through, a peripherally sealed blood vessel inner wall segment, in the absence of blood flow. Moreover, such reversible translatability of anastomotic hole generating device 108, via flexible tube 130 inside of dual assembly longitudinal slot [192+194], can be done without affecting position or configuration of hole forming assembly 112 (in an activated, self-expanded configuration) while hole forming assembly 112 maintains the peripherally sealed blood vessel inner wall segment, in the absence of blood flow, during the anastomotic hole forming (generating) procedure.

Additional Illustrative Description and Details of Various Exemplary Embodiments of the Apparatuses, and Methods, for Use in Surgical Vascular Anastomotic Procedures Following are additional illustrative description and details of various exemplary embodiments of the apparatuses, and methods, for use in surgical vascular anastomotic procedures. Preceding illustrative description of exemplary embodiments of the (overall) apparatus (and components/functions thereof) is fully applicable to the following additional illustrative description, and vice versa.

FIG. 3 is a schematic exploded perspective view of an exemplary embodiment of hole sealing device 106. Hole sealing device 106, being a main component of BVIW sealing and hole forming device 102, is configured to peripherally seal, inside a blood vessel lumen, a blood vessel inner wall segment, from blood flow, so as to form, inside the blood vessel lumen, a peripherally sealed blood vessel inner wall segment, absent of blood flow. Hole sealing device 106 includes: sheath 110, hole sealing assembly 112, manual hole sealing controller assembly 114, flexible control wire 128, and flexible tube 130.

Sheath 110 is configured: (i) to externally cover, closely fit over, fully enclose, and hold hole sealing assembly 112 in a non-activated, collapsed configuration; and (ii) to atraumatically entirely (with the collapsed hole sealing assembly 112) enter into a blood vessel lumen, by passing through a small (needle or syringe sized) hole (previously) made (by a needle or syringe) through a blood vessel wall and along a blood vessel inner wall segment thereof. In FIG. 3, for illustrative purposes, hole sealing assembly 112 is shown outside of sheath 110, in an active, self-expanded configuration.

Sheath 110 is configured as a tubular member having main portion 110*m* whose proximal end 110*pe* is opened, and conical distal end portion 110*d* whose distal end (i.e., tapered point or apex) 110*de* is closed. Sheath conical distal end 110*de* has a maximum outer diameter that is less than the outer diameter of sheath main portion 110*m*. In exemplary embodiments, sheath conical distal end 110*de* has a maximum outer diameter that is less than the diameter of the small (needle or syringe sized) hole (previously) made through the blood vessel wall and along the blood vessel inner wall segment thereof.

The inside of sheath distal end portion 110*d*, for example, at distal end 110*de* thereof, is fixedly connected to the distal end of flexible control wire 128 that controls motion and positioning of sheath 110 and activation (actuation) of hole sealing assembly 112. The proximal end portion of flexible control wire 128 is fixedly connected to the inside of hand-holdable housing assembly 118, for example, via manual control knob 116. Inside of manual hole sealing controller assembly 114, manual control knob 116 is supported by a support member 117. In exemplary embodiments, manual control knob 116 and support member 117 are integrally formed and configured as a single, integral structure.

The (inside neck or apex) distal end of hole sealing assembly 112 and the distal end of flexible tube 130 are fixedly connected to each other. The proximal end of flexible tube 130 is fixedly connected to a tube support member 131, which, in turn, is fixed to the distal end portion of hand-holdable housing assembly 118.

Hand-holdable housing assembly 118 is configured as two complementary parts 118*a* and 118*b*, which, after including portions of the indicated components, are fixedly connected to each other via a pair of screws 117 that are screwed into a corresponding pair of screw holes 119. Complementary parts 118*a* and 118*b*, of hand-holdable housing assembly 118, are configured with two complementary portions 120*a* and 120*b*, respectively, of linear slot (narrow groove or channel) 120, within and along which manual control knob 116 is manually operable and linearly translatable. The distal end portion 136 of exemplary securing-anchoring assembly 132 is fixedly connected to the inside proximal portion of hand-holdable housing assembly 118.

Figure 4A:
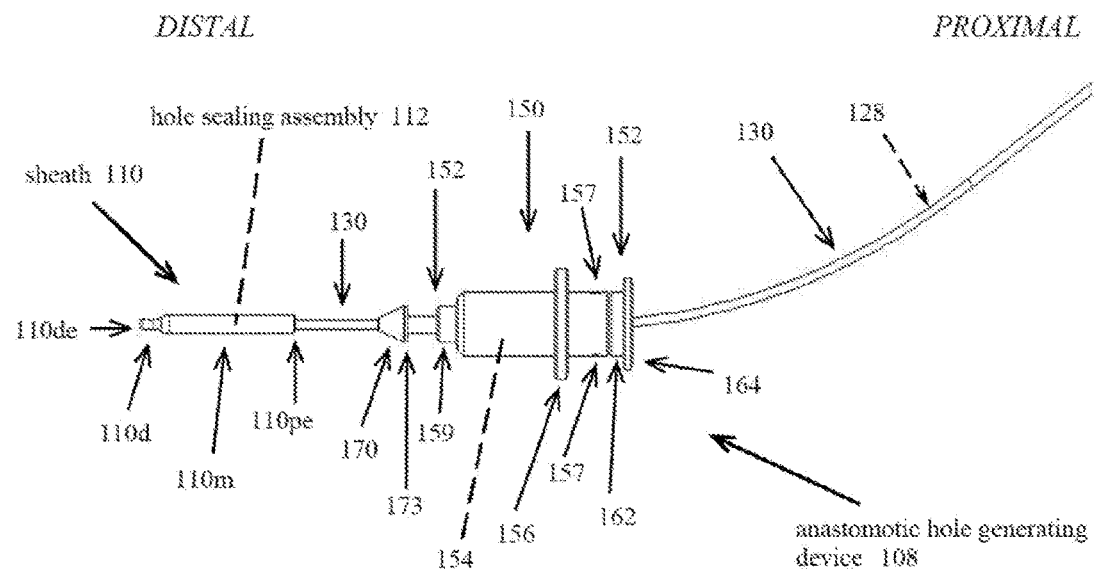
FIGS. 4A and 4B are a schematic side view, and a schematic cross-sectional side view, respectively, of an exemplary embodiment of the (overall) apparatus distal end portion, highlighting components and structural/functional features of the sheath and anastomotic hole generating device, in accordance with some embodiments of the invention.
Figure 4B:
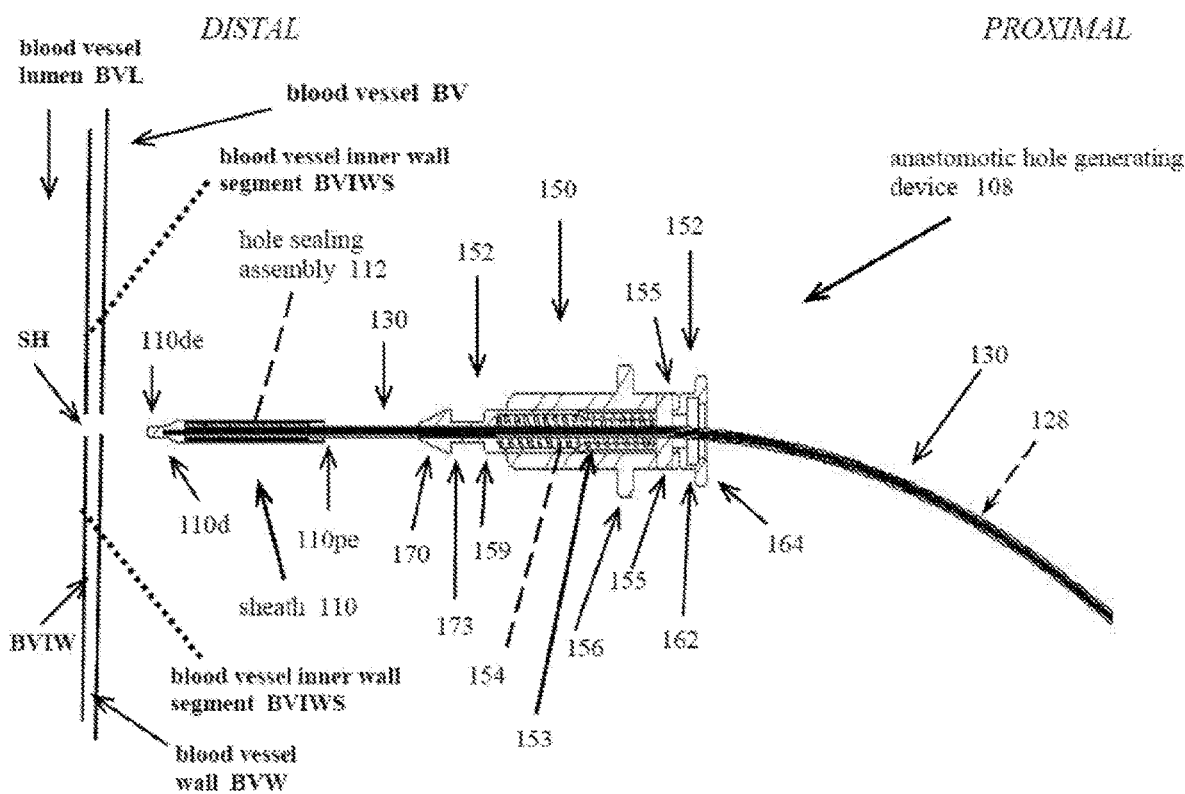

FIGS. 4A and 4B are a schematic side view, and a schematic cross-sectional side view, respectively, of an exemplary embodiment of the (overall) apparatus 100 distal end portion, highlighting components and structural/functional features of sheath 110 and anastomotic hole generating device 108. FIG. 4B shows sheath 110 and anastomotic hole generating device 108, relative to an exemplary blood vessel BV having a blood vessel wall BVW, a blood vessel lumen BVL therein, a blood vessel inner wall BVIW thereof, and a blood vessel inner wall segment BVIWS thereof. FIG. 4B also shows an exemplary small hole [i.e., not incision] SH that was (previously) made (for example, by a medical practitioner using a needle or syringe) through blood vessel wall BVW and along blood vessel inner wall segment BVIWS thereof.

Exemplary blood vessel BV is, for example, an aorta, selected for deploying apparatus 100 for use in a surgical vascular anastomotic procedure (e.g., an end-to-side type of surgical vascular anastomotic procedure). Inside blood vessel BV, blood vessel lumen BVL is bounded (surrounded) by a blood vessel inner wall BVIW. For performing an anastomotic procedure, the targeted area, along blood vessel inner wall BVIW, within (and through) which will be generated an anastomotic hole may be characterized by an exemplary blood vessel inner wall segment BVIWS (indicated in FIG. 4B by the distal ends of the pair of dashed reference lines pointing to approximate upper and lower bounds of exemplary blood vessel inner wall segment BVIWS).

As illustratively described above, sheath 110 is configured: (i) to externally cover, closely fit over, fully enclose, and hold hole sealing assembly 112 in a non-activated, collapsed configuration; and (ii) to atraumatically entirely (with the collapsed hole sealing assembly 112) enter into a blood vessel lumen, by passing through a small (needle or syringe sized) hole (previously) made (for example, by a medical practitioner using a needle or syringe) through blood vessel wall BVW and along blood vessel inner wall segment BVIWS thereof (FIGS. 4B, and 19A-19B).

Sheath 110 is configured as a tubular member having main portion 110m whose proximal end 110pe is opened, and conical (i.e., cone or conical shaped) distal end portion 110d whose distal end (i.e., tapered point or apex) 110de is closed. Conical distal end 110de of sheath 110 has a maximum outer diameter that is less than the outer diameter of main portion 110m of sheath 110. In exemplary embodiments, sheath conical distal end 110de has a maximum outer diameter that is less than the diameter of small hole SH (previously) made through blood vessel wall BVW and along blood vessel inner wall segment BVIWS thereof.

The inside of sheath distal end portion 110d, for example, at distal end 110de thereof, is fixedly connected to the distal end of a flexible control wire 128 that controls motion and positioning of sheath 110 and activation (actuation) of hole sealing assembly 112. For hole sealing assembly 112 in a non-activated, collapsed configuration, flexible tube 130 (enclosing and holding flexible control wire 128), proximally emerges from sheath opened proximal end 110pe.

Sheath conical distal end portion 110d (with closed distal end [tapered point or apex] 110de) is highly effective for atraumatically entirely (with the collapsed hole sealing assembly 112) enter into blood vessel lumen BVL, by passing through small (needle or syringe sized) hole SH made through blood vessel wall BVW and along blood vessel inner wall segment BVIWS thereof. For example, for performing an end-to-side CABG surgical vascular anastomotic procedure, small hole SH is made, through the aorta wall, using a needle or syringe having a diameter in a range of between about 0.8 millimeter (mm) and 1.0 millimeter (mm), resulting in the small hole having a similar diameter. Exemplary sheath 110 has a main portion 110m whose outer diameter is about 2 millimeters (mm), and a conical distal end 110de having an outer diameter of about 0.6 millimeter (mm), being smaller than the diameter of each of sheath main portion 110m (2 mm) and small (needle or syringe sized) hole SH (0.8-1.0 mm). Accordingly, via proximal to distal (pushing) motion of flexible control wire 128, sheath conical distal end 110de (having diameter of about 0.6 mm) readily passes through small hole SH (having diameter of about 0.8-1.0 mm), so as to facilitate, in an atraumatic manner, entry of sheath main portion 110m (having diameter of about 2 mm) into the aorta lumen.

Anastomotic hole generating device 108, being another main component of BVIW sealing and hole forming device 102, is configured to atraumatically generate, first, via distally directed motion, and then, via proximally directed motion, an anastomotic hole in, and through, the peripherally sealed blood vessel inner wall segment, in the absence of blood flow.

Anastomotic hole generating device 108 includes: outer assembly 150, and inner assembly 152. Outer and inner assemblies 150 and 152, respectively, are coaxially tubular shaped along a (shared) concentric longitudinal axis thereof. In exemplary embodiments, inner assembly 152 is longer than outer assembly 150 (i.e., total length of inner assembly 152 is greater than total length of outer assembly 150).

For apparatus 100 in a non-activated configuration, flexible tube 130, and flexible control wire 128 therewithin, distally extend from manual hole sealing controller assembly 114, through the central tubular cavities of anastomotic hole generating device inner and outer assemblies 152 and 150, respectively, and into sheath 110, with hole sealing assembly 112 (in a non-activated, collapsed configuration) held therein.

Along a (shared) concentric longitudinal axis, part of inner assembly 152 is concentrically surrounded by, and closely fitted within and along, outer assembly 150. Such close fitting of part of inner assembly 152 within outer assembly 150 is of a form whereby outer and inner assemblies 150 and 152, respectively, are linearly translatable relative to each other (i.e., slidably movable forward and backward in distal and proximal directions relative to each other, along a concentric longitudinal axis). The relative linearly translatable motion of outer and inner assemblies 150 and 152, respectively, is controllable and limited via a spring 154.

Spring 154 is housed inside a longitudinal slot 153 (FIG. 4B), which, in turn, is coaxially configured inside central tubular cavity of inner assembly 152. The proximal end of spring 154 is held in place inside longitudinal slot 153 via a pin 155. Pin 155 is housed in, and orthogonally (perpendicularly) extends across (through) across central tubular cavity of outer assembly 150 in the proximal end portion of outer assembly 150, proximal to protruding rim (flange) 156. Pin 155 is held in place via a pair of two oppositely (diametrically) positioned holes 157 (FIG. 5A) located in the proximal end portion of outer assembly 150. The distal end of spring 154 is held in place via the distal end 159 of the central tubular cavity of inner assembly 152. Accordingly, spring 154, and motion thereof, are proximally confined via pin 155, and are distally confined via inner assembly central cavity distal end 159.

The distal end portion of inner assembly 152 is configured with anastomotic hole generating member 170 that is configured: (i) to atraumatically pass through, via distally (i.e., forwardly) directed (manual pushing) motion, a small hole [i.e., not incision] made (for example, by a needle or syringe) in a blood vessel inner wall segment of a selected blood vessel, in the absence of blood flow; (ii) to generate, via proximally (i.e., reversely) directed (manual pulling) motion, an anastomotic hole through the blood vessel inner wall segment of the selected blood vessel; and (iii) to exit, via further proximally (reversely) directed (manual pulling) motion, the hole generated through the blood vessel inner wall segment of the selected blood vessel, thereby, exiting the selected blood vessel.

The distal portion of anastomotic hole generating member 170 is configured as a tubular cone. The proximal end portion of the tubular cone includes the circular base of the tubular cone, and the distal end portion of the tubular cone includes the tapered point (apex) of the tubular cone. Such tubular cone configuration is highly effective for performing above (i), namely, atraumatically passing through, via distally (forwardly) directed (manual pushing) motion, a small (needle or syringe sized) hole made through the wall of a selected blood vessel. Specifically, the (beveled or tapered) conical shape of the distal portion of anastomotic hole generating member 170, when passing through, via a distally directed (manual pushing) motion, a small hole [i.e., not incision] in a blood vessel wall, atraumatically dilates (widens, enlarges) the small hole in a manner which precludes or minimizes possible undesirable damage or injury to the blood vessel wall, which likely would occur via a non-conical configuration of the distal portion of an anastomotic hole generating member.

The proximal end portion of hole generating member tubular cone 170 further includes a non-beveled (non-tapered) tubular segment 173, continuous with, and proximally extending from, the tubular cone circular base. Non-beveled (non-tapered) tubular segment 173 has a form of a ring, whose outer diameter is the same as the diameter of the tubular cone circular base, and whose longitudinal (i.e., proximal-distal) length is less than the (proximal-distal) height of tubular cone 170. The proximal end of the tubular segment has a sharp edge configured to cut through a blood vessel wall (from within a blood vessel inner wall segment, to outside the blood vessel inner wall segment), so as to generate an anastomotic hole through the blood vessel wall. Such a tubular segment configuration is highly effective for generating, via proximally (i.e., reversely) directed (manual pulling) motion, an anastomotic hole through the blood vessel inner wall segment. The remaining proximally extending portion of anastomotic hole generating member 170 (i.e., proximally extending from tubular segment 173) is tubular shaped, whose diameter is less than the diameter of the tubular cone circular base (or of tubular segment 173 continuous therewith), and is configured as a kind of tubular 'tail' proximally extending from the proximal end of tubular segment 173 to the middle portion of inner assembly 152. As for the central tubular cavities of inner and outer assemblies 152 and 150, respectively, of anastomotic hole generating device 108, the central tubular cavity of tubular segment 173 facilitates reversible passage therethrough of flexible tube 130 (with flexible control wire 128 therein).

FIGS. 5A and 5B are schematic side views of exemplary embodiments of the (overall) apparatus 100 (in an activated configuration), further highlighting curvature formation of the distal portion of flexible control wire 128 in a blood vessel lumen, via non-linear distally directed removal and separation of sheath 110 from hole sealing assembly 112.

FIG. 5A shows manual hole sealing controller assembly 114 already having been manually operated, via manually (distally) pushing of manual control knob 116 along linear slot 120, so as to facilitate manual control (actuation, motion, positioning) of hole sealing device distal portion 106d (including sheath 110 and hole sealing assembly 112 held therein), before use of anastomotic hole generating device 108.

FIG. 5B shows a close up side view of apparatus 100 components, particularly, those encompassed by hole sealing device distal portion 106d, relative to exemplary blood vessel BV having blood vessel wall BVW, blood vessel lumen BVL therein, blood vessel inner wall BVIW thereof, and blood vessel inner wall segment BVIWS thereof. FIG. 5B also shows exemplary small hole SH (indicated in FIG. 5B by the distal end portion of the dotted reference line going into and through blood vessel wall BVW and blood vessel inner wall BVIW) that was (previously) made (for example, by a medical practitioner using a needle or syringe) through blood vessel wall BVW and along blood vessel inner wall segment BVIWS thereof.

Exemplary blood vessel BV is, for example, an aorta, selected for deploying apparatus 100 for use in a surgical vascular anastomotic procedure (e.g., an end-to-side type of surgical vascular anastomotic procedure). Inside blood vessel BV, blood vessel lumen BVL is bounded (surrounded) by blood vessel inner wall BVIW. For performing an anastomotic procedure, the targeted area, along blood vessel inner wall BVIW, within (and through) which will be generated an anastomotic hole may be characterized by exemplary blood vessel inner wall segment BVIWS (indicated in FIG. 5B by the distal ends of the pair of dashed reference lines pointing to approximate upper and lower bounds of exemplary blood vessel inner wall segment BVIWS).

Via use of flexible control wire 128, sheath 110 is distally removed from hole sealing assembly 112, so as to facilitate self-expansion, and manually controlled positioning, of hole sealing assembly 112 along blood vessel inner wall segment BVIWS, inside blood vessel lumen BVL of the selected blood vessel BV. This, in turn, facilitates hole sealing assembly 112 in an activated, self-expanded configuration, to accurately and atraumatically establish, inside blood vessel lumen BVL, along blood vessel inner wall segment BVIWS thereof, a peripheral seal around a small (needle or syringe sized) hole made in blood vessel inner wall segment BVIWS, so as to form a peripherally sealed blood vessel inner wall segment BVIWS, absent of blood flow, and then, to maintain the peripherally sealed blood vessel inner wall segment BVIWS, in the blood flow absence.

Hole sealing assembly 112 atraumatically establishes and maintains the peripherally sealed blood vessel inner wall segment BVIWS, in the blood flow absence, in order to effectively facilitate (via BVIW sealing and hole forming device 102, and components thereof, including hole generating device 106 and anastomotic hole generating device 108) forming (generating) an anastomotic hole through the peripherally sealed blood vessel inner wall segment BVIWS, in the blood flow absence. Hole sealing assembly 112 atraumatically maintains peripherally sealed blood vessel inner wall segment BVIWS, in the blood flow absence, before, during, and after, BVIW sealing and hole forming device 102 (via hole generating device 106 and anastomotic hole generating device 108) form (generate) an anastomotic hole (e.g., having a diameter of about 4-5 millimeter (mm)) through peripherally sealed blood vessel inner wall segment BVIWS, in the blood flow absence. Such structural and functional characteristics and features of hole sealing assembly 112 provide a highly desirable atraumatic 'blood flow free' local environment peripherally surrounding blood vessel inner wall segment BVIWS, inside blood vessel lumen BVL of the selected blood vessel BV, for performing a surgical vascular anastomosis procedure.

Flexible control wire 128, within flexible tube 130, via manual operation of manual hole sealing controller assembly 114, is linearly translatable (linearly pushable, pullable, and slidably movable forward and backward in distal and proximal directions) between hole sealing device proximal and distal portions 106p and 106d, respectively. In exemplary embodiments, flexible control wire 128, outside of flexible tube 130, via manual operation of manual hole sealing controller assembly 114, is non-linearly translatable (non-linearly pushable, pullable, and slidably movable forward and backward in distal and proximal directions)

between the (neck or apex) distal end 112*de* of hole sealing assembly 112 and the proximal end (opening) 110*pe* of sheath 110.

In exemplary embodiments, sheath 110, hole sealing assembly 112, flexible control wire 128, and flexible tube 130, are configured to have the following activated configurations particularly relevant for use in surgical vascular anastomotic procedures, including, for example, in an end-to-side type of surgical vascular anastomotic procedure.

Sheath 110 and hole sealing assembly 112 have activated configurations, whereby proximal end (i.e., opening) 110*pe* of sheath 110 is not adjacent to, but, rather, a distance away from (neck or apex) distal end 112*de* of hole sealing assembly 112 (in an activated, self-expanded configuration). Specifically, in activated configurations, proximal end 112*pe* of sheath 112, via distally directed manual pushing motion of sheath 110 (via control wire 128), is distally moved off of, and positioned a distance (e.g., at least a few millimeters, and up to a few centimeters) away from, distal end 112*de* of hole sealing assembly 112 (in an activated, self-expanded configuration).

Sheath proximal end 110*pe* is distally, and non-linearly directed, via manual pushing of sheath 110 (and non-linear movement of sheath distal end 110*de*) by the distal end portion of flexible control wire 128, so as to distally, and non-linearly, move off of, and be positioned a distance (e.g., from a few millimeters to a few centimeters) away from, distal end 112*de* of hole sealing assembly (in an activated, self-expanded configuration). Such activated configurations of sheath 110 and hole sealing assembly 112 facilitate control wire 128 to have an activated configuration particularly characterized by an acutely angled curvature 200 (i.e., a curvature having, and characterized by, an acute angle) extending between distal end 200 of hole sealing assembly 112 and proximal end 204 of sheath 110, for example, as follows.

Flexible control wire 128 has an activated configuration, whereby the distal end portion of flexible control wire 128 extending between (neck or apex) distal end 112*de* of hole sealing assembly 112 (in an activated, self-expanded configuration) and proximal end (opening) 110*pe* of sheath 110 (having been removed [distally, and non-linearly, moved off of, and positioned a distance away] from hole sealing assembly 112) has an acutely angled curvature (curvature with an acute angle) 200, for example, as shown in FIGS. 2, 5A, 5B. Acutely angled curvature 200 of the distal end portion of flexible control wire 128 may be up to essentially a right angle, i.e., 90° (ninety degrees), and has a range of between 0° (zero degrees) and 90° (ninety degrees). Acutely angled curvature 200 of the flexible control wire distal end portion has a length in a range of between a few millimeters (mm) and a few centimeters (cm), for example, 15-20 millimeters (mm).

Flexible control wire acutely angled curvature 200 facilitates efficient, atraumatic physical fitting and accommodating of the (combined) lengths of: (a) sheath 110, (b) flexible control wire 128, and (c) hole sealing assembly 112 (in both non-activated, and activated, configurations), within (the inner diameter of) blood vessel lumen BVL inside selected blood vessel BV, such as a blood vessel (e.g., aorta) selected for performing a surgical vascular anastomotic procedure. Specifically, first, for facilitating atraumatic fitting and accommodating, within blood vessel lumen BVL, of: (a) the length of sheath 110, after being distally removed from hole sealing assembly 112 (while still in a non-activated, collapsed configuration), combined with (b) the length of acutely angled curvature 200 of the distal end portion of flexible control wire 128, and with (c) the length of hole sealing assembly 112 (while still in a non-activated, collapsed configuration). Second, for facilitating atraumatic fitting and accommodating, within (the inner diameter of) blood vessel lumen BVL, of: (a) the length of sheath 110, after being distally removed from hole sealing assembly 112 (when in an activated, self-expanded configuration), combined with (b) the length of acutely angled curvature 200 of the distal end portion of flexible control wire 128, and with (c) the length, and width (diameter), of hole sealing assembly (in a fully activated, fully self-expanded configuration).

Regarding the second aspect, only when the distal end portion of flexible control wire has acutely angled curvature 200, can the inner diameter of blood vessel lumen BVL physically fit and accommodate the (combined) lengths of: (a) sheath 110 (distally removed and positioned away from hole sealing assembly 112), (b) flexible control wire distal end portion acutely angled curvature 200, and (c) hole sealing assembly (in a fully activated, fully self-expanded configuration). For a scenario being absent of acutely angled curvature 200 of the distal end portion of flexible control wire 128, the inner diameter of blood vessel lumen BVL is too small to physically fit and accommodate the (combined) lengths of a [proximal-distal] linear (or near linear) configuration of: (a) sheath 110 (e.g., distally removed, but, adjacent to and not positioned away, from hole sealing assembly 112), and (b) hole sealing assembly 112 (in a fully activated, fully self-expanded configuration).

Such characteristics and features of flexible control wire 112, in turn, facilitate highly efficient and effective operation of hole sealing assembly 112 to atraumatically establish, inside blood vessel lumen BVL, along blood vessel inner wall segment BVIWS thereof, a peripheral seal around a small (needle or syringe sized) hole made in blood vessel inner wall segment BVIWS, so as to form a peripherally sealed blood vessel inner wall segment BVIWS, absent of blood flow, and to maintain the peripherally sealed blood vessel inner wall segment BVIWS, in the blood flow absence, during formation (generation) of an anastomotic hole through the peripherally sealed blood vessel inner wall segment, in the blood flow absence.

As illustratively described above (with reference to FIGS. 1 and 2), and further below (with reference to FIG. 8A), hole sealing assembly 112 is configured: (i) to atraumatically establish, inside blood vessel lumen BVL, and along blood vessel inner wall segment BVIWS thereof, a peripheral seal around a small (needle or syringe sized) hole made in blood vessel inner wall segment BVIWS, so as to form a peripherally sealed blood vessel inner wall segment BVIWS, absent of blood flow; and (ii) to maintain the peripherally sealed blood vessel inner wall segment BVIWS, in the blood flow absence. This, in turn, facilitates BVIW sealing and hole forming device 102 (via hole generating device 106 anastomotic hole generating device 108) to form (generate) an anastomotic hole through the peripherally sealed blood vessel inner wall segment, in a highly desirable atraumatic 'blood flow free' local environment peripherally surrounding blood vessel inner wall segment BVIWS, inside blood vessel lumen BVL of the selected blood vessel BV, for performing a surgical vascular anastomosis procedure.

Hole sealing assembly 112 is reversibly collapsible and self-expandable (i.e., collapsible, self-expandable, re-collapsible, etc.), along with having corresponding collapsed and self-expanded configurations. Hole sealing assembly 112 is made of flexible and elastic materials (e.g., flexible and elastic metals, plastics, synthetic polymers, composites, or/and similar type materials) that provide the reversibly self-expandable and collapsible characteristics to hole sealing assembly 112.

Hole sealing assembly 112, in each of a non-activated, collapsed configuration, and an activated, self-expanded configuration, has a distal end portion having a tubular shape or form (i.e., a neck or throat like end portion). The tubular shape or form of the distal end portion (neck or apex) of hole sealing assembly 112 facilitates operative connection to (only) the distal end of flexible tube 130 (with flexible control wire 128). Such operative connection provides flexible control wire 128 the capability of distally passing through flexible tube 130 so as to distally remove sheath 110 from hole sealing assembly 112, leading to hole sealing assembly 112 then having an activated, self-expanded configuration. Such operative connection also provides flexible control wire 128 the capability of proximally pulling back flexible tube 130 so as to return sheath 110 back onto hole sealing assembly 112, thereby, again enclosing and holding hole sealing assembly in a non-activated, collapsed configuration.

Hole sealing assembly 112, in an activated, self-expanded configuration, has an overall hemispherical (umbrella top, dome, or bell) shape or form, that is flexible and elastic. In such exemplary embodiments, hole sealing assembly 112 includes a (main) middle portion having a hemispherical shape or form, and a (relatively short) proximal end portion having an acute flare or flare-like shape or form (i.e., proximally expanding or opening outward from the middle portion). In such exemplary embodiments, the hole sealing assembly (main) middle portion has a (proximal to distal) length that is greater than the (proximal to distal) length of each of the hole sealing assembly distal end portion (neck or apex), and the hole sealing assembly proximal end portion.

In exemplary embodiments, hole sealing assembly middle portion and proximal portion (i.e., proximally extending from the proximal end of hole sealing assembly distal end portion to hole sealing assembly proximal end are configured as a flexible and elastic skeletal (or net, mesh) type frame having struts, that is fully covered (i.e., continuously around and in between the struts) with a flexible and elastic external or outer covering.

In exemplary embodiments, the frame (with the struts) is configured to have a polygonal (e.g., triangular, square, rectangular, pentagonal, hexagonal, heptagonal, octagonal, diamond type shape, or similar) geometrical pattern. In exemplary embodiments, the frame (with the struts) includes a plurality of at least two rows, for example, three rows, of struts having such a polygonal geometrical pattern.

The frame (with the struts) provides the hemispherical and flare shapes or forms of, and structural support to, hole sealing assembly middle and proximal portions. The external or outer covering provides highly effective sealing properties to the hole sealing assembly middle and proximal portions.

Such exemplary embodiments of hole sealing assembly middle and proximal end portions facilitate physically fitting, accommodating, and activating (actuating) hole sealing assembly 112, according to different possible particular shapes or forms, and size dimensions, of different blood vessel lumens inside different blood vessels. For example, as relating to the aorta, whose lumen particular shape or form, and size dimensions, typically vary from patient to patient. Additionally, for example, the flexible shape or form of hole sealing assembly middle and proximal end portions, facilitate real-time (dynamic) self-adapting (self-adjusting, self-changing) thereof to real-time (dynamically changing) structural features of different blood vessel lumens during a surgical vascular anastomotic procedure.

For hole sealing assembly 112, in an activated, self-expanded configuration, the flexible and elastic hemispherical shape or form of hole sealing assembly middle portion 112m, along with the flexible and elastic flare or flare-like shape or form of hole sealing assembly proximal end portion 112p, are particularly relevant, and advantageous, for use in surgical vascular anastomotic procedures, including, for example, in an end-to-side type of surgical vascular anastomotic procedure. For example, for hole sealing assembly 112, in an activated, self-expanded configuration, the flexible hemispherical shape or form of the middle portion, along with the flexible flare or flare-like shape or form of the proximal end, of hole sealing assembly 112 provide sufficient working (operating) space (volume) within the peripherally sealed blood vessel inner wall segment BVIWS, in a blood flow free local environment in the blood vessel lumen BVL, for performing the surgical vascular anastomotic procedure. The flare or flare-like shape or form of the proximal end of hole sealing assembly 112 also provides atraumatic (i.e., non-sharp, non-cutting, sealing) structure to that part (i.e., the proximal end) of hole sealing assembly 112 which directly contacts the periphery (perimeter) of the blood vessel inner wall segment BVIWS (and blood vessel tissue thereof), for establishing and maintaining the peripheral seal around the blood vessel inner wall segment BVIWS (for example, as indicated in FIG. 5B by the dotted line arrow with reference symbol PS).

FIG. 6 is a schematic side view of an exemplary embodiment of the (overall) apparatus 100 proximal end portion, highlighting components and structural/functional features of manual hole sealing controller assembly 114 of hole sealing device 106. Manual hole sealing controller assembly 114 is configured as a hand-holdable module that includes: a manual control knob 116, and a hand-holdable housing assembly 118. In addition to that illustratively described above, with reference to FIG. 4, FIG. 6 shows a close up side view of components and connections inside hand-holdable housing assembly 118. For example, FIG. 6 shows a close up view of the proximal end of flexible tube 130 that is fixedly connected to tube support member 131, which, in turn, is fixed to the distal end portion of hand-holdable housing assembly 118. Additionally, for example, FIG. 6 shows a close up view of the proximal end portion of flexible control wire 128 that is fixedly connected to the inside of hand-holdable housing assembly 118, via manual control knob 116. FIG. 6 also shows a close up view of manual control knob 116 supported by a support member 117, wherein, manual control knob 116 and support member 117 are integrally formed and configured as a single, integral structure.

FIG. 7 is a schematic side view of another exemplary embodiment of the (overall) apparatus 100 proximal end portion, highlighting components and structural/functional features of another exemplary manual hole sealing controller assembly 220 of hole sealing device 106. Manual hole sealing controller assembly 220 is configured as a hand-holdable module that includes: a manual control knob 222, a hand-holdable housing assembly 224, and a securing-anchoring assembly 226.

Manual control knob 222, or similar type of structure, is configured to be manually operable and linearly translatable (manually pushable, pullable, and slidably movable forward and backward in distal and proximal directions), for example, via finger (e.g., thumb) pushing or pulling of manual control knob 222. Hand-holdable housing assembly 224 is configured with a linear slot (narrow groove or channel) 228, within and along which manual control knob 222 is so manually operable and linearly translatable, for example, as indicated in FIG. 7 by the dashed line double-headed (bi-directional) arrow 230.

The proximal end of flexible tube 130 is fixedly connected to a tube support member 232, which, in turn, is fixed to the distal end portion of hand-holdable housing assembly 224. The proximal end portion of flexible control wire 128 is fixedly connected to the inside of hand-holdable housing assembly 224, for example, via manual control knob 222. Inside of hand-holdable housing assembly 224, manual control knob 222 is supported by a support member 234. In exemplary embodiments, manual control knob 222 and support member 234 are integrally formed and configured as a single, integral structure.

Via manual operation of manual hole sealing controller assembly 220 (and manual control knob 222 therein), flexible control wire 128, inside of flexible tube 130 (i.e., prior to distally removing sheath 110 from hole sealing assembly 112), is linearly translatable (linearly pushable, pullable, and slidably movable forward and backward in distal and proximal directions) between hole sealing device proximal and distal portions 106p and 106d, respectively. Similar to that illustratively described above for operation of manual hole sealing controller assembly 114, here also, via manual operation of manual hole sealing controller assembly 220 (and manual control knob 222 therein), in exemplary embodiments, flexible control wire 128, outside of flexible tube 130 (i.e., during and after removal of sheath 110 from hole sealing assembly 112), is non-linearly translatable (non-linearly pushable, pullable, and slidably movable forward and backward in distal and proximal directions) between the (neck or apex) distal end of hole sealing device 112 and the proximal end (opening) of sheath 110.

Securing-anchoring assembly 226 is configured with a spring type mechanism that includes a tension spring 236 operatively connected with a securing-anchoring member 238 (e.g., a pin or rod) whose proximal end 239 is configured as a fastener or latch. Securing-anchoring assembly 226 is configured to reversibly secure and anchor (via fixidly connecting) manual hole sealing controller assembly 220 to a stable, stationary (fixed) object 133, and to disconnect manual sealing controller assembly 220 from stable, stationary (fixed) object 133 when no longer needed, for example, as indicated in FIG. 7 by the dashed line double-headed (bi-directional) arrow 139.

As explained hereinabove, the manual hole sealing controller assembly (114 [FIG. 6] or 220 [FIG. 7]) is a component of the hole sealing device 106, which, in turn, is part of the BVIW sealing and hole forming device 102, which, in turn, is part of the (overall) apparatus 100 for use in surgical vascular anastomotic procedures. In exemplary embodiments, the manual hole sealing controller assembly (114 or 220) may also be considered as an individual 'stand-alone' apparatus. Accordingly, the manual hole sealing controller assembly (114 or 220) apparatus corresponds to an exemplary particular 'sub-combination' of the (overall) apparatus 100 for use in surgical vascular anastomotic procedures, which, in turn, corresponds to another aspect of some embodiments of the present invention.

FIG. 8A is a schematic side view of an exemplary embodiment of hole sealing assembly 112 (part of hole sealing device 106). Hole sealing assembly 112 is configured to atraumatically establish, inside a blood vessel lumen, along an inner wall segment thereof, a peripheral seal around a small (needle or syringe sized) hole made in the blood vessel inner wall segment, so as to form a peripherally sealed blood vessel inner wall segment, absent of blood flow (for example, as shown in FIGS. 5B, and 19C-19D). Hole sealing assembly 112 is also configured to maintain the peripherally sealed blood vessel inner wall segment, in the blood flow absence (for example, as shown in FIGS. 19E-19G).

Hole sealing assembly 112 atraumatically maintains the peripherally sealed blood vessel inner wall segment, in the blood flow absence, before, during, and after, BVIW sealing and hole forming device 102 (via hole generating device 106 and anastomotic hole generating device 108) form (generate) an anastomotic hole (e.g., having a diameter of about 4-5 millimeter (mm) through the peripherally sealed blood vessel inner wall segment, in the blood flow absence. Such structural and functional characteristics and features of hole sealing assembly 112 provide a highly desirable atraumatic 'blood flow free' local environment peripherally surrounding the blood vessel inner wall segment, inside the blood vessel lumen of the selected blood vessel, for performing a surgical vascular anastomosis procedure.

In exemplary embodiments, hole sealing assembly 112 is reversibly collapsible and self-expandable (i.e., collapsible, self-expandable, re-collapsible, etc.), along with having corresponding collapsed and self-expanded configurations. Hole sealing assembly 112 is made of flexible and elastic materials (e.g., flexible and elastic metals, plastics, synthetic polymers, composites, or/and similar type materials) that provide the self-expandable and collapsible characteristics to hole sealing assembly 112. Hole sealing assembly 112 has a non-activated, collapsed configuration similar to that of a closed (collapsed) umbrella top. Hole sealing assembly 112 has an activated, self-expanded configuration similar to that of an opened (expanded) umbrella top. Hole sealing assembly 112 is configured to be self-expandable, from the non-activated, collapsed configuration to the activated, self-expanded configuration. Specifically, hole sealing assembly 112 is confined to a collapsed configuration by being enclosed within and held by sheath 110. Upon removal of sheath 110 from around hole sealing assembly 112, hole sealing assembly 112 self-expands to a self-expanded configuration.

Hole sealing assembly 112, in each of a non-activated, collapsed configuration, and an activated, self-expanded configuration, has a (relatively short) distal end portion 112d (including distal end 112de thereof) having a tubular shape or form (i.e., a neck or throat like end portion).

In such exemplary embodiments, the tubular shape or form of distal end portion (neck or apex) 112d of hole sealing assembly 112 facilitates operative connection to (only) the distal end of flexible tube 130 (with flexible control wire 128 inside). Such operative connection provides flexible control wire 128 the capability of distally passing through flexible tube 130 so as to distally remove sheath 110 from hole sealing assembly 112, leading to hole sealing assembly 112 then having an activated, self-expanded configuration. Such operative connection also provides flexible control wire 128 the capability of proximally pulling back sheath 110 so as to return sheath 110 back onto hole sealing assembly 112, thereby, again enclosing and holding hole sealing assembly 112 in a non-activated, collapsed configuration.

Hole sealing assembly 112, in an activated, self-expanded configuration, has an overall hemispherical (umbrella top, dome, or bell) shape or form, that is flexible and elastic. In such exemplary embodiments, hole sealing assembly 112, in an activated, self-expanded configuration, includes a (main)

middle portion 112m having a hemispherical shape or form, and a (relatively short) proximal end portion 112p having an acute flare or flare-like shape or form (i.e., from the proximal end of middle portion 112m, proximally gradually, non-linearly expanding or opening outward until the proximal end 112pe of proximal end portion 112p). In such exemplary embodiments, hole sealing assembly (main) middle portion 112m has a (proximal to distal) length that is greater than the (proximal to distal) length of each of hole sealing assembly distal end portion (neck or apex) 112d, and hole sealing assembly proximal end portion 112p.

In exemplary embodiments, hole sealing assembly middle portion 112m and proximal portion 112p (i.e., proximally extending from the proximal end of hole sealing assembly distal end portion 112d to hole sealing assembly proximal end 112pe) are configured as a flexible and elastic skeletal (or net, mesh) type frame 240 having struts 240s, that is fully covered (i.e., continuously around and in between struts 240s) with a flexible and elastic external or outer covering 242.

In exemplary embodiments, frame 240 (with struts 240s) is configured to have a polygonal (e.g., triangular, square, rectangular, pentagonal, hexagonal, heptagonal, octagonal, diamond type shape, or similar) geometrical pattern. In exemplary embodiments, frame 240 (with struts 240s) includes a plurality of at least two rows, for example, three rows, of struts 240s having such a polygonal geometrical pattern. For example, as shown in FIG. 8A, frame 240 (with struts 240s) includes a plurality of three rows of struts 240s having a diamond-like shape geometrical pattern.

Frame 240 (with struts 240s) provides the hemispherical and flare shapes or forms of, and structural support to, hole sealing assembly middle portion 112m and proximal end portion 112p. External or outer covering 242 provides highly effective sealing properties to hole sealing assembly middle portion 112m and proximal end portion 112p.

Such exemplary embodiments of hole sealing assembly middle portion 112m and proximal end portion 112p facilitate physically fitting, accommodating, and activating (actuating) hole sealing assembly 112, according to different possible particular shapes or forms, and size dimensions, of different blood vessel lumens inside different blood vessels. For example, as relating to the aorta, whose lumen particular shape or form, and size dimensions, typically vary from patient to patient. Additionally, for example, the flexible shape or form of hole sealing assembly middle portion 112m and proximal end portion 112p, facilitate real-time (dynamic) self-adapting (self-adjusting, self-changing) thereof to real-time (dynamically changing) structural features of different blood vessel lumens during a surgical vascular anastomotic procedure.

For hole sealing assembly 112, in an activated, self-expanded configuration, the flexible and elastic hemispherical shape or form of hole sealing assembly middle portion 112m, along with the flexible and elastic flare or flare-like shape or form of hole sealing assembly proximal end portion 112p, are particularly relevant, and advantageous, for use in surgical vascular anastomotic procedures, including, for example, in an end-to-side type of surgical vascular anastomotic procedure. For example, for hole sealing assembly 112, in an activated, self-expanded configuration, the flexible hemispherical shape or form of hole sealing assembly middle portion 112m, along with the flexible flare or flare-like shape or form of hole sealing assembly proximal end portion 112p, provide sufficient working (operating) space (volume) within the peripherally sealed blood vessel inner wall segment, in a blood flow free local environment in the blood vessel lumen, for performing a surgical vascular anastomotic procedure. The flare or flare-like shape or form of hole sealing assembly proximal end portion 112p also provides atraumatic (i.e., non-sharp, non-cutting, sealing) structure to that part (i.e., circumferential proximal end 112pe of proximal end portion 112p) of hole sealing assembly 112 which directly contacts the periphery (perimeter) of the blood vessel inner wall segment (and tissue thereof), for establishing and maintaining the peripheral seal around the blood vessel inner wall segment.

FIG. 8B is a schematic side view of an exemplary embodiment of another exemplary hole sealing assembly, referenced and referred to as hole sealing assembly 113. Exemplary embodiment of hole sealing assembly 113 is similar to exemplary embodiment of hole sealing assembly 112, with the only difference being that hole sealing assembly 113 includes a proximal end portion 113p absent of a flare or flare-like shape or form.

Hole sealing assembly 113, in each of a non-activated, collapsed configuration, and an activated, self-expanded configuration, has a (relatively short) distal end portion 113d (including distal end 113de thereof) having a tubular shape or form (i.e., a neck or throat like end portion).

Hole sealing assembly 113, in an activated, self-expanded configuration, has an overall hemispherical (umbrella top, dome, or bell) shape or form (i.e., extending from the distal end of middle portion 113m to the proximal end 113pe of proximal end portion 113p), that is flexible and elastic. In such exemplary embodiments, hole sealing assembly 113, in an activated, self-expanded configuration, includes a (main) middle portion 113m, and a proximal end portion 113p (with proximal end 113pe), that together have a hemispherical shape or form. In such exemplary embodiments, hole sealing assembly (main) middle portion 113m has a (proximal to distal) length that is greater than the (proximal to distal) length of each of hole sealing assembly distal end portion (neck or apex) 113d, and hole sealing assembly proximal end portion 113p.

In exemplary embodiments, hole sealing assembly middle portion 113m and proximal portion 113p (i.e., proximally extending from the proximal end of hole sealing assembly distal end portion 113d to hole sealing assembly proximal end 113pe) are configured as a flexible and elastic skeletal (or net, mesh) type frame 245 having struts 245s, that is fully covered (i.e., continuously around and in between struts 245s) with a flexible and elastic external or outer covering 247.

In exemplary embodiments, frame 245 (with struts 245s) is configured to have a polygonal (e.g., triangular, square, rectangular, pentagonal, hexagonal, heptagonal, octagonal, diamond type shape, or similar) geometrical pattern. In exemplary embodiments, frame 245 (with struts 245s) includes a plurality of at least two rows, for example, three rows, of struts 245s having such a polygonal geometrical pattern. For example, as shown in FIG. 8B, frame 245 (with struts 245s) includes a plurality of three rows of struts 245s having a diamond-like shape geometrical pattern. Frame 245 (with struts 245s) provides the hemispherical shape or form of, and structural support to, hole sealing assembly middle portion 113m and proximal end portion 113p. External or outer covering 247 provides highly effective sealing properties to hole sealing assembly middle portion 113m and proximal end portion 113p.

As explained hereinabove, the hole sealing assembly (112 [FIG. 8A] or 113 [FIG. 8B]) is a component of the hole sealing device 106, which, in turn, is part of the BVIW sealing and hole forming device 102, which, in turn, is part of the (overall) apparatus 100 for use in surgical vascular anastomotic procedures. In exemplary embodiments, the hole sealing assembly (112 or 113) may also be considered as an individual 'stand-alone' apparatus. Accordingly, the hole sealing assembly (112 or 113) apparatus corresponds to an exemplary particular 'sub-combination' of the (overall) apparatus 100 for use in surgical vascular anastomotic procedures, which, in turn, corresponds to another aspect of some embodiments of the present invention.

Figure 9A:
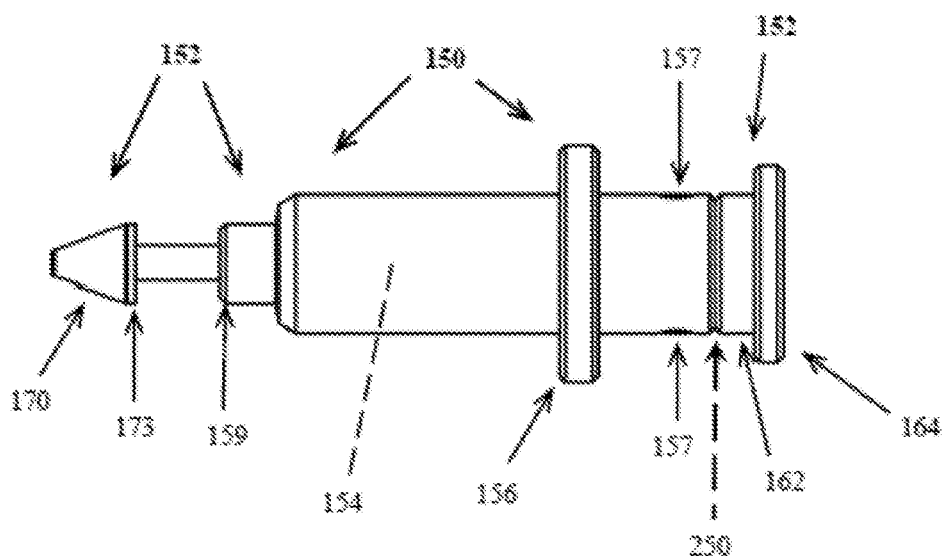
FIGS. 9A and 9B are schematic side and cross-sectional side views, respectively, of an exemplary embodiment of the anastomotic hole generating device (part of the BVIW sealing and hole forming device), in an non-activated (non-actuated) configuration, in accordance with some embodiments of the invention.
Figure 9B:
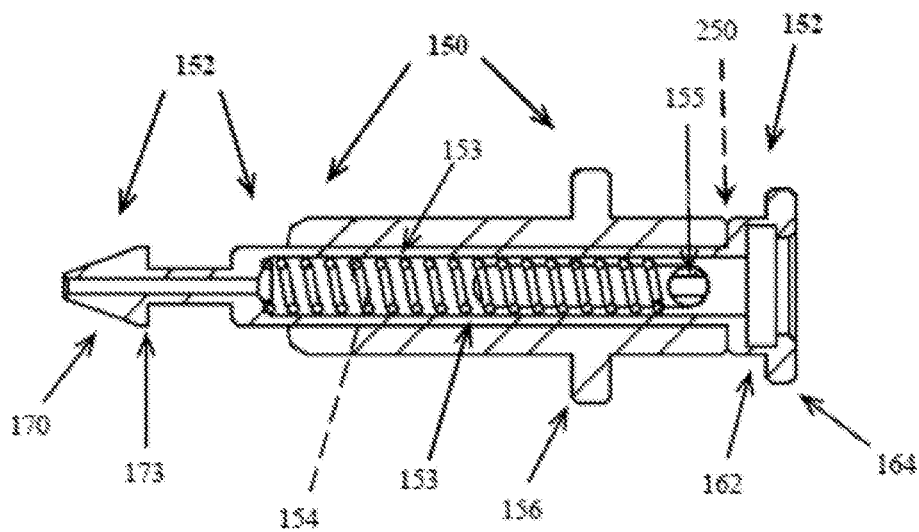
Figure 9C:
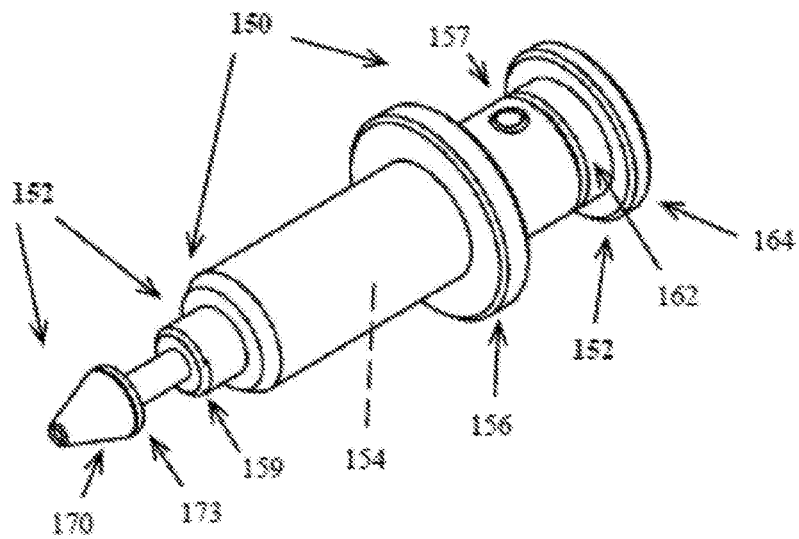
FIGS. 9C and 9D are schematic perspective and exploded perspective views, respectively, of an exemplary embodiment of the anastomotic hole generating device (part of the BVIW sealing and hole forming device), in accordance with some embodiments of the invention.
Figure 9D:
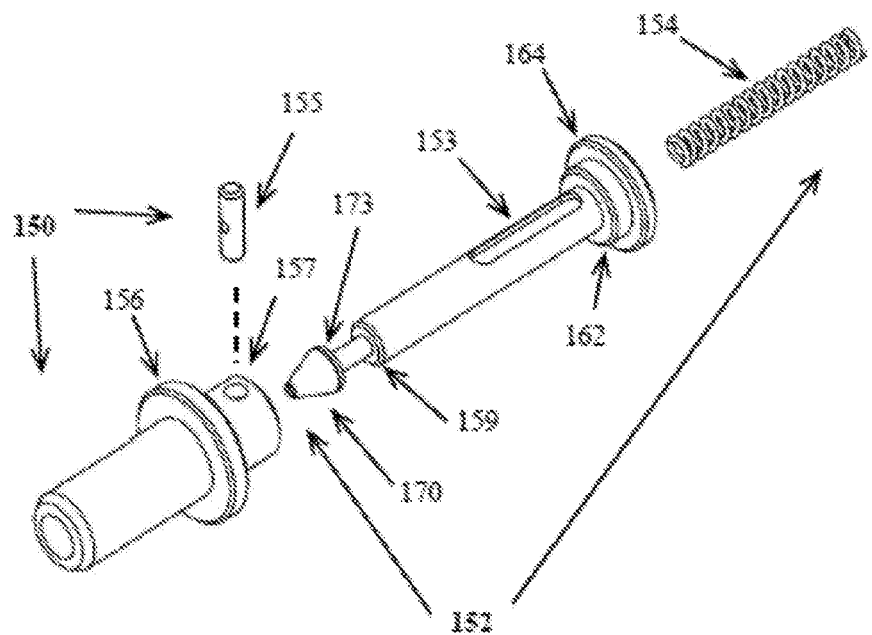

FIGS. 9A and 9B are a schematic side view, and a schematic cross-sectional side view, respectively, of an exemplary embodiment of anastomotic hole generating device 108 (part of BVIW sealing and hole forming device 102), in a non-activated (non-actuated) configuration. FIGS. 9C and 9D are a schematic perspective view, and a schematic exploded perspective view, respectively, of an exemplary embodiment of anastomotic hole generating device 108. The numerous structural and functional (operational) characteristics and features of exemplary embodiments of anastomotic hole generating device 108, and components thereof, are illustratively described above and are fully applicable to the exemplary embodiments shown in FIGS. 9A-9D.

In FIGS. 9A-9C, anastomotic hole generating device 108 is shown in an exemplary non-activated (non-actuated) configuration, via outer assembly 150 and inner assembly 152 adjoining (i.e., not moved apart from) each other, namely, the proximal end of outer assembly 150 is immediately adjacent to, and directly contacting, the distal end of the proximal end portion of inner assembly 152, as indicated in FIGS. 9A and 9B by the dashed line arrow of reference number 250.

As explained hereinabove, the anastomotic hole generating device 108 is a component of BVIW sealing and hole forming device 102, which, in turn, is part of the (overall) apparatus 100 for use in surgical vascular anastomotic procedures. In exemplary embodiments, the anastomotic hole generating device 108 may also be considered as an individual 'stand-alone' apparatus. Accordingly, the anastomotic hole generating device 108 apparatus corresponds to an exemplary particular 'sub-combination' of the (overall) apparatus 100 for use in surgical vascular anastomotic procedures, which, in turn, corresponds to another aspect of some embodiments of the present invention.

Figure 10A:
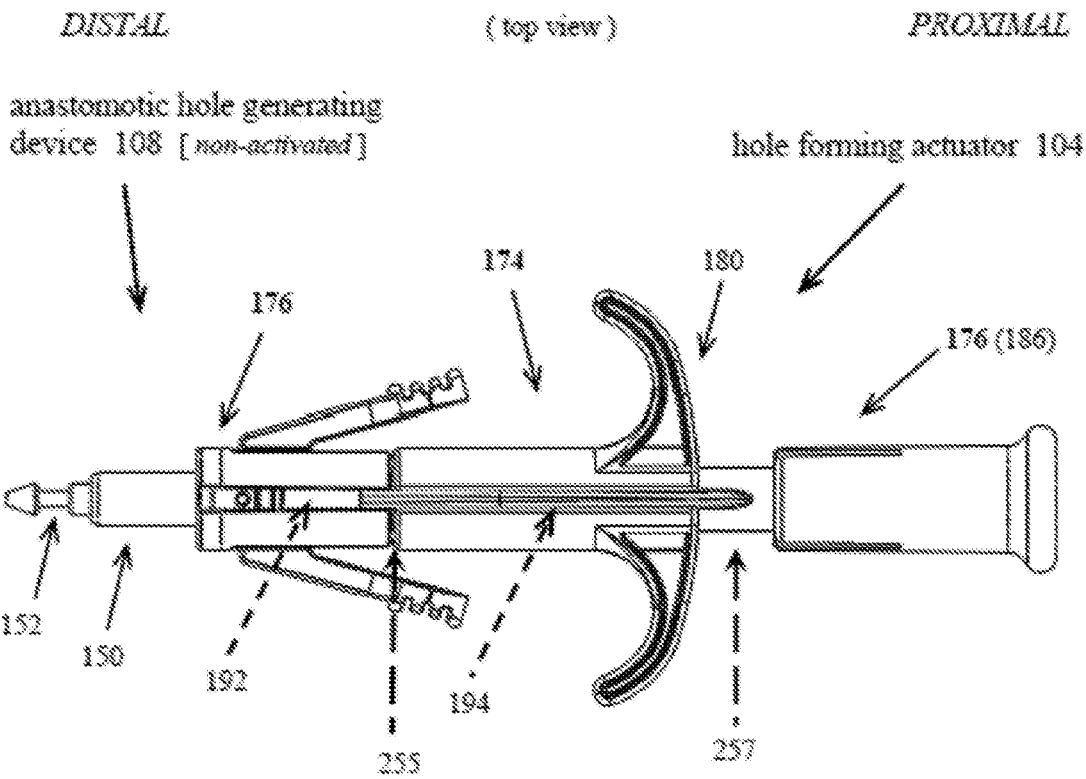
FIGS. 10A and 10B are schematic top and cross-sectional top views, respectively, of an exemplary embodiment of the anastomotic hole generating device (part of the BVIW sealing and hole forming device) with the hole forming actuator, in a non-activated (non-actuated) configuration, in accordance with some embodiments of the invention.
Figure 10B:
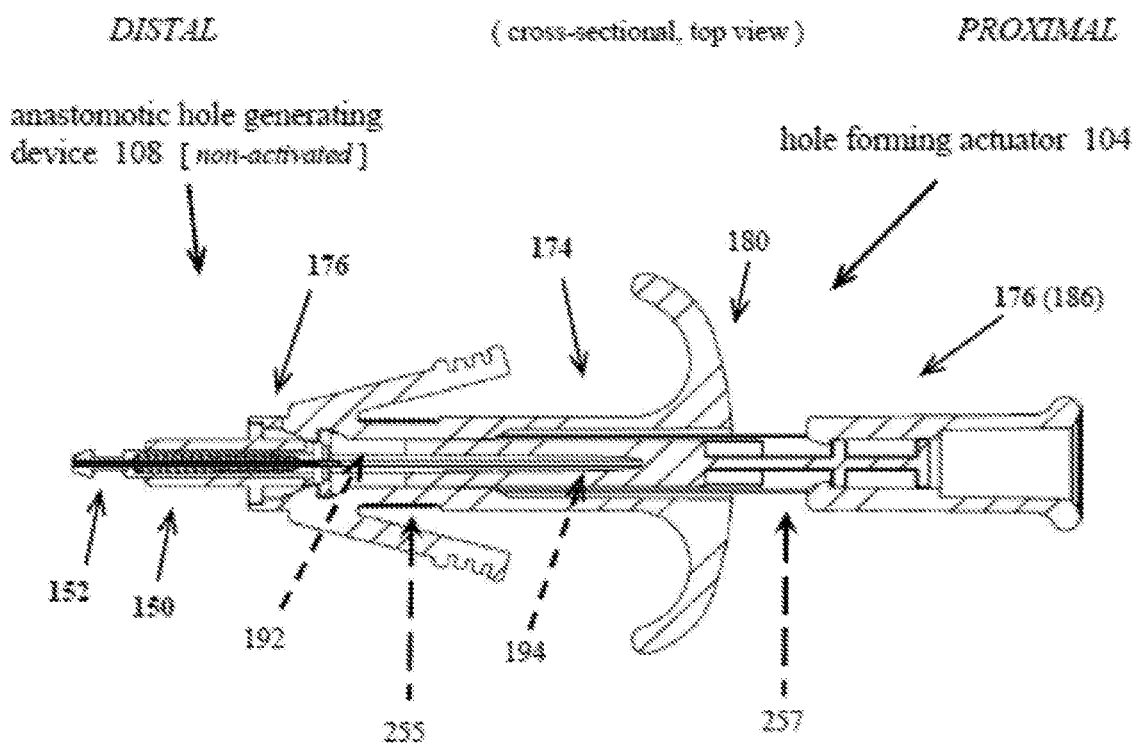
Figure 10C:
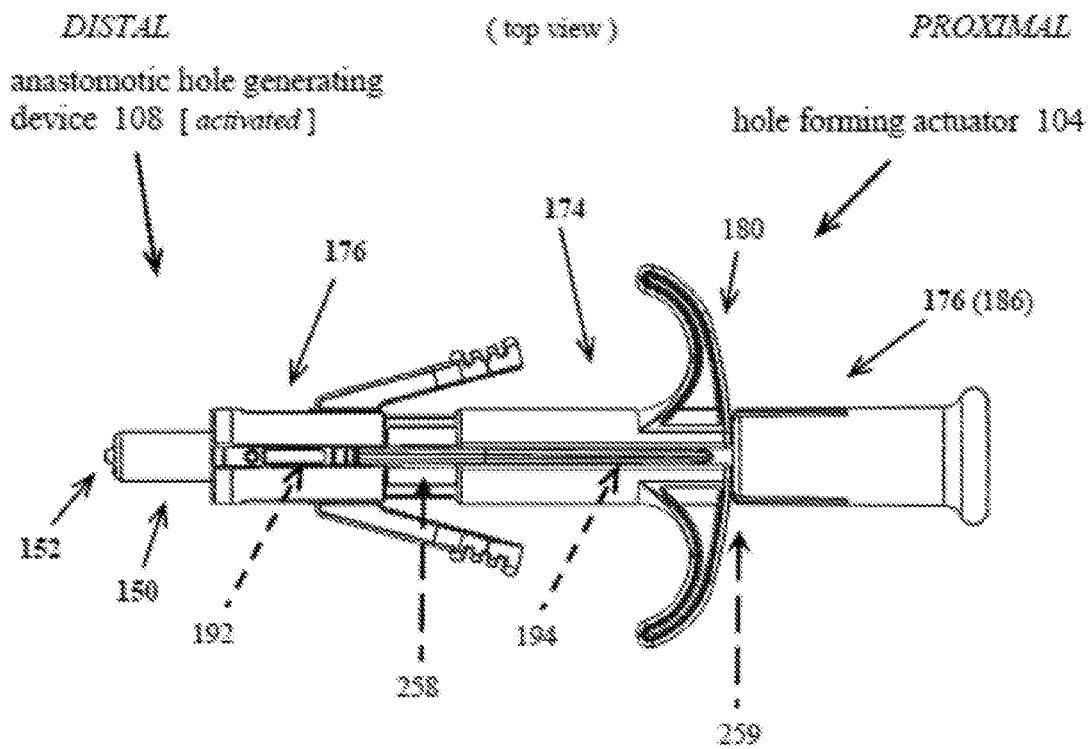
FIGS. 10C and 10D are schematic top and cross-sectional top views, respectively, of an exemplary embodiment of the anastomotic hole generating device with the hole forming actuator, in an activated (actuated) configuration, in accordance with some embodiments of the invention.
Figure 10D:
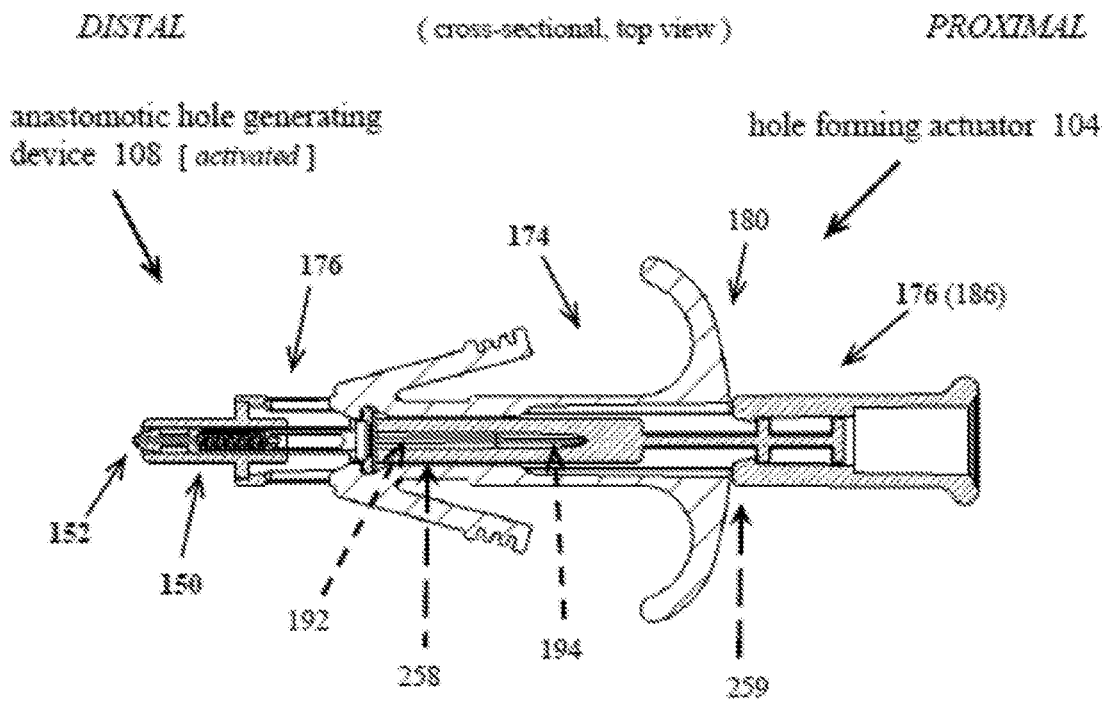

FIGS. 10A and 10B are a schematic top view, and a schematic cross-sectional top view, respectively, of an exemplary embodiment of anastomotic hole generating device 108 (part of BVIW sealing and hole forming device 102) connected (coupled) with hole forming actuator 104, in a non-activated (non-actuated) configuration. FIGS. 10C and 10D are schematic top and cross-sectional top views, respectively, of an exemplary embodiment of anastomotic hole generating device 108 connected (coupled) with hole forming actuator 104, in a non-activated (non-actuated) configuration. The numerous structural and functional (operational) characteristics and features of exemplary embodiments of anastomotic hole generating device 108, and of hole forming actuator 104, and components thereof, are illustratively described above and are fully applicable to the exemplary embodiments shown in FIGS. 10A-10D.

In FIGS. 10A and 10B, anastomotic hole generating device 108 and hole forming actuator 104 are shown in an exemplary non-activated (non-actuated) configuration, via hole forming actuator outer assembly 174 and inner assembly 176 adjoining (i.e., not moved or positioned apart from) each other, namely, outer and inner assemblies 174 and 176, respectively, are immediately adjacent to, and directly contacting, each other, as indicated in FIGS. 10A and 10B by the dashed line arrow of reference number 255. Such an exemplary non-activated (non-actuated) configuration is also shown by the relative positions of the pair of hole forming actuator guiding members (finger grips) 180 (that facilitate relative linearly translatable motion of hole forming actuator outer and inner assemblies 174 and 176, respectively) and the hole forming actuator inner assembly proximal end (e.g., indicated by cover 186). Namely, the proximal end (i.e., back or spine) of the pair of hole forming actuator guiding members 180 is separated (i.e., positioned apart from, and not adjoining) the hole forming actuator inner assembly proximal end (cover 186), as indicated in FIGS. 10A and 10B by the dashed line arrow of reference number 257. Such an exemplary non-activated (non-actuated) configuration is also shown by the relative positions of anastomotic hole generating device inner and outer assemblies 152 and 150, respectively. Namely, anastomotic hole generating device inner assembly 152 distally emerges from inside of anastomotic hole generating device outer assembly 150. This corresponds to the position and configuration of anastomotic hole generating device 108 before being activated (actuated), via hole forming actuator 104, for generating an anastomotic hole in a blood vessel inner wall segment.

In FIGS. 10C and 10D, anastomotic hole generating device 108 and hole forming actuator 104 are shown in an exemplary activated (actuated) configuration, via hole forming actuator outer and inner assemblies 174 and 176, respectively, being separated (i.e., moved or positioned apart) from each other, namely, outer and inner assemblies 174 and 176 are separated (moved or positioned apart) from each other, as indicated in FIGS. 10C and 10D by the dashed line arrow of reference number 258. Such an exemplary activated (actuated) configuration is also shown by the relative positions of the pair of hole forming actuator guiding members (finger grips) 180 and the hole forming actuator inner assembly proximal end (e.g., indicated by cover 186). Namely, the proximal end (back or spine) of the pair of hole forming actuator guiding members 180 is adjoined (i.e., not positioned or moved apart from) the hole forming actuator inner assembly proximal end (cover 186), as indicated in FIGS. 10C and 10D by the dashed line arrow of reference number 258. Such an exemplary non-activated (non-actuated) configuration is also shown by the relative positions of anastomotic hole generating device inner and outer assemblies 152 and 150, respectively. Namely, anastomotic hole generating device inner assembly 152 is nearly entirely (proximally pulled) inside of anastomotic hole generating device outer assembly 150. This corresponds to position and configuration of anastomotic hole generating device 108 after being activated (actuated), via hole forming actuator 104, for generating an anastomotic hole in a blood vessel inner wall segment.

FIGS. 10A-10D also show close-up views of hole forming actuator dual assembly (or bi-assembly) longitudinal top slot [192+194], relative to anastomotic hole generating device 108. Dual assembly (or bi-assembly) longitudinal top slot [192+194] is formed by, and includes, inner assembly longitudinal top slot 192, and outer assembly longitudinal top slot 194. Hole forming actuator inner assembly 176 is configured with inner assembly longitudinal top slot 192, and hole forming actuator outer assembly 174 is configured with outer assembly longitudinal top slot 194, whereby inner assembly longitudinal top slot 192 is coaxial with outer assembly longitudinal top slot 194.

Dual assembly (or bi-assembly) longitudinal slot [192+194] also facilitates manual operative reversible connection of hole forming actuator 104 with anastomotic hole generating device 108. Specifically, operative reversible connection of the distal end of hole forming actuator inner assembly 176 with the proximal portion of anastomotic hole generating device outer assembly 150, for example, as indicated in FIG. 1 (apparatus 100, non-activated) by dashed line double-headed (bi-directional) arrow 160, and shown in FIG. 2 (apparatus 100, activated). For example, when hole forming actuator 104 is brought into close proximity of hole sealing device distal portion 106d, for connecting the distal end 184 of hole forming actuator inner assembly 176 to the proximal portion (via protruding rim 156) of anastomotic hole generating device outer assembly 150, first, dual assembly (or bi-assembly) longitudinal slot [192+194] is used (manually manipulated) to receive and (loosely) enclose (for example, as indicated in FIG. 1 by the dashed line double-headed (bi-directional) arrow 196) flexible tube 130 (with flexible control wire 128 therein), followed by forming the connection (as shown in FIG. 2).

Similar, but opposite, facilitation is in effect when disconnecting hole forming actuator 104 from anastomotic hole generating device 108. For example, for disconnecting the connected components (as shown in FIG. 2), first, the proximal portion (via protruding rim 156) of anastomotic hole generating device outer assembly 150 is disconnected from the distal end 184 of hole forming actuator inner assembly 176, followed by moving and releasing flexible tube 130 from inside of dual assembly (or bi-assembly) longitudinal slot [192+194], to thereby facilitate the disconnection (as again shown in FIG. 1).

As explained hereinabove, the anastomotic hole generating device 108, and the hole forming actuator 104, are components of the (overall) apparatus 100 for use in surgical vascular anastomotic procedures. In exemplary embodiments, the anastomotic hole generating device 108, with the hole forming actuator 104, may also be considered as an individual 'stand-alone' apparatus. Accordingly, the anastomotic hole generating device 108 with the hole forming actuator 104 apparatus corresponds to an exemplary particular 'sub-combination' of the (overall) apparatus 100 for use in surgical vascular anastomotic procedures, which, in turn, corresponds to another aspect of some embodiments of the present invention.

Figure 11C:
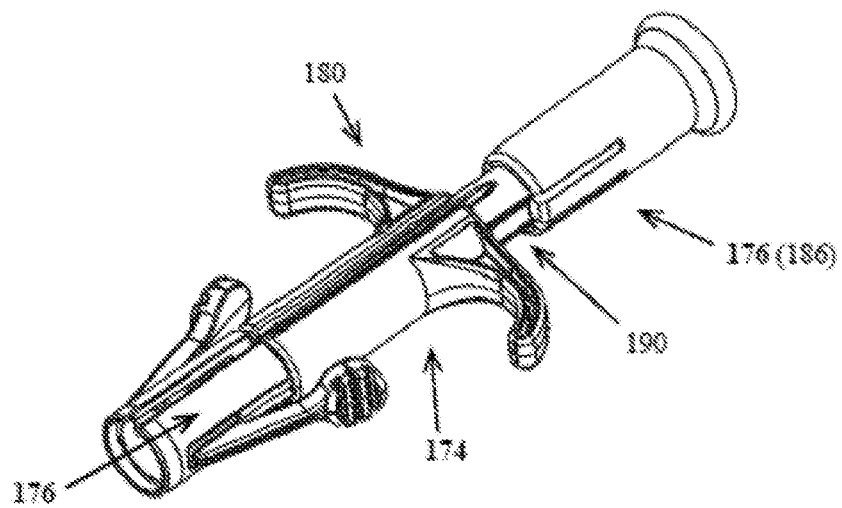
FIGS. 11C and 11D are schematic perspective views of the exemplary embodiment of the hole forming actuator of FIG. 11B, in a non-activated (non-actuated) configuration, in accordance with some embodiments of the invention.
Figure 11D:
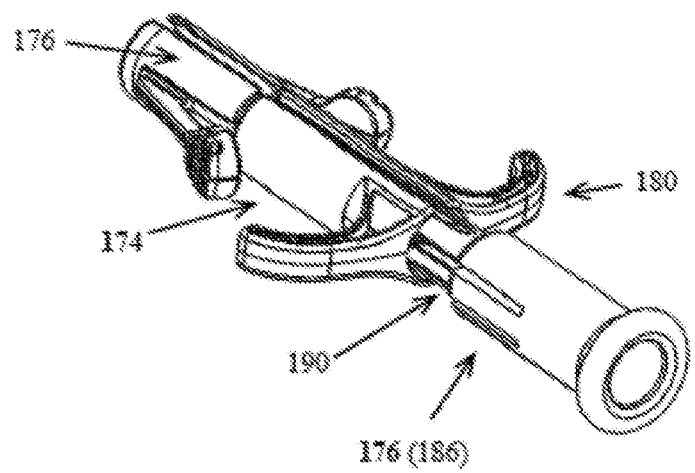

FIG. 11A is a schematic top view of an exemplary embodiment of hole forming actuator 104, highlighting outer and inner assemblies 174 and 176, respectively, thereof in an assembled (non-activated/non-actuated) configuration. FIG. 11B is a schematic side view of an exemplary embodiment of hole forming actuator 104, highlighting outer and inner assemblies 174 and 176, respectively, thereof in an assembled configuration, also showing non-activated (non-actuated) and activated (actuated) configurations, respectively, thereof. FIGS. 11C and 11D are schematic perspective views of the exemplary embodiment of hole forming actuator 104 of FIG. 11B, in a non-activated (non-actuated) configuration. FIGS. 11B, 11C, and 11D also include close up views of longitudinal slide slots 190 that additionally facilitate the relative linearly translatable motion of outer and inner assemblies 174 and 176, respectively. Specifically, outer assembly 174 is slidable within, and along, longitudinal slide slots 190 of inner assembly 176, via operation of the pair of manually controllable guiding members 180 (e.g., rigid finger grips) of outer assembly 174.

Figure 12A:
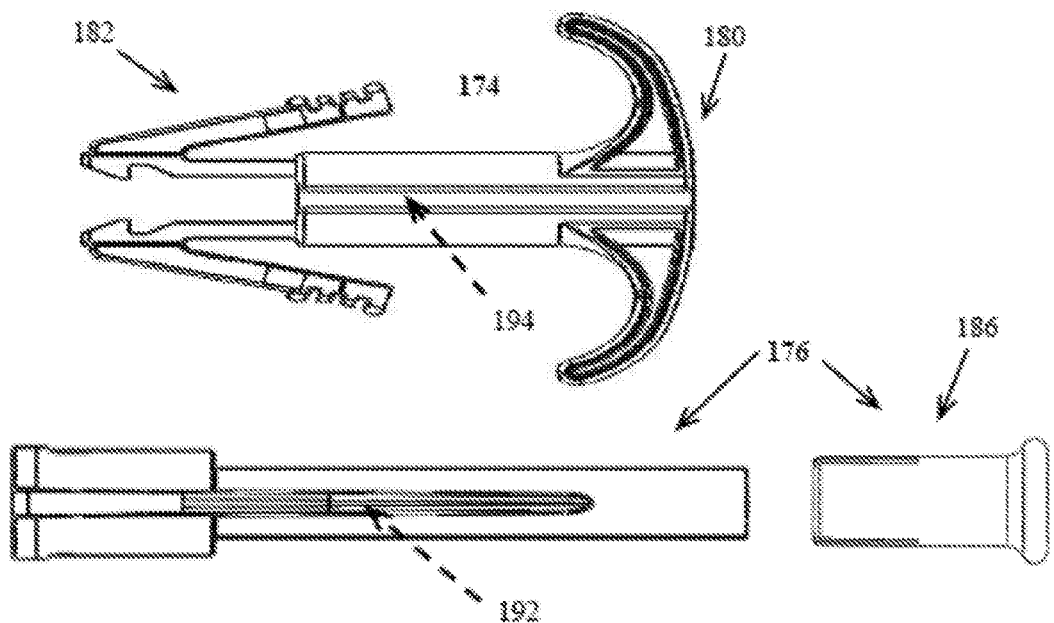
FIGS. 12A and 12B are schematic top and side views, respectively, of an exemplary embodiment of the hole forming actuator, highlighting individual outer and inner assemblies thereof in a non-assembled configuration, with the inner assembly having an exemplary slide-on type of cover, in accordance with some embodiments of the invention.
Figure 12B:
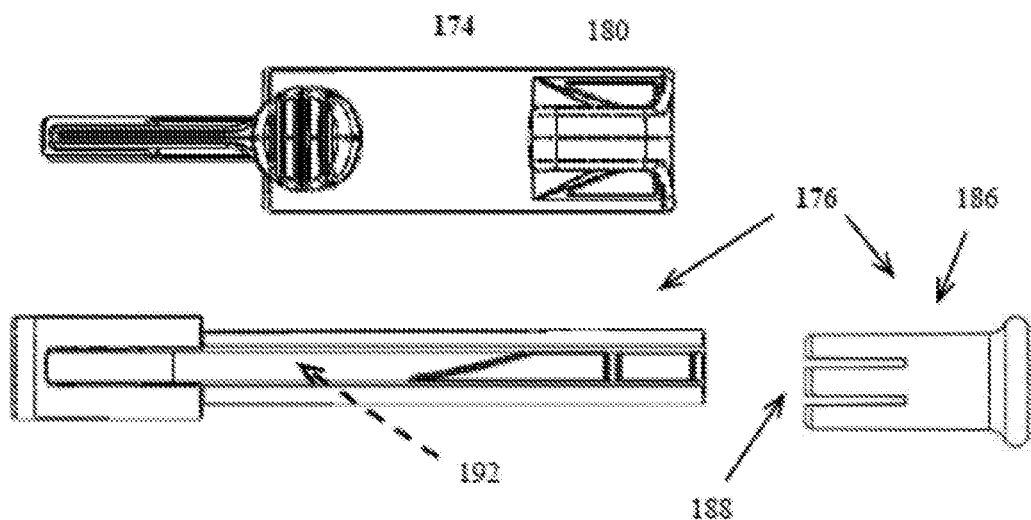

FIGS. 12A and 12B are schematic top and side views, respectively, of an exemplary embodiment of hole forming actuator 104, highlighting individual outer and inner assemblies 174 and 176, respectively, thereof in a non-assembled configuration, with the inner assembly having an exemplary slide-on type of cover 186. FIGS. 12A and 12B also include close up views of hole forming actuator dual assembly (or bi-assembly) longitudinal top slot [192+194], that is formed by, and includes, inner assembly longitudinal top slot 192, and outer assembly longitudinal top slot 194.

FIGS. 13A and 13B are schematic top and side views of another exemplary embodiment of the hole forming actuator (referenced as hole forming actuator 250), highlighting individual inner and outer assemblies 252 and 254, respectively, thereof in a non-assembled configuration. Inner and outer assemblies 252 and 254, respectively, are structurally and functionally essentially the same as inner and outer assemblies 176 and 174 (FIGS. 12A, 12B), respectively, except for the following two (relatively minor) structural differences. First, the proximal end portion of inner assembly 252 is configured with an exemplary screw-on type of cover 251, along with an accompanying pair of screws 253. This is in contrast to the slide-on type of cover 186 configured on the proximal end portion of inner assembly 176. Second, the distal end portion of outer assembly 254 is configured with a pair of oppositely (diametrically) positioned manually controllable connector members 256 (e.g., finger pressure activated elastic fasteners or latches) that include a smooth proximal end portion (absent of ridges). This is in contrast to the distal end portion of outer assembly 174 that is configured with a pair of connector member 182 that include a non-smooth, 'ridged', proximal end portion (having ridges). Similar to the function of connector members 182, connector members 256 facilitate manual operative reversible connection of the proximal end (i.e., outer protruding rim 164 of inner assembly 152) of anastomotic hole generating device 108 with the outer assembly distal end of hole forming actuator 104.

The numerous structural and functional (operational) characteristics and features of exemplary embodiments of hole forming actuator 104, and components thereof, are illustratively described above and are fully applicable to the exemplary embodiments shown in FIGS. 11A-13B.

As explained hereinabove, the hole forming actuator (104 or 250) is a component of the (overall) apparatus 100 for use in surgical vascular anastomotic procedures. In exemplary embodiments, the hole forming actuator (104 or 250) may also be considered as an individual 'stand-alone' apparatus. Accordingly, the hole forming actuator (104 or 250) apparatus corresponds to an exemplary particular 'sub-combination' of the (overall) apparatus 100 for use in surgical vascular anastomotic procedures, which, in turn, corresponds to another aspect of some embodiments of the present invention.

Figure 14:
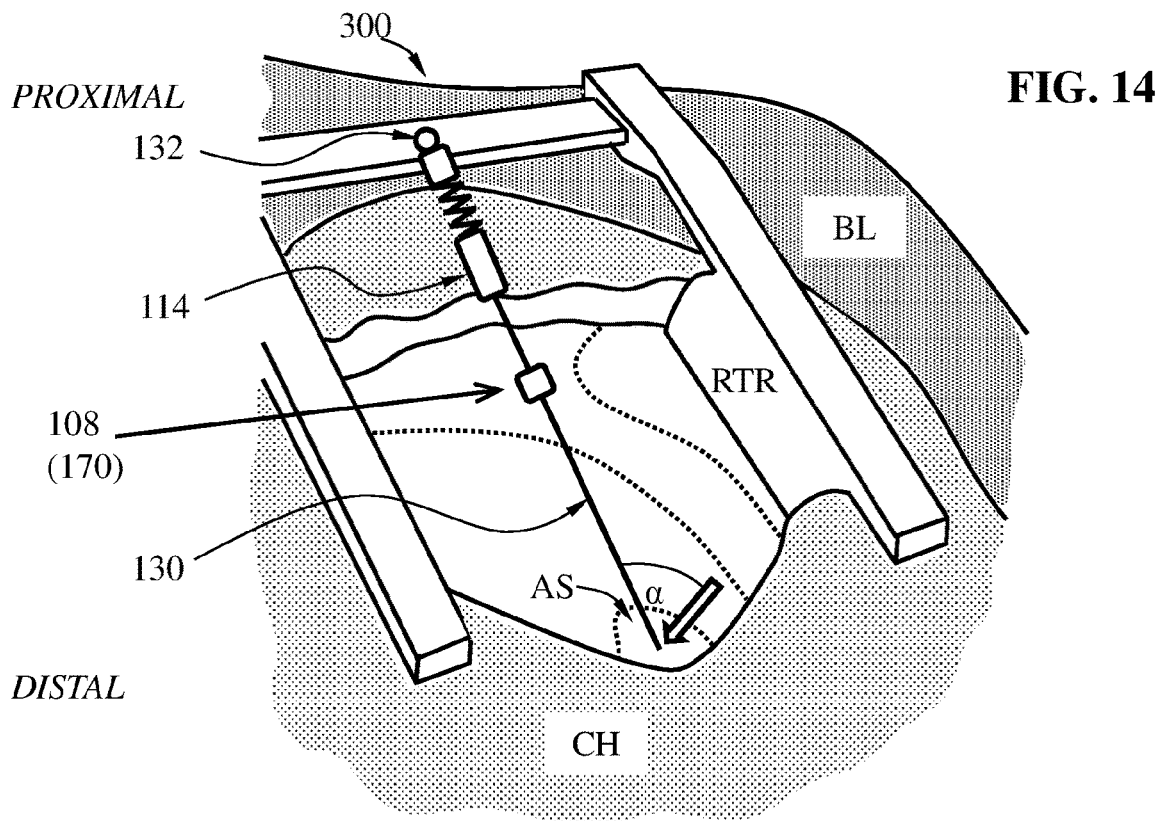
FIG. 14 is a schematic diagram showing an exemplary embodiment of using a (simplified) 'generic' version of the (overall) apparatus, for performing an exemplary vascular anastomotic procedure [(clampless) coronary artery bypass grafting (CABG)], highlighting use of the apparatus securing-anchoring assembly, in accordance with some embodiments of the invention.

FIG. 14 is a schematic diagram showing an exemplary embodiment of using a (simplified) 'generic' version of the (overall) apparatus 100, for performing an exemplary vascular anastomotic procedure, for example, (clampless) coronary artery bypass grafting (CABG), highlighting use of the apparatus securing-anchoring assembly 132.

In FIG. 14, exemplary apparatus 300 is deployed for sealing an anastomosis site AS, as part of a method for performing a surgical vascular anastomotic procedure, via securing (anchoring) apparatus 300 (and BVIW sealing and hole forming device 102 thereof), to a stable, stationary object (for example, fixed object 133) using securing-anchoring assembly 132. FIG. 14 illustrates an exemplary chest CH of a live subject (patient) during an open chest CABG surgery. Patient chest CH is kept open, for example, using a chest/sternum retractor RTR. The patient is partly covered with a blanket BL that is kept stable and secure to an operating room bed on which the patient lays.

In this illustrative example, manual hole sealing controller assembly 114 is fastened to retractor RTR using securing-anchoring assembly 132 at apparatus 300 proximal end PE, such that flexible tube 130 (with flexible control wire 128 inside) is in a taut stretched form under a chosen tensioning force. In exemplary embodiments, choosing the exact location for fastening securing-anchoring assembly 132 to a stable, stationary object (in this example, a portion of retractor RTR) is relevant to determining the tensioning force or/and the orientation of flexible tube 130 (with flexible control wire 128). This, in turn, is done to optimize moving, guiding and positioning hole generating member 170 of anastomotic hole generating device 108, and forming (adjusting) and setting an angular orientation angle (herein, referred to as angular orientation angle α) that flexible tube 130 forms relative to a normal to surface of the target anastomosis site AS. The heart surgeon performing the anastomotic procedure may prefer an angular orientation angle α corresponding to a close to normal angular orientation (for example, 0≤angular orientation angle α≤15°) projecting, for example, from the anastomosis site AS, in order to adjust (change) aspects or/and characteristics of the peripheral sealing procedure, or the surgeon may prefer a shallower angular orientation (for example, 45°<angular orientation angle α<90°) if the surgeon prefers to diminish possible physical interference by flexible tube 130 with the anastomotic suturing process. In exemplary embodiments, the surgeon may use any angular orientation angle α, for example, an in between angular orientation angle α (0°<angular orientation angle α<90°), as determined to be appropriate.

Figure 15:
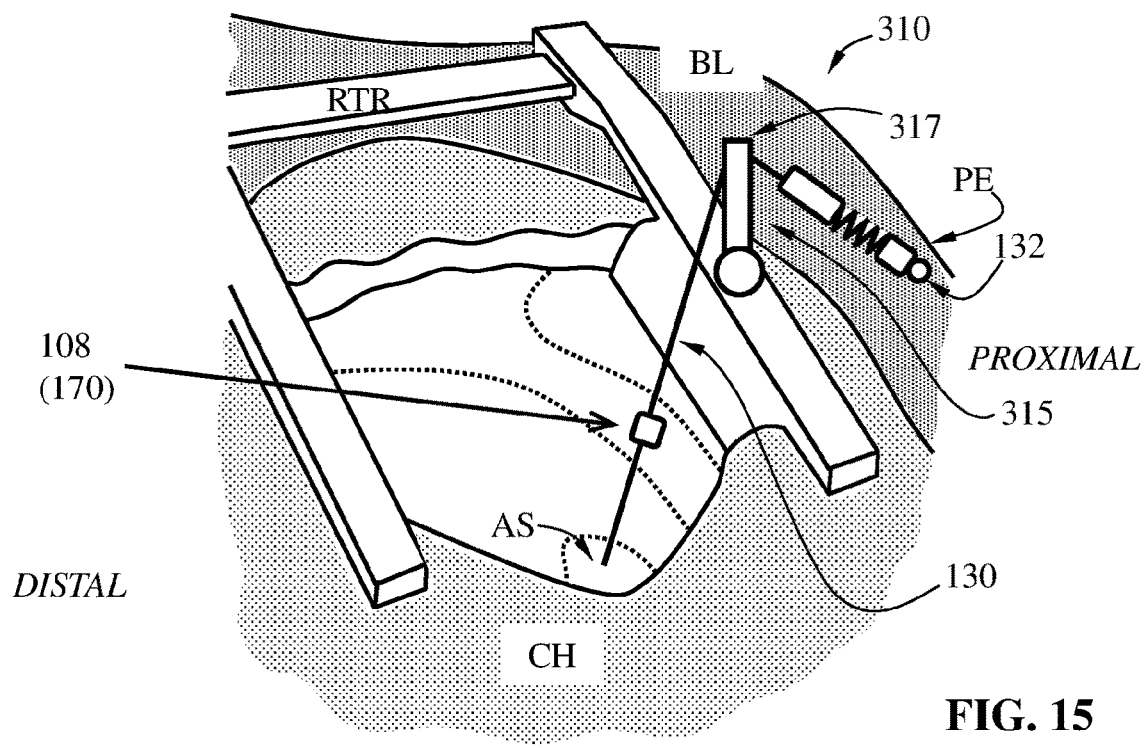
FIGS. 15, and 16A-16B are schematic diagrams showing exemplary embodiments of using another (simplified) 'generic' version of the (overall) apparatus, for performing an exemplary vascular anastomotic procedure [(clampless) coronary artery bypass grafting (CABG)], highlighting use of another exemplary apparatus securing-anchoring assembly, in accordance with some embodiments of the invention.
Figure 16A:
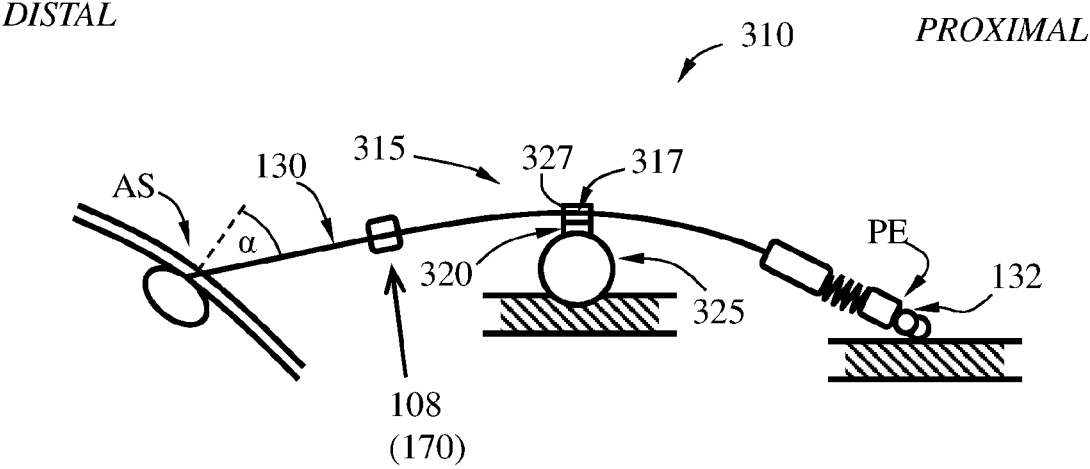
Figure 16B:
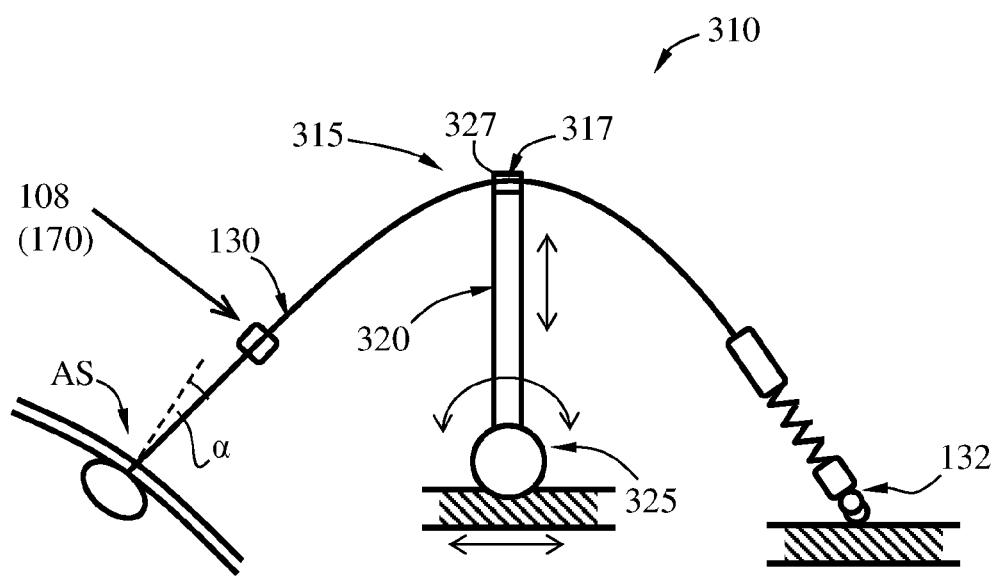

FIGS. 15, and 16A-16B are schematic diagrams showing exemplary embodiments of using another (simplified) 'generic' version of the (overall) apparatus 100, for performing an exemplary vascular anastomotic procedure [(clampless) coronary artery bypass grafting (CABG)], highlighting use of another exemplary apparatus securing-anchoring assembly 315.

In these figures, exemplary apparatus 310 is deployed for sealing an anastomosis site AS, as part of a method for performing a surgical vascular anastomotic procedure, via securing (anchoring) apparatus 310 (and BVIW sealing and hole forming device 102 thereof), to another exemplary stable, stationary object using another exemplary securing-anchoring assembly.

In order to improve controllability of tension, or/and angular orientation angle α, at least one other portion or point along flexible tube 130 (with flexible control wire 128 inside) may be anchored, secured, or further tensioned, instead of, or in addition to, use of securing-anchoring assembly 132 at apparatus 310 proximal end PE. FIGS. 15, and 16A-16B schematically illustrate exemplary apparatus 310 deployed, using another exemplary securing-anchoring assembly that includes a tensioner 315 configured to create or increase tension by forcing a chosen point 317 along flexible tube 130 in a chosen tensioning direction.

Tensioner 315 includes a tensioning pole 320 fixedly configurable in a chosen length or/and direction relative to a stable, stationary object (fixed object 133). Tensioning pole 320 has a pole base 325 that is fixedly connectable to the stable object, and a pole head 327 that is configured to anchor or/and pole (pivot) a portion of flexible tube 130, for example supporting chosen point 317, by pressing that portion of flexible tube 130 with pole head 327 in a chosen direction and force. Angular orientation angle α can be determined using tensioner 315 by configuring and setting one or more of the following parameters: (i) the location of point 317 along flexible tube 130, or/and (ii) the location of the stable object relative to anastomosis site AS, or/and (iii) the chosen direction which can be set with rotating pole head 327 relative to pole base 325, or/and (iv) the chosen force applied by tensioner 315 to flexible tube 130 at point 317, which can be set with changing height of tensioning pole 320. FIG. 15 illustrates an exemplary scenario in which tensioner 315 is fixated (fixedly connected) to retractor RTR and securing-anchoring assembly 132 is fixated (fixedly connected) to secured blanket BL (in this example, both retractor RTR and blanket BL are considered exemplary stationary, stable objects). Tensioning pole 320 is selectively, gradually, or sequentially, configured to move (via pressing) a portion of flexible tube 130 with pole head 327, so as to apply a chosen tensioning force, for example, as illustrated in FIGS. 16A and 16B.

Medical Device Kits for Use in Surgical Vascular Anastomotic Procedures

An aspect of some embodiments of the present invention is a medical device kit for use in surgical vascular anastomotic procedures. Various different alternative embodiments, and options thereof, of the medical device kit are possible, each of which is suitable for a medical practitioner (surgeon, surgeon's assistant, medical technician) to readily deploy and use in a surgical vascular anastomotic procedure.

First Exemplary Embodiment of a Medical Device Kit

A first exemplary embodiment of a medical device kit corresponds to the exemplary embodiment of the (overall) apparatus 100 illustratively described above and shown in FIG. 1. Such a first exemplary embodiment of a medical device kit includes: blood vessel inner wall (BVIW) sealing and hole forming device 102 (which, in turn, includes hole sealing device 106, and anastomotic hole generating device 108), and hole forming actuator 104. According to such a first exemplary embodiment of a medical device kit (i.e., apparatus 100), as shown in FIG. 1, anastomotic hole generating device 108 is provided already positioned (i.e., assembled, mounted) on hole sealing device 106. According to such a first exemplary embodiment of a medical device kit, BVIW sealing and hole forming device 102 (via anastomotic hole generating device 108) and hole forming actuator 104 are connectable to each other for deployment and use in a surgical vascular anastomotic procedure.

Second Exemplary Embodiment of a Medical Device Kit

A second exemplary embodiment, and options thereof, of a medical device kit, is shown in FIG. 17 and referred to as medical device kit 400. According to a first option, medical device kit 400 includes: hole sealing device 106, and anastomotic hole generating device 108, without (optional) hole forming actuator 104. According to such a first option of medical device kit 400, anastomotic hole generating device 108 is provided separated from (i.e., non-assembled, non-mounted on) hole sealing device 106. Anastomotic hole generating device 108 is positionable (i.e., assemblable, mountable) on hole sealing device 106, for example, as indicated in FIG. 17 by the dashed line double-headed (bi-directional) arrow 405.

According to a second option, medical device kit 400, optionally, further includes (optional) hole forming actuator 104. According to such a second option, anastomotic hole generating device 108 and hole forming actuator 104 are provided non-connected to each other, and are connectable to each other for deployment and use in a surgical vascular anastomotic procedure.

Third Exemplary Embodiment of a Medical Device Kit

A third exemplary embodiment of a medical device kit is shown in FIG. 18, and referred to as medical device kit 410. Medical device kit 410 includes: hole sealing device 106, anastomotic hole generating device 108, and hole forming actuator 104, wherein anastomotic hole generating device 108 and hole forming actuator 104 are provided (reversibly) connected to each other. According to such a third exemplary embodiment of a medical device kit, anastomotic hole generating device 108 and hole forming actuator 104 are unconnectable from each other, so as to facilitate positioning (i.e., assembling, mounting) of anastomotic hole generating device 108 onto hole sealing device 106 for deployment and use in a surgical vascular anastomotic procedure. Thereafter, anastomotic hole generating device 108 and hole forming actuator 104 are connectable to each other during the surgical vascular anastomotic procedure.

Exemplary Implementations and Methods

As stated hereinabove, the present invention, in exemplary embodiments thereof, includes the following aspects. A method for use in surgical vascular anastomotic procedures. A method for forming an anastomotic hole in a blood vessel inner wall segment. A method for performing surgical vascular anastomosis. Hereinabove illustrative description of characteristics and technical features of the apparatus for use in surgical vascular anastomotic procedures, or of a component (e.g., device, assembly) of the apparatus, also relates to, and is fully applicable for, illustratively describing characteristics and technical features of one or more of these other aspects of the present invention. Additionally, embodiments of the apparatus for use in surgical vascular anastomotic procedures, or of a component (e.g., device, assembly) of the apparatus, are suitable for implementing embodiments of a method for use in surgical vascular anastomotic procedures, or/and for implementing embodiments of a method for forming an anastomotic hole in a blood vessel inner wall segment, or/and for implementing embodiments of a method for performing surgical vascular anastomosis.

FIGS. 19A-19K are schematic views of exemplary embodiments of sequential steps (procedures) of implementing the herein disclosed apparatus (and components thereof) for use in surgical vascular anastomotic procedures. Throughout FIGS. 19A-19K, several of the reference numbers are the same as those used throughout the above illustrative description, and refer to same characteristics or features. Following is illustrative description FIG. 19A highlights that an exemplary blood vessel BV, for example, an aorta, is selected for deploying apparatus 100 for use in a surgical vascular anastomotic procedure (e.g., an end-to-side type of surgical vascular anastomotic procedure). A small hole [not incision] SH is made (for example, manually, using a needle or syringe NS) in the blood vessel BV, for example, the aorta, at the desired anastomosis site located along a blood vessel inner wall segment BVIWS. The small (needle or syringe sized) hole has a diameter, for example, of about 1 mm or less.

FIG. 19B highlights that anastomotic hole generating device 108 sheath 112 (with hole sealing assembly 112, in a non-activated, collapsed configuration) inside, is inserted through the small hole SH in the blood vessel BV and into the blood vessel lumen BVL.

FIG. 19C highlights that hole sealing assembly 112 is activated (actuated) to an activated, self-expanded configuration, via operation of hole sealing device 106 (FIGS. 5A, 5B), and proximally pulled against the blood vessel inner wall BVIW, along with blood vessel inner wall segment, so as to establish a peripheral seal PS around the blood vessel inner wall segment BVIWS.

FIG. 19D highlights that apparatus 100 is operated, with activation, moving, guiding, and positioning, of anastomotic hole generating member 170 relative to the blood vessel inner wall segment BVIWS, for example, as described above and also shown in FIGS. 14, 15A, 15B. Anastomotic hole generating member 170 is inserted through the small hole SH along the blood vessel inner wall segment BVIWS. Hole sealing assembly 112 is operated to atraumatically establish and maintain a peripheral seal PS along the blood vessel inner wall segment BVIWS, in the absence of blood flow (from the blood vessel lumen).

FIG. 19E highlights that apparatus 100 is operated, particularly, for facilitating anastomotic hole generating member 170 to atraumatically generate an anastomotic hole AH with a diameter of about 4-5 mm, depending upon the conic diameter of the anastomotic hole generating member 170. Anastomotic hole generating member 170 is proximally pulled back into the hole generating device outer assembly 150, along with the small piece P of tissue removed from the aorta blood vessel wall BVW along the blood vessel inner wall segment BVIWS.

FIG. 19F highlights that apparatus 100 is operated, particularly, for facilitating return of anastomotic hole generating device 108 (and anastomotic hole generating member 170 therein) to a 'relaxed' non-activated configuration. There is maintaining the peripheral seal PS along the blood vessel inner wall segment, in the absence of blood flow.

Figure 19H:
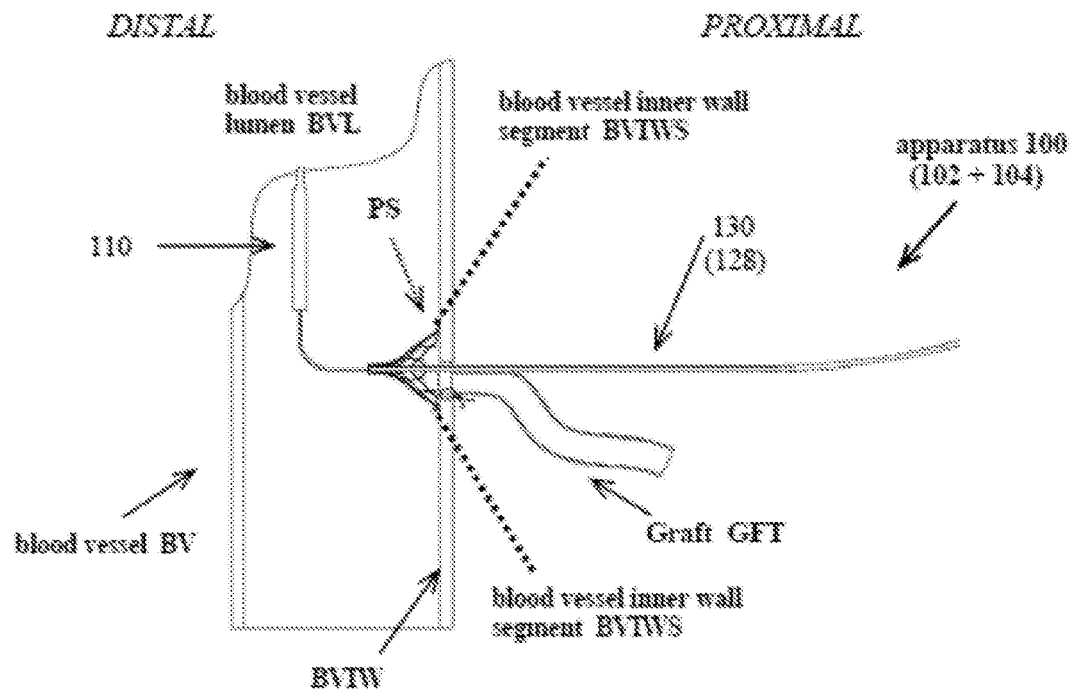

FIGS. 19G-19H highlight that after established, and while maintaining, the peripheral seal PS along the blood vessel inner wall segment BVIWS, in the absence of blood flow, there is starting the surgical vascular anastomotic procedure. This includes suturing of a blood vessel graft GFT to the blood vessel wall BVW within the anastomosis site.

Figure 19I:
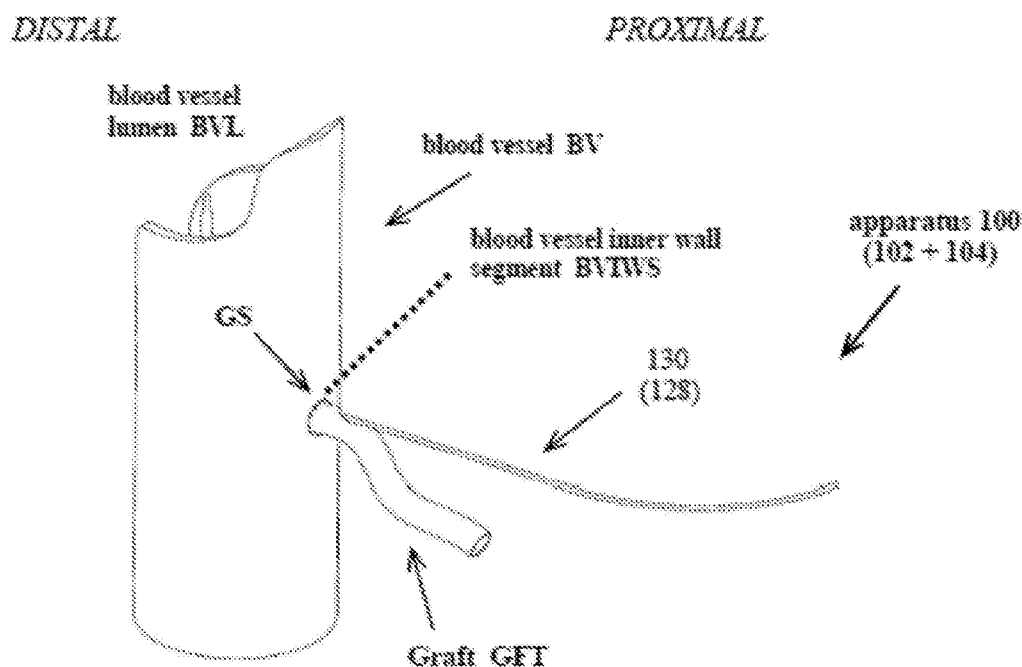

FIG. 19I highlights that there is completing nearly all of the graft sutures GS of the blood vessel graft GFT to the blood vessel wall within the anastomosis site, while the hole sealing assembly 112 is still inside the blood vessel lumen BVL, along the blood vessel inner wall segment BVIWS.

Figure 19J:
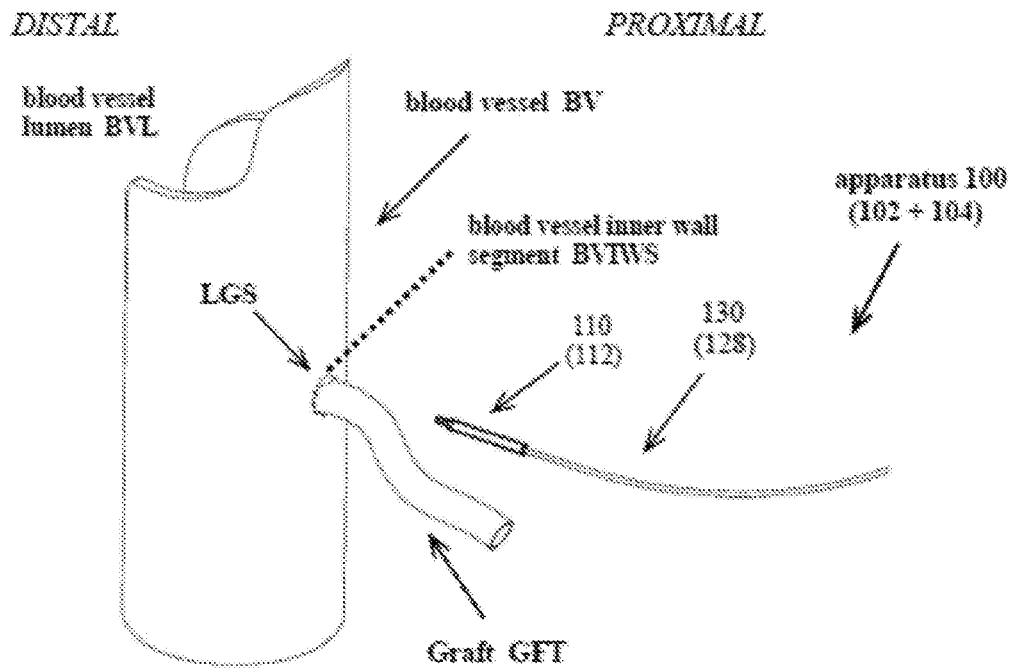

FIG. 19J highlights that just before completing the last graft suture LGS of the graft GFT, there is removing the sheath 110 (with the hole sealing assembly 112 inside, in a non-activated, collapsed configuration) from the blood vessel BV.

Figure 19K:
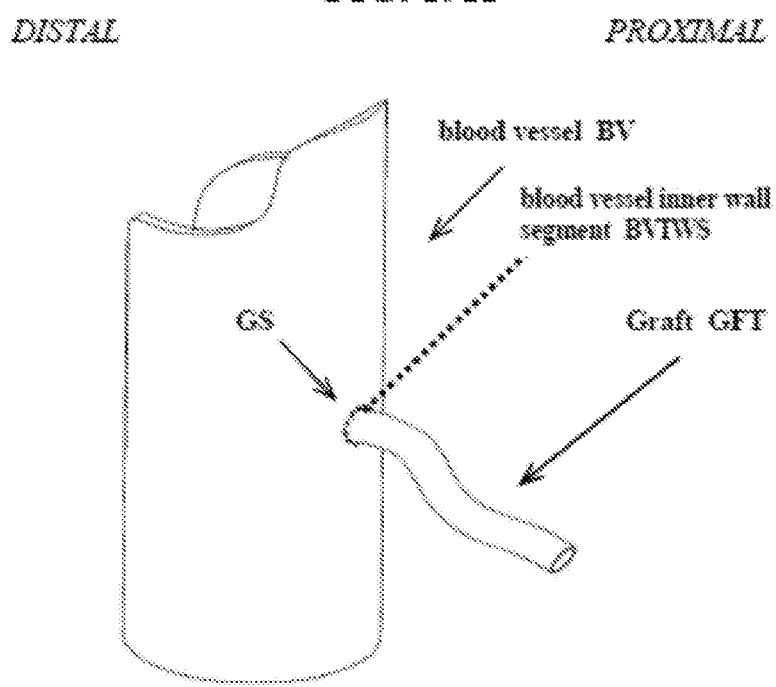

FIG. 19K highlights suturing of the last graft suture LGS of the graft GFT to the blood vessel BV, and completing the anastomotic procedure.

Following are additional steps (procedures) involved in implementing embodiments of the invention, along with reference to the drawings.

There is providing apparatus 100 to a trained medical practitioner, for example, a surgeon and a surgical team.

There is sterilizing, for example, by washing in saline solution, the apparatus 100 components, particularly, BVIW sealing and hole forming device 102 and hole forming actuator 104.

There is preparing a subject (patient) for a surgical vascular anastomotic procedure. This includes, making a small hole SH [not incision] (for example, manually, using a needle or syringe) in the blood vessel BV, for example, the aorta, at the desired anastomosis site located along a blood vessel inner wall segment BVIWS, prior to insertion of anastomotic hole generating device 108 into the subject.

There is deploying (pacing) BVIW sealing and hole forming device 102 at and in a selected location, along the blood vessel inner wall segment BVIWS, in the prepared subject. This includes inserting anastomotic hole generating device 108 sheath 112 (with hole sealing assembly 112, in a non-activated, collapsed configuration inside) through the small hole SH in the blood vessel BV and into the blood vessel lumen BVL.

There is connecting manual hole sealing controller assembly 114 to anastomotic hole generating device 108, to provide a firm base for activating the hole sealing assembly 112.

There is operating manual hole sealing controller assembly 114 (and flexible control wire 128) to remove sheath 110 from hole sealing assembly 112, thereby, facilitating activation of hole sealing assembly 112 from a non-activated, collapsed configuration to an activated, self-expanded configuration.

While hole sealing assembly 112 is in the activated, self-expanded configuration, there is pulling hole sealing assembly 112 towards to blood vessel inner wall BVIW, along the blood vessel inner wall segment BVIWS, so as to establish the peripheral seal around the blood vessel inner wall segment BVIWS. Then, there is disconnecting anastomotic hole generating device 108 from manual hole sealing controller assembly 114.

There is distally moving anastomotic hole generating device 108, to make room for connection of hole forming actuator 104 to anastomotic hole generating device 108.

There is connecting hole forming actuator 104 to anastomotic hole generating device 108 (via flanges 156 and 164) and also to flexible tube 130, for setting up eventual generating of the anastomotic hole.

There is using hole forming actuator 104 to activate anastomotic hole generating device 108 (and anastomotic hole generating member 170) to atraumatically generate an anastomotic hole in the blood vessel inner wall, along the blood vessel inner wall segment BVIWS. This step (procedure) includes distally pushing hole forming actuator guiding members (finger grips) 180 to atraumatically distally move anastomotic hole generating device inner assembly 152 (including anastomotic hole generating member 170) through the small (needle or syringe sized) hole SH made by the surgeon. This step (procedure) also includes proximally pulling hole forming actuator guiding members (finger grips) 180 to generate an anastomotic hole AH in, and through, the blood vessel inner wall, along the blood vessel inner wall segment BVIWS.

There is disconnecting hole forming actuator 104 from anastomotic hole generating device 108, and from flexible tube 130, and placing hole forming actuator 104 on the side (since it is no longer needed).

There is re-connecting manual hole controller assembly 114 to anastomotic hole generating device 108, in preparation for suturing of a blood vessel graft GFT to the blood vessel wall at the anastomosis site.

There is performing the anastomotic procedure, leaving open one or two last graft sutures LGS of the graft GFT, to facilitate removing of sheath 110 (with hole sealing assembly 112 in a non-activated, collapsed configuration) from the anastomotic hole.

There is operating manual hole sealing controller assembly 114 to proximally pull sheath 110 back onto hole sealing assembly 112, so as to return hole sealing assembly 112 to a non-activated, collapsed configuration, prior to removal of sheath 110 from the blood vessel BVL. Then, there is removing BVIW sealing and hole forming device 102 from the subject, followed by completing the last graft suture LGS of the graft GFT to the blood vessel BV, and completing the anastomotic procedure.

Exemplary Materials of Construction and Size Dimensions of Components of the Apparatus for Use in Surgical Vascular Anastomotic Procedures Sheath 110

Pebax® polymeric resin; PTFE (polytetrafluoroethylene); stainless steel braid wire.

Outer diameter: about 2 mm. Inner diameter: about 1.7 mm. Overall height: about 25 mm.

Hole Sealing Assembly 112

Frame: nitinol; cobalt; chrome.

Frame (strut) covering: thermoplastic polyurethane; thermoplastic silicone.

Frame (strut) thickness: about 0.23 mm. Frame (strut) width: about 0.14 mm. Frame (neck) outer diameter: about 1.5 mm. Frame (neck) inner diameter: about 1.0 mm. Frame (flare): about 15.0 mm. Frame covering thickness: about 20 microns. Frame (flare) covering outer diameter: about 16 mm.

Manual Hole Sealing Controller Assembly 114

Manual control knob: polycarbonate Makrolon® 2458; POM (polyoxymethylene); nylon 66; size: about 10 mm×7 mm×3 mm.

Hand-holdable housing assembly: polycarbonate Makrolon® 2458; polyoxymethylene; nylon 66; handle length: about 13 mm; handle diameter: about 9 mm.

Flexible control wire: nitinol; cobalt; chrome. Diameter: about 0.3 mm. Length: about 350-400 mm.

Flexible tube: PEEK (polyether ether ketone); POM (polyoxymethylene; Pebax® polymeric resin. Outer diameter: about 0.8 mm. Inner diameter: about 275 mm.

Securing-anchoring assembly: silicone. Thickness: about 1.8 mm. Length: about 65 mm.

Anastomotic Hole Generating Device 108

Outer assembly: stainless steel 304; outer diameter: about 9 mm; inner diameter: about 4 mm; length: about 22 mm.

Inner assembly: stainless steel 304; length: about 37 mm; main diameter: about 4 mm; conic anastomotic hole generating member diameter: about 1 mm; shoulder diameter: about 10 mm.

Hole Forming Actuator 104

Outer assembly: polycarbonate Makrolon® 2458; POM (polyoxymethylene); nylon 66.

Handle length: about 115 mm. Handle width: about 55 mm. Handle diameter: about 20 mm.

Inner assembly: polycarbonate Makrolon® 2458; POM (polyoxymethylene); nylon 66. Handle length: about 95 mm. Handle diameter: about 14 mm.

Each of the following terms written in singular grammatical form: 'a', 'an', and 'the', as used herein, means 'at least one', or 'one or more'. Use of the phrase 'one or more' herein does not alter this intended meaning of 'a', 'an', or 'the'. Accordingly, the terms 'a', 'an', and 'the', as used herein, may also refer to, and encompass, a plurality of the stated entity or object, unless otherwise specifically defined or stated herein, or, unless the context clearly dictates otherwise. For example, the phrases: 'a unit', 'a device', 'an assembly', 'a mechanism', 'a component', 'an element', and 'a step or procedure', as used herein, may also refer to, and encompass, a plurality of units, a plurality of devices, a plurality of assemblies, a plurality of mechanisms, a plurality of components, a plurality of elements, and, a plurality of steps or procedures, respectively.

Each of the following terms: 'includes', 'including', 'has', 'having', 'comprises', and 'comprising', and, their linguistic/grammatical variants, derivatives, or/and conjugates, as used herein, means 'including, but not limited to', and is to be taken as specifying the stated component(s), feature(s), characteristic(s), parameter(s), integer(s), or step(s), and does not preclude addition of one or more additional component(s), feature(s), characteristic(s), parameter(s), integer(s), step(s), or groups thereof. Each of these terms is considered equivalent in meaning to the phrase 'consisting essentially of'.

The term 'method', as used herein, refers to a single step, procedure, manner, means, or/and technique, or a sequence, set, or group of two or more steps, procedures, manners, means, or/and techniques, for accomplishing or achieving a given task or action. Any such herein disclosed method, in a non-limiting manner, may include one or more steps, procedures, manners, means, or/and techniques, that are known or readily developed from one or more steps, procedures, manners, means, or/and techniques, previously taught about by practitioners in the relevant field(s) and art(s) of the herein disclosed invention. In any such herein disclosed method, in a non-limiting manner, the stated or presented sequential order of one or more steps, procedures, manners, means, or/and techniques, is not limited to that specifically stated or presented sequential order, for accomplishing or achieving a given task or action, unless otherwise specifically defined or stated herein, or, unless the context clearly dictates otherwise. Accordingly, in any such herein disclosed method, in a non-limiting manner, there may exist one or more alternative sequential orders of the same steps, procedures, manners, means, or/and techniques, for accomplishing or achieving a same given task or action, while maintaining same or similar meaning and scope of the herein disclosed invention.

Throughout this disclosure, a numerical value of a parameter, feature, characteristic, object, or dimension, may be stated or described in terms of a numerical range format. Such a numerical range format, as used herein, illustrates implementation of some exemplary embodiments of the invention, and does not inflexibly limit the scope of the exemplary embodiments of the invention. Accordingly, a stated or described numerical range also refers to, and encompasses, all possible sub-ranges and individual numerical values (where a numerical value may be expressed as a whole, integral, or fractional number) within that stated or described numerical range. For example, a stated or described numerical range 'from 1 to 6' also refers to, and encompasses, all possible sub-ranges, such as 'from 1 to 3', 'from 1 to 4', 'from 1 to 5', 'from 2 to 4', 'from 2 to 6', 'from 3 to 6', etc., and individual numerical values, such as '1', '1.3', '2', '2.8', '3', '3.5', '4', '4.6', '5', '5.2', and '6', within the stated or described numerical range of 'from 1 to 6'. This applies regardless of the numerical breadth, extent, or size, of the stated or described numerical range.

Moreover, for stating or describing a numerical range, the phrase 'in a range of between about a first numerical value and about a second numerical value', is considered equivalent to, and meaning the same as, the phrase 'in a range of from about a first numerical value to about a second numerical value', and, thus, the two equivalently meaning phrases may be used interchangeably. For example, for stating or describing the numerical range of room temperature, the phrase 'room temperature refers to a temperature in a range of between about 20° C. and about 25° C.', is considered equivalent to, and meaning the same as, the phrase 'room temperature refers to a temperature in a range of from about 20° C. to about 25° C.'.

The term 'about', as used herein, refers to ±10% of the stated numerical value.

The phrase 'operatively connected', as used herein, equivalently refers to the corresponding synonymous phrases 'operatively joined', and 'operatively attached'. These phrases, as used herein, mean that the described or/and shown entities are configured 'connected' to each other, in an 'operative' (ready-for-operation/ready-for-use) manner. Such operative connection, operative joint, or operative attachment, between or among the entities is according to one type, or a plurality of types, of a mechanical (physical, structural), or/and an electrical, or/and an electronic, or/and an electro-mechanical, connection or connections, involving one or more corresponding type(s) or kind(s) of mechanical (physical, structural), or/and electrical, or/and electronic, or/and electro-mechanical, equipment and components. Optionally, such operative connection, operative joint, or operative attachment, between or among the entities, may include, or may involve, one or more type(s) or kind(s) of computerized hardware or/and software equipment and components.

The phrase 'operably connectable', as used herein, equivalently refers to the corresponding synonymous phrases 'operably joinable to', and 'operably attachable to'. These phrases, as used herein, mean that the described or/and shown entities are configured 'connectable' to each other (i.e., capable of being connected to each other, having ability to be connected to each other, or having potential to be connected to each other), for subsequently forming an 'operative connection', an 'operative joint', or an 'operative attachment', between or among the entities. Such operable connectability, operable joinability, or operable attachability, between or among the entities is according to one type, or a plurality of types, of a mechanical (physical, structural), or/and an electrical, or/and an electronic, or/and an electro-mechanical, connection or connections, involving one or more corresponding type(s) or kind(s) of mechanical (physical, structural), or/and electrical, or/and electronic, or/and electro-mechanical, equipment and components. Optionally, such operable connectability, operable joinability, or operable attachability, between or among the entities, may include, or may involve, one or more type(s) or kind(s) of computerized hardware or/and software equipment and components.

It is to be fully understood that certain aspects, characteristics, and features, of the invention, which are, for clarity, illustratively described and presented in the context or format of a plurality of separate embodiments, may also be illustratively described and presented in any suitable combination or sub-combination in the context or format of a single embodiment. Conversely, various aspects, characteristics, and features, of the invention which are illustratively described and presented in combination or sub-combination in the context or format of a single embodiment, may also be illustratively described and presented in the context or format of a plurality of separate embodiments.

Although the invention has been illustratively described and presented by way of specific exemplary embodiments, and examples thereof, it is evident that many alternatives, modifications, or/and variations, thereof, will be apparent to those skilled in the art. Accordingly, it is intended that all such alternatives, modifications, or/and variations, are encompassed by the broad scope of the appended claims.

All publications, patents, and or/and patent applications, cited or referred to in this disclosure are herein incorporated in their entirety by reference into the specification, to the same extent as if each individual publication, patent, or/and patent application, was specifically and individually indicated to be incorporated herein by reference. In addition, citation or identification of any reference in this specification shall not be construed or understood as an admission that such reference represents or corresponds to prior art of the present invention. To the extent that section headings are used, they should not be construed as necessarily limiting.

The invention claimed is:

1. An apparatus for use in surgical vascular anastomotic procedures, comprising:
   a blood vessel inner wall sealing and hole forming device, configured to atraumatically establish and maintain, inside a blood vessel lumen, along a blood vessel inner wall segment thereof, a peripheral seal around a needle sized hole in said blood vessel inner wall segment, absent of blood flow, and to form an anastomotic hole through said peripherally sealed blood vessel inner wall segment, in said blood flow absence;
   and a hole forming actuator, reversibly connectable to, and configured for operating, said blood vessel inner wall sealing and hole forming device;
   wherein said blood vessel inner wall sealing and hole forming device includes a hole sealing device, configured to atraumatically establish said peripheral seal, and comprising:
   a hole sealing assembly, having a reversibly expandable non-activated, collapsed configuration and a reversibly collapsible activated, self-expanded configuration;
   a sheath that externally fully covers, closely fits over, and holds said hole sealing assembly said reversibly expandable non-activated, collapsed configuration, and configured to atraumatically entirely, with said hole sealing assembly in said collapsed configuration, enter into said blood vessel lumen, by passing through said needle sized hole and along said blood vessel inner wall segment;
   a manual hole sealing controller assembly, operably connected to said sheath, and configured to facilitate manual control of said hole sealing assembly and said sheath;
   a flexible control wire, having a distal end fixedly connected to an inside distal end of said sheath, and having a proximal portion fixedly connected to an inside distal portion of said manual hole sealing controller assembly, and configured to control motion and positioning of said sheath and reversible activation of said hole sealing assembly; and
   a flexible tube, that encloses, holds, and guides motion of said flexible control wire.

2. The apparatus of claim 1, wherein said hole sealing assembly, in both of in said reversibly expandable non-activated, collapsed configuration and reversibly collapsible activated, self-expanded configuration, has a tubular distal end portion neck or apex connected to only a distal end of said flexible tube that holds said flexible control wire inside, so as to facilitate said flexible control wire to distally pass through said flexible tube and distally remove said sheath from said hole sealing assembly, thereby activating said hole sealing assembly to said reversibly collapsible activated, self-expanded configuration.

3. The apparatus of claim 1, wherein said sheath is configured as a tubular member having a main portion whose proximal end is opened, and a conical distal end portion whose distal end or apex is closed and has a maximum outer diameter being less than an outer diameter of said main portion and less than a diameter of said needle sized hole in said blood vessel inner wall segment.

4. The apparatus of claim 3, wherein, when said hole sealing assembly is in said reversibly collapsible activated, self-expanded configuration, the opened proximal end of said sheath main portion is a distance, of at least a few millimeters, and up to a few centimeters, away from a distal end of said hole sealing assembly.

5. The apparatus of claim 1, wherein said manual hole sealing controller assembly is configured as a hand-holdable module that includes: a manual control knob configured to be manually operable and linearly translatable via finger pushing or pulling thereof, and a hand-holdable housing assembly configured with a linear slot, narrow groove, or channel, within, said manual control knob is manually operable and linearly translatable along the linear slot, narrow groove, or channel.

6. The apparatus of claim 1, wherein said manual hole sealing controller assembly includes a securing-anchoring assembly that is configured to facilitate reversible securing and anchoring of a proximal end portion of said hole sealing device; via connecting said proximal end portion of said hole sealing device, and a proximal end portion of said manual hole sealing controller assembly therein, to a stable, stationary object, and disconnecting said proximal end portion of said hole sealing device, and a proximal end portion of said manual hole sealing controller assembly, from said stable, stationary object when said reversible securing and anchoring of the proximal end portion of said hole sealing device are no longer necessary.

7. The apparatus of claim 6, wherein said securing-anchoring assembly is configured as a single, integral flexible, elastic strap, rod, or bar type of structure, having a middle or central portion, a distal end portion fixedly connected to an inside of said manual hole sealing controller assembly, and a proximal end portion reversibly securable and anchorable to said stable, stationary object.

8. The apparatus of claim 6, wherein said securing-anchoring assembly is configured as a spring type mechanism that includes a tension spring operatively connected with a securing-anchoring member pin or rod whose proximal end is configured as a fastener or latch to reversibly connect, secure, and anchor said proximal end portion of said manual hole sealing controller assembly to said stable, stationary object, and to disconnect said proximal end portion of said manual sealing controller assembly from said stable, stationary object when said reversible securing and anchoring of the proximal end portion of said hole sealing device are no longer necessary.

9. The apparatus of claim 1, wherein said flexible control wire, inside of said flexible tube via manual operation of said manual hole sealing controller assembly, is linearly translatable and slidably movable forward and backward in distal and proximal directions between proximal and distal portions of said hole sealing device.

10. The apparatus of claim 1, wherein said flexible control wire includes a distal end portion outside of said flexible tube, via manual operation of said manual hole sealing controller assembly, that is non-linearly translatable and slidably movable forward and backward in distal and proximal directions between a tubular distal end portion neck or apex distal end of said hole sealing assembly and an opened proximal end of said sheath.

11. The apparatus of claim 10, wherein said distal end portion of the flexible control wire outside of said flexible tube has an acutely angled curvature being in a range of between 0° and 90°.

12. The apparatus of claim 11, wherein said acutely angled curvature of said distal end portion of said flexible control wire has a length in a range of between a few millimeters and a few centimeters.

13. The apparatus of claim 10, wherein said flexible wire distal end portion outside of said flexible tube is thermally shaped or treated relative to remaining portion of said flexible control wire inside of said flexible tube.

14. The apparatus of claim 10, wherein, when said hole sealing assembly is in said reversibly collapsible activated, self-expanded configuration, after removal of said sheath from said hole sealing assembly, said opened proximal end of said sheath is a distance, of at least a few millimeters, and up to a few centimeters, away from said tubular distal end portion neck or apex of said hole sealing assembly.

15. The apparatus of claim 1, provided as a medical device kit for use in surgical vascular anastomotic procedures.

16. An apparatus for use in surgical vascular anastomotic procedures, comprising:
a blood vessel inner wall sealing and hole forming device, configured to atraumatically establish and maintain, inside a blood vessel lumen, along a blood vessel inner wall segment thereof, a peripheral seal around a needle sized hole in said blood vessel inner wall segment, absent of blood flow, and to form an anastomotic hole through said peripherally sealed blood vessel inner wall segment, in said blood flow absence;
and a hole forming actuator, reversibly connectable to, and configured for operating, said blood vessel inner wall sealing and hole forming device, wherein said blood vessel inner wall sealing and hole forming device includes an anastomotic hole generating device, configured to generate said anastomotic hole in said blood vessel inner wall segment, and comprising:
a tubular outer assembly, having an outer assembly central tubular cavity extending along entire longitudinal length of said tubular outer assembly; and
a tubular inner assembly, having an inner assembly central tubular cavity extending along entire longitudinal length of said tubular inner assembly;
said tubular inner assembly is longer than said tubular outer assembly, and has a portion thereof concentrically surrounded by and closely fitting within and along said tubular outer assembly, such that said tubular outer and inner assemblies are linearly translatable, and slidably movable forward and backward in distal and proximal directions, relative to each other, along a concentric longitudinal axis thereof;
said outer assembly and inner assembly central tubular cavities are configured to facilitate reversible passage therethrough of a flexible tube or wire; and
said tubular inner assembly has a distal end portion configured with a tubular anastomotic hole generating member that is configured to atraumatically pass through, via distally directed motion, said needle sized hole in said blood vessel inner wall segment, and to generate, via proximally directed motion, said anastomotic hole through said blood vessel inner wall segment, and to exit, via further proximally directed motion, said anastomotic hole generated through said blood vessel inner wall segment, wherein said tubular inner assembly includes a spring, configured to control and limit said linearly translatable and slidable relative motion of said tubular outer and inner assemblies, wherein said tubular inner assembly includes a longitudinal slot, which is coaxially inside the inner assembly central tubular cavity, and houses said spring, wherein said tubular inner assembly includes a pin that holds a proximal end of said spring in place inside said longitudinal slot.

17. The apparatus of claim 16, wherein said pin is housed in, and orthogonally extends across and through, the outer assembly central tubular cavity in a proximal end portion of said tubular outer assembly portion of said outer assembly.

18. The apparatus of claim 16, wherein said pin is held in place via a pair of two oppositely positioned holes located in a proximal end portion of said tubular outer assembly.

19. The apparatus of claim 16, wherein a distal end portion of said spring is held in place inside said longitudinal slot via a distal end of said inner assembly central tubular cavity.

20. The apparatus of claim 16, wherein a proximal end portion of said tubular inner assembly includes an inner protruding rim and an outer protruding rim, said inner protruding rim, along with said spring, is configured to limit said linearly translatable and slidable relative motion of said tubular outer and inner assemblies, and said outer protruding rim is configured to facilitate reversible connection of said anastomotic hole generating device with said hole forming actuator.

21. The apparatus of claim 16, wherein a proximal portion of said outer assembly includes a protruding rim configured to facilitate reversible connection thereof with said hole forming actuator.

22. The apparatus of claim 16, wherein a distal portion of said anastomotic hole generating member is configured as a tubular cone having a circular base and a tapered point or apex.

23. The apparatus of claim 22, wherein a proximal end portion of said anastomotic hole generating member tubular cone includes a non-beveled or non-tapered tubular segment that is continuous with, and proximally extending from, circular base.

24. The apparatus of claim 23, wherein said tubular segment has a form of a ring, whose outer diameter is equal to a diameter of said circular base, and whose longitudinal, proximal to a distal length is less than the proximal to distal height of said tubular cone.

25. The apparatus of claim 23, wherein a proximal end of said tubular segment has a sharp edge configured to cut through a blood vessel wall, from within said blood vessel inner wall segment, to outside said blood vessel inner wall segment, so as to generate said anastomotic hole through said blood vessel inner wall segment.

26. An apparatus for use in surgical vascular anastomotic procedures, comprising:
a blood vessel inner wall sealing and hole forming device, configured to atraumatically establish and maintain, inside a blood vessel lumen, along a blood vessel inner wall segment thereof, a peripheral seal around a needle sized hole in said blood vessel inner wall segment, absent of blood flow, and to form an anastomotic hole through said peripherally sealed blood vessel inner wall segment, in said blood flow absence;
and a hole forming actuator, reversibly connectable to, and configured for operating, said blood vessel inner wall sealing and hole forming device, wherein said hole forming actuator comprises:
a tubular outer assembly; and
a tubular inner assembly, longer than said tubular outer assembly, and having a portion thereof concentrically surrounded by and closely fitting within and along said tubular outer assembly, such that said tubular outer and inner assemblies are linearly translatable, and slidably movable forward and backward in distal and proximal directions, relative to each other, along a concentric longitudinal axis thereof, said tubular inner assembly has a distal end configured as a circular groove that is reversibly connectable to said blood vessel inner wall sealing and hole forming device;

said tubular outer assembly has a proximal end portion configured with a pair of oppositely positioned manually controllable guiding members that facilitate said linearly translatable and slidable relative motion of said tubular outer and inner assemblies; and said tubular outer assembly has a distal end portion configured with a pair of oppositely positioned manually controllable connector members that facilitate said reversible connectability of said circular groove to said blood vessel inner wall sealing and hole forming device.

27. The apparatus of claim 26, wherein said tubular inner assembly is configured with a pair of two oppositely positioned longitudinal side slots, narrow grooves, or channels, that distally to proximally extend along a middle longitudinal length to a proximal longitudinal length of two side portions of said inner assembly, and which additionally facilitate said linearly translatable and slidable relative motion between said outer and inner assemblies.

28. The apparatus of claim 26, wherein said hole forming actuator is configured with a single coaxial dual assembly longitudinal top slot, narrow groove, or channel, that extends from a distal end to near a proximal end of said hole forming actuator, and is used to receive and loosely enclose a flexible tube of said blood vessel inner wall sealing and hole forming device, so as to facilitate reversible connectability of said hole forming actuator with said blood vessel inner wall sealing and hole forming device.

29. The apparatus of claim 28, wherein said single coaxial dual assembly longitudinal top slot, narrow groove, or channel comprises an inner assembly longitudinal top slot, narrow groove, or channel configured in, and extending along, a top of said hole forming actuator tubular inner assembly, and an outer assembly longitudinal top slot, narrow groove, or channel configured in, and extending along, a top of said tubular outer assembly, whereby said inner and outer assembly longitudinal top slots, narrow grooves, or channels, are coaxial with each other.

30. A method for use in surgical vascular anastomotic procedures, the method comprising:
selecting a blood vessel in a subject for performing a surgical vascular anastomotic procedure;
providing an apparatus for use in performing the surgical vascular anastomotic procedure on the subject, the apparatus including
a blood vessel inner wall sealing and hole forming device, configured to atraumatically establish and maintain, inside a blood vessel lumen, along a blood vessel inner wall segment thereof, a peripheral seal around a needle sized hole in said blood vessel inner wall segment, absent of blood flow, and to form an anastomotic hole through said peripherally sealed blood vessel inner wall segment, in said blood flow absence;
and a hole forming actuator, reversibly connectable to, and configured for operating, said blood vessel inner wall sealing and hole forming device;
wherein said blood vessel inner wall sealing and hole forming device includes a hole sealing device, configured to atraumatically establish said peripheral seal, and comprising:
a hole sealing assembly, having a reversibly expandable non-activated, collapsed configuration and a reversibly collapsible activated, self-expanded configuration;
a sheath that externally fully covers, closely fits over, and holds said hole sealing assembly in said reversibly expandable non-activated, collapsed configuration, and configured to atraumatically entirely, with said hole sealing assembly in the collapsed configuration, enter into said blood vessel lumen, by passing through said needle sized hole and along said blood vessel inner wall segment;
a manual hole sealing controller assembly, operably connected to said sheath, and configured to facilitate manual control of said hole sealing assembly and said sheath;
a flexible control wire, having a distal end fixedly connected to an inside distal end of said sheath, and having a proximal portion fixedly connected to an inside distal portion of said manual hole sealing controller assembly, and configured to control motion and positioning of said sheath and reversible activation of said hole sealing assembly; and
a flexible tube, that encloses, holds, and guides motion of said flexible control wire;
and
operating the apparatus for establishing, and maintaining, said peripheral seal, before, during, and after, generating said anastomotic hole through said peripherally sealed blood vessel inner wall segment, in said blood flow absence.

31. The method of claim 30, wherein, after said establishing, and while said maintaining, of said peripheral seal around said blood vessel inner wall segment, in the absence of blood flow, there is starting the surgical vascular anastomotic procedure.

32. The method of claim 31, wherein said surgical vascular anastomotic procedure is an end-to-side blood vessel grafting procedure.

33. The method of claim 31, further comprising providing a blood vessel graft for use in performing a blood vessel grafting procedure on the subject's blood vessel.

* * * * *